US007598245B2

United States Patent
Arnost et al.

(10) Patent No.: US 7,598,245 B2
(45) Date of Patent: Oct. 6, 2009

(54) AMINOTRIAZOLE COMPOUNDS USEFUL AS INHIBITORS OF PROTEIN KINASES

(75) Inventors: Michael J. Arnost, North Andover, MA (US); Guy W. Bemis, Arlington, MA (US); Robert J. Davies, Arlington, MA (US); Cornelia J. Forster, Pelham, NH (US); Ronald Grey, Jr., Attleboro, MA (US); Mark W. Ledeboer, Acton, MA (US); Brian Ledford, Attleboro, MA (US); Craig Marhefka, Rockville, MD (US); David Messersmith, Somerville, MA (US); Albert C. Pierce, Cambridge, MA (US); Francesco G. Salituro, Marlboro, MA (US); Jian Wang, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 17 days.

(21) Appl. No.: 11/787,165

(22) Filed: Apr. 13, 2007

(65) Prior Publication Data
US 2008/0096901 A1  Apr. 24, 2008

Related U.S. Application Data

(62) Division of application No. 10/914,051, filed on Aug. 6, 2004, now Pat. No. 7,226,920.

(60) Provisional application No. 60/492,787, filed on Aug. 6, 2003.

(51) Int. Cl.
| | |
|---|---|
| *A61K 31/427* | (2006.01) |
| *A61K 31/5377* | (2006.01) |
| *C07D 413/12* | (2006.01) |
| *C07D 263/32* | (2006.01) |
| *C07D 249/08* | (2006.01) |

(52) U.S. Cl. .............. 514/236.2; 514/365; 514/378; 514/383; 544/132; 546/2; 548/202; 548/235; 548/264.8

(58) Field of Classification Search ............ 514/236.2, 514/365; 544/132; 548/264.8
See application file for complete search history.

(56) References Cited

U.S. PATENT DOCUMENTS

| 5,962,235 A | 10/1999 | Galivan et al. |
| 6,124,272 A | 9/2000 | Monia et al. |
| 6,806,282 B2 * | 10/2004 | Geslin et al. .............. 514/383 |
| 7,226,920 B2 * | 6/2007 | Arnost et al. ............ 514/236.2 |

FOREIGN PATENT DOCUMENTS

| EP | 0185401 | 6/1986 |
| WO | 0010563 | 3/2000 |
| WO | 02057240 | 7/2002 |
| WO | 03078423 | 9/2003 |

* cited by examiner

*Primary Examiner*—Golam M. M. Shameem
*Assistant Examiner*—Susannah Chung
(74) *Attorney, Agent, or Firm*—Daniel A. Pearson

(57) ABSTRACT

The present invention relates to inhibitors of protein kinases. The invention also provides pharmaceutical compositions comprising the compounds of the invention, processes for preparing the compounds and methods of using the compositions in the treatment of various disorders.

22 Claims, No Drawings

AMINOTRIAZOLE COMPOUNDS USEFUL AS INHIBITORS OF PROTEIN KINASES

CROSS-REFERENCE TO RELATED APPLICATIONS

This is a divisional application of U.S. patent application Ser. No. 10/914,051 filed Aug. 6, 2004 now U.S. Pat. No. 7,226,920, which claims the benefit, under 35 U.S.C. §119, of U.S. Provisional Application No. 60/492,787, filed Aug. 6, 2003, the entire disclosures of which are incorporated herein by reference.

TECHNICAL FIELD OF THE INVENTION

The present invention relates to inhibitors of protein kinases. The invention also provides processes for preparing the compounds of the present invention, pharmaceutical compositions comprising the compounds of the invention and methods of using the compounds and compositions in the treatment of various disorders.

BACKGROUND OF THE-INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell [Hardie; G. and Hanks, S. *The Protein Kinase Facts Book, I and II*, Academic Press, San Diego, Calif.: 1995]. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families, see, for example, Hanks et al., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; and Garcia-Bustos et al., *EMBO J.* 1994, 13, 2352-2361.

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

A family of type III receptor tyrosine kinases including Flt-3, c-Kit, PDGF-receptor and c-Fms play an important role in the maintenance, growth and development of hematopoietic and non-hematopoietic cells. [Scheijen et al., *Oncogene*, 2002, 21, 3314-3333 and Reilly, *British Journal of Haematology*, 2002, 116, 744-757]. Flt-3 and c-Kit regulate maintenance of stem cell/early progenitor pools as well the development of mature lymphoid and myeloid cells [Lyman et al., *Blood*, 1998, 91, 1101-1134]. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propagate the activation signal leading to growth, differentiation and survival. Some of the downstream regulators of Flt-3 and c-Kit receptor signaling include, PLCγ, PI3-kinase, Grb-2, SHIP and Src related kinases [Scheijen et al., *Oncogene*, 2002, 21, 3314-3333]. Both receptor tyrosine kinases have been shown to play a role in a variety of hematopoietic and non-hematopoietic malignancies. Mutations that induce ligand independent activation of Flt-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type Flt-3 or c-Kit can contribute to the malignant phenotype [Scheijen et al., *Oncogene*, 2002, 21, 3314-3333].

c-Fms encodes for macrophage colony stimulating factor receptor (M-CSF-1R) which is expressed predominately in the monocytes/macrophage lineage [Dai et al., *Blood*, 2002, 99, 111-120]. MCSF-1R and its ligand regulate macrophage lineage growth and differentiation. Like the other family members, MCSF-1R contains an intrinsic kinase domain that is activated upon ligand-induced dimerization of the receptor. MCSF-1R is also expressed in non-hematopoietic cells including mammary gland epithelial cells and neurons. Mutations in this receptor are potentially linked to myeloid leukemias and its expression is correlated with metastatic breast, ovarian and endometrial carcinomas [Reilly, *British Journal of Haematology*, 2002, 116, 744-757 and Kacinski, *Mol. Reprod. and Devel.*, 1997, 46, 71-74]. Another possible indication for antagonists of MCSF-1R is osteoporosis [Teitelbaum, *Science* 2000, 289, 1504-1508.

PDGF-receptor (PDGFR) has two subunits—PDGFR-α and PDGRR-β, that can form homo or heterodimers upon ligand binding. There are several PDGF ligands: AB, BB, CC and DD. PDGFR is expressed on early stem cells, mast cells, myeloid cells, mesenchymal cells and smooth muscle cells [Scheijen et al., *Oncogene*, 2002, 21, 3314-3333]. Only PDGFR-β has been implicated in myeloid leukemias—usually as a translocation partner with Tel, Huntingtin interacting protein (HIP1) or Rabaptin5. Recently it was shown that activation mutations in PDGFR-α kinase domain are in gastrointestinal stromal tumors (GIST) [Heinrich et al., *Sciencexpress*, 2003]

Cyclin-dependent kinases (CDKs) are serine/threonine protein kinases consisting of a β-sheet rich amino-terminal lobe and a larger carboxy-terminal lobe that is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, *Drug Resistance Updates* 2000, 3, 83-88].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, *Nature Reviews* 2001, 2, 21-32; Flatt et al., *Drug Metabolism Reviews* 2000, 32, 283-305].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the over-expression of cyclin D1 is commonly associated with numerous human cancers including breast, colon, hepatocellular carcinomas and gliomas [Flatt et al., *Drug Metabolism Reviews* 2000, 32, 283-305]. The CDK2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch et al., *The Cancer Journal* 2000, 6, 192-212].

CDKs, especially CDK2, also play a role in apoptosis and T-cell development. CDK2 has been identified as a key regulator of thymocyte apoptosis [Williams et al., *European Journal of Immunology* 2000, 709-713]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegakovirus, herpes virus, and varicella-zoster virus [Meijer, *Drug Resistance Updates* 2000, 3, 83-88].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, *Drug Resistance Updates,* 2000 3, 83-88].

Glycogen synthase kinase-3 (GSK-3) is a serine/threonine protein kinase comprised of α and β isoforms that are each encoded by distinct genes [Coghlan et al., *Chemistry & Biology* 2000, 7, 793-803; and Kim and Kimmel, *Curr. Opinion Genetics Dev.,* 2000 10, 508-514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117-130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor eIF2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455-8459; Cross et al., *Biochem. J.* 1994, 303, 21-26); Cohen, *Biochem. Soc. Trans.* 1993, 21, 555-567; and Massillon et al., *Biochem J.* 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is associated with Alzheimer's disease. This disease is characterized by the well-known β-amyloid peptide and the formation of intracellular neurofibrillary tangles. The neurofibrillary tangles contain hyperphosphorylated Tau protein, in which Tau is phosphorylated on abnormal sites. GSK-3 is known to phosphorylate these abnormal sites in cell and animal models. Furthermore, inhibition of GSK-3 has been shown to prevent hyperphosphorylation of Tau in cells [Lovestone et al., *Current Biology* 1994, 4, 1077-86; and Brownlees et al., *Neuroreport* 1997, 8, 3251-55]. Therefore, GSK-3 activity promotes generation of the neurofibrillary tangles and the progression of Alzheimer's disease.

Another substrate of GSK-3 is β-catenin, which is degradated after phosphorylation by GSK-3. Reduced levels of β-catenin have been reported in schizophrenic patients and have also been associated with other diseases related to increase in neuronal cell death [Zhong et al., *Nature* 1998, 395, 698-702; Takashima et al., *PNAS* 1993, 90, 7789-93; and Pei et al., *J. Neuropathol. Exp* 1997, 56, 70-78].

GSK-3 activity is associated with stroke [Wang et al., *Brain Res* 2000, 859, 381-5; Sasaki et al., Neurol Res 2001, 23, 588-92; Hashimoto et al., *J. Biol. Chem* 2002, 277, 32985-32991].

Another kinase family of particular interest is the Src family of kinases. These kinases are implicated in cancer, immune system dysfunction and bone remodeling diseases. For general reviews, see Thomas and Brugge, *Annu. Rev. Cell Dev. Biol.* 1997, 13, 513; Lawrence and Niu, *Pharmacol. Ther.* 1998, 77, 81; Tatosyan and Mizenina, *Biochemistry* (Moscow) 2000, 65, 49; and Boschelli et al., *Drugs of the Future* 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region [Tatosyan et al., *Biochemistry* (Moscow) 2000, 65, 49-58].

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src [Soriano et al., *Cell* 1992, 69, 551 and Soriano et al., *Cell* 1991, 64, 693].

Suppression of arthritic bone destruction has been achieved by the overexpression of CSK in rheumatoid synoviocytes and osteoclasts [Takayanagi et al., *J. Clin. Invest.* 1999, 104, 137]. CSK, or C-terminal Src kinase, phosphorylates and thereby inhibits Src catalytic activity. This implies that Src inhibition may prevent joint destruction that is characteristic in patients suffering from rheumatoid arthritis [Boschelli et al., *Drugs of the Future* 2000, 25(7), 717].

Src also plays a role in the replication of hepatitis B virus. The virally encoded transcription factor HBx activates Src in a step required for propagation of the virus [Klein et al., *EMBO J.* 1999, 18, 5019; and Klein et al., *Mol. Cell. Biol.* 1997, 17, 6427].

A number of studies have linked Src expression to cancers such as colon, breast, hepatic and pancreatic cancer, certain B-cell leukemias and lymphomas [Talamonti et al., *J. Clin. Invest.* 1993, 91, 53; Lutz et al., *Biochem. Biophys. Res.* 1998 243, 503; Rosen et al., *J. Biol. Chem.* 1986, 261, 13754; Bolen et al., *Proc. Natl. Acad. Sci. USA* 1987, 84, 2251; Masaki et al., *Hepatology* 1998, 27, 1257; Biscardi et al., *Adv. Cancer Res.* 1999, 76, 61; and Lynch et al., *Leukemia,* 1993, 7, 1416]. Furthermore, antisense Src expressed in ovarian and colon tumor cells has been shown to inhibit tumor growth [Wiener et al., *Clin. Cancer Res.,* 1999, 5, 2164; and Staley et al., *Cell Growth Diff.,* 1997, 8, 269].

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis [Molina et al., *Nature,* 1992, 357, 161]. Hck, Fgr and Lyn have been identified as important mediators of integrin signaling in myeloid leukocytes [Lowell et al., *J. Leukoc. Biol.,* 1999, 65, 313]. Inhibition of these kinase mediators may therefore be useful for treating inflammation [Boschelli et al., *Drugs of the Future* 2000, 25(7), 717].

Syk is a tyrosine kinase that plays a critical role in Fc☐RI mediated mast cell degranulation and eosinophil activation. Accordingly, Syk kinase is implicated in various allergic disorders, in particular asthma. It has been shown that Syk binds to the phosphorylated gamma chain of the Fc☐RI receptor via N-terminal SH2 domains and is essential for downstream signaling [Taylor et al., *Mol. Cell. Biol.* 1995, 15, 4149].

Inhibition of eosinophil apoptosis has been proposed as key mechanisms for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense) [Yousefi et al., *J. Exp. Med.* 1996, 183, 1407].

The role of Syk in FcγR dependent and independent response in bone marrow derived macrophages has been determined by using irradiated mouse chimeras reconstituted with fetal liver cells from Syk −/− embryos. Syk deficient macrophages were defective in phagocytosis induced by FcγR but showed normal phagocytosis in response to complement [Kiefer et al., *Mol. Cell Biol.* 1998, 18, 4209]. It has also been reported that aerosolized Syk antisense suppresses Syk expression and mediator release from macrophages [Stenton et al., *J. Immunology* 2000, 164, 3790].

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [*Frank Mol. Med.* 5, 432-456 (1999) & Seidel, et al, *Oncogene* 19, 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al, *Blood* 96, 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, *Nature* 346, 274-276 (1990) & Galli, *N. Engl. J. Med.,* 328, 257-265 (1993)]. A crucial role for JAK3 in IgE receptor-mediated mast cell responses in vitro and in vivo has been established [Malaviya, et al, *Biochem. Biophys. Res. Commun.* 257, 807-813 (1999)]. In addition, the prevention of type I hypersensitivity reactions, including anaphylaxis, mediated by mast cell-activation through inhibition of JAK3 has also been reported [Malaviya et al, *J. Biol. Chem.* 274, 27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 33, 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demonstrated that IL-4-mediated activation of IL-4/STAT pathway is mediated through the Janus Kinases (JAK 1 & 3) and that IL-4-associated JAK kinases are expressed in the RA synovium [Muller-Ladner, et al, *J. Immunol.* 164, 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu, et al, *Biochem. Biophys. Res. Commun.* 267, 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al, *Clin. Cancer Res.* 5, 1569-1582 (1999)]. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al, *EMBO J.* 17, 5321-5333 (1998)].

Inhibition of JAK 3 and TYK 2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al, *Proc. Nat. Acad. Sci. U.S.A.* 94, 6764-6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, *J. Immunol.* 159, 5206-5210 (1997)]. In addition, IL-6-mediated STAT3 activation was blocked by an inhibitor of JAK, leading to sensitization of myeloma cells to apoptosis [Catlett-Falcone, et al, *Immunity* 10, 105-115 (1999)].

The AGC sub-family of kinases phosphorylate their substrates at serine and threonine residues and participate in a variety of well-known signaling processes, including, but not limited to cyclic AMP signaling, the response to insulin, apoptosis protection, diacylglycerol signaling, and control of protein translation (Peterson et al., *Curr. Biol.* 1999, 9, R521). This sub-family includes PKA, PKB (c-Akt), PKC, PRK1, 2, $p70^{S6K}$, and PDK.

AKT (also known as PKB or Rac-PK beta), a serine/threonine protein kinase, has been shown to be overexpressed in several types of cancer and is a mediator of normal cell functions [(Khwaja, A., *Nature* 1999, 401, 33-34); (Yuan, Z. Q., et al., *Oncogene* 2000, 19, 2324-2330); (Namikawa, K., et al., *J Neurosci.* 2000, 20, 2875-2886,)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., *Proc. Natl. Acad. Sci. USA* 1992, 89, 9267-9271); (Brodbeck, D. et al., *J. Biol. Chem.* 1999, 274, 9133-9136)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., *Mol. Cell. Biol.*, 1997, 17, 1595-1606,); (Hemmings, B. A., *Science*, 1997, 275, 628-630)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., *J. Biol. Chem.* 1998, 273, 7201-7204) induction of differentiation and/or proliferation, protein synthesis and stress responses (Alessi, D. R. et al., *Curr. Opin. Genet. Dev.* 1998, 8, 55-62,).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., *Proc. Natl. Acad. Sci. U.S.A.* 1992, 89, 9267-9271). It has also been found to be overexpressed in 12% of pancreatic cancers (Cheng, J. Q. et al., *Proc. Natl. Acad. Sci. U.S.A.* 1996, 93, 3636-3641). It was demonstrated that AKT-2 was over-expressed in 12% of ovarian carcinomas and that amplification of AKT was especially frequent in 50% of undifferentiated tumours, suggesting that AKT may also be associated with tumour aggressiveness (Bellacosa, et al., *Int. J. Cancer* 1995, 64, 280-285).

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., *Semin. Cancer Biol.* 1994, 5, 285-294). PKA is a tetrameric holoenzyme, which contains two catalytic subunits bound to a homo-dimeric regulatory subunit (which acts to inhibit the catalytic subunits). On binding of cAMP (enzyme activation), the catalytic subunits dissociate from the regulatory subunits to yield the active serine/threonine kinase (McKnight, G. S. et al., *Recent Prog. Horm. Res.* 1988, 44, pp. 307). Three isoforms of the catalytic subunit (C-α, C-β and C-γ) have been reported to date (Beebe, S. J. et al., *J. Biol. Chem.* 1992, 267, 25505-25512) with the C-α subunit being the most extensively studied, primarily because of its elevated expression in primary and metastatic melanomas (Becker, D. et al., *Oncogene* 1990, 5, 1133). To date, strategies to modulate the activity of the C-α subunit involve the use of antibodies, molecules that block PKA activity by targeting regulatory dimers and antisense oligonucleotides expression.

The ribosomal protein kinases $p70^{S6K}$-1 and -2 are also members of the AGC sub-family of protein kinases and catalyze the phosphorylation and subsequent activation of ribosomal protein S6, which has been implicated in the translational up-regulation of mRNAs coding for the components of the protein synthetic apparatus. These mRNAs contain an oligopyrimidine tract at their 5' transcriptional start site, termed a 5'TOP, which has been shown to be essential for their regulation at the translational level (Volarevic, S. et al., *Prog. Nucleic Acid Res. Mol. Biol.* 2001, 65, 101-186). $p70^{S6K}$ dependent S6 phosphorylation is stimulated in response to a variety of hormones and growth factors primarily via the PI3K pathway (Coffer, P. J. et al., *Biochem. Biophys. Res. Commun*, 1994 198, 780-786), which may be under the regulation of mTOR, since rapamycin acts to inhibit $p70^{S6K}$ activity and blocks protein synthesis, specifically as a result of a down-regulation of translation of these mRNA's encoding ribosomal proteins (Kuo, C. J. et al., *Nature* 1992, 358, 70-73).

In vitro PDK1 catalyses the phosphorylation of Thr252 in the activation loop of the p70 catalytic domain, which is indispensable for p70 activity (Alessi, D. R., *Curr. Biol.*, 1998, 8, 69-81). The use of rapamycin and gene deletion studies of dp70S6K from Drosophila and $p70^{S6K}1$ from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., Biochem. Soc. Trans 2001, 29, 1). These include isoforms of protein kinase B (PKB, also known as AKT), p70 ribosomal S6 kinase (S6K) (Avruch, J. et al., Prog. Mol. Subcell. Biol. 2001, 26, 115), and p90 ribosomal S6 kinase (Frodin, M. et al., EMBO J. 2000, 19, 2924-2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., J. Cell Sci. 2001, 114, 2903-2910), (Lawlor, M. A. et al., EMBO J. 2002, 21, 3728-3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., Curr. Biol. 1999, 9, R93-R96). Many human cancers including prostate and NSCL have elevated PDK1 signaling pathway function resulting from a number of distinct genetic events such as PTEN mutations or over-expression of certain key regulatory proteins [(Graff, J. R., Expert Opin. Ther. Targets 2002, 6, 103-113), (Brognard, J., et al., Cancer Res. 2001, 61, 3986-3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., Curr. Biol. 2000, 10, 1439-1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., Cell 2000, 100, 57-70). PDK1 is a critical mediator of the PI3K signalling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Specifically, increased levels of PI3K pathway activity has been directly associated with the development of a number of human cancers, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., Cancer Res., 1997 57, 5221-5225), (Brognard, J. et al., Cancer Res., 2001, 61, 3986-3997), (Cheng, J. Q. et al., Proc. Natl. Acad. Sci. 1996, 93, 3636-3641), (Int. J. Cancer 1995, 64, 280), (Graff, J. R., Expert Opin. Ther. Targets 2002, 6, 103-113), (Am. J. Pathol. 2001, 159, 431)].

Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., Proc. Natl. Acad. Sci. 1996, 93, 3636-3641), (Neoplasia 2001, 3, 278)], lung [(Brognard, J. et al., Cancer Res. 2001, 61, 3986-3997), (Neoplasia 2001, 3, 278)], ovarian [(Hayakawa, J. et al., Cancer Res. 2000, 60, 5988-5994), (Neoplasia 2001, 3, 278)], breast (Mol. Cancer. Ther. 2002, 1, 707), colon [(Neoplasia 2001, 3, 278), (Arico, S. et al., J. Biol. Chem. 2002, 277, 27613-27621)], cervical (Neoplasia 2001, 3, 278), prostate [(Endocrinology 2001, 142, 4795), (Thakkar, H. et al. J. Biol. Chem. 2001, 276, 38361-38369), (Chen, X. et al., Oncogene 2001, 20, 6073-6083)] and brain (glioblastomas) [(Flynn, P. et al., Curr. Biol. 2000, 10, 1439-1442)].

KDR is a tyrosine kinase receptor that also binds VEGF (vascular endothelial growth factor) Neufeld et al., 1999, FASEB J., 13, 9. The binding of VEGF to the KDR receptor leads to angiogenesis, which is the sprouting of capillaries from preexisting blood vessels. High levels of VEGF are found in various cancers causing tumor angiogenesis and permitting the rapid growth of cancerous cells. Therefore, suppressing VEGF activity is a way to inhibit tumor growth, and it has been shown that this can be achieved by inhibiting KDR receptor tyrosine kinase. For example, SU5416 is a selective inhibitor of the tyrosine kinase and was reported to also suppress tumor vascularization and the growth of multiple tumors. Fong et al., 1999, Cancer Res. 59, 99. Other inhibitors of KDR tyrosine kinase for the treatment of cancer have also been reported (WO 98/54093, WO 99/16755, WO 00/12089).

Examples of cancers that may be treated by such inhibitors include brain cancer, genitourinary tract cancer, lymphatic system cancer, stomach cancer, cancer of the larynx, lung cancer, pancreatic cancer, breast cancer, Kaposi's sarcoma, and leukemia. Other diseases and conditions associated with abnormal tyrosine kinase activity include vascular disease, autoimmune diseases, ocular conditions, and inflammatory diseases.

Aurora-2 is a serine/threonine protein kinase that has been implicated in human cancer, such as colon, breast and other solid tumors. This kinase is involved in protein phosphorylation events that regulate the cell cycle. Specifically, Aurora-2 plays a role in controlling the accurate segregation of chromosomes during mitosis. Misregulation of the cell cycle can lead to cellular proliferation and other abnormalities. In human colon cancer tissue, the aurora-2 protein has been found to be overexpressed [Bischoff et al., EMBO J., 17, 3052-3065 (1998); Schumacher et al., J. Cell Biol., 143, 1635-1646 (1998); Kimura et al., J. Biol. Chem., 272, 13766-13771 (1997)].

Accordingly, there is a great need to develop inhibitors of protein kinases that are useful in treating various diseases or conditions associated with protein kinase activation, particularly given the inadequate treatments currently available for the majority of these disorders.

SUMMARY OF THE INVENTION

It has now been found that compounds of this invention, and pharmaceutically acceptable compositions thereof, are effective as inhibitors of protein kinases. In certain embodiments, these compounds, and pharmaceutically acceptable compositions thereof, are effective as inhibitors of PDK-1, FMS, c-KIT, GSK-3, CDK-2, SRC, JAK-1, JAK-2, JAK-3, TYK-2, FLT-3, KDR, PDGFR, ROCK, SYK, AUR-1, or AUR-2 protein kinases. These compounds have the general formula I:

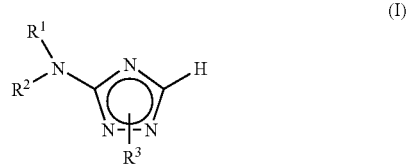

or a pharmaceutically acceptable derivative thereof, wherein $R^1$, $R^2$, and $R^3$ are as defined below.

These compounds and pharmaceutical compositions thereof are useful for treating or preventing a variety of disorders, including, but not limited to, allergic disorders, proliferative disorders, autoimmune disorders, conditions associated with organ transplant, inflammatory disorders, immunologically mediated disorders, viral diseases, or destructive bone disorders. The compositions are especially useful for treating cancer, including but not limited to one of the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

The compounds and compositions are also useful for treating or preventing immune responses such as allergic or type I hypersensitivity reactions, and asthma; autoimmune diseases such as transplant rejection, graft versus host disease, rheumatoid arthritis, amyotrophic lateral sclerosis, and multiple sclerosis; neurodegenerative disorders such as Familial amyotrophic lateral sclerosis (FALS); and solid and hematologic malignancies such as leukemias and lymphomas, in particular, acute-myelogenous leukemia (AML), acute-promyelocytic leukemia (APL), and acute lymphocytic leukemia (ALL).

DETAILED DESCRIPTION OF THE INVENTION

1. General Description of Compounds of the Invention

The present invention relates to a compound of formula I:

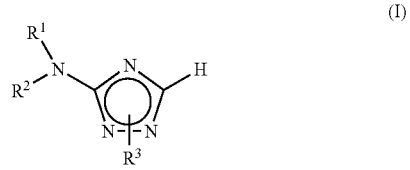

or a pharmaceutically acceptable salt thereof,
wherein $R^1$ is hydrogen or $C_{1-6}$ alkyl;

$R^2$ is $-(T)_nR$, $-(T)_nAr^1$, or $-(T)_nCy^1$, wherein T is an optionally substituted $C_{1-4}$ alkylidene chain wherein one methylene unit of T is optionally replaced by O, NR, NRCO, NRCONR, NRCO$_2$, CO, CO$_2$, CONR, OC(O)NR, SO$_2$, SO$_2$NR, NRSO$_2$, NRSO$_2$NR, C(O)C(O), or C(O)CH$_2$C(O); n is 0 or 1; Ar$^1$ is an optionally substituted aryl group selected from a 5-6 membered monocyclic or an 8-10 membered bicyclic ring having 0-5 heteroatoms independently selected from nitrogen, oxygen, or sulfur; and Cy$^1$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, or $R^1$ and $R^2$, taken together with the nitrogen form an optionally substituted 5-8 membered heterocyclyl or heteroaryl ring having 1-3 heteroatoms independently selected from nitrogen, oxygen, or sulfur;

wherein Ar$^1$, Cy$^1$, or any ring formed by $R^1$ and $R^2$ taken together, are each independently optionally substituted with 0-5 independent occurrences of Q-R$^X$; wherein each independent occurrence of Q is a bond or is a $C_{1-6}$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each independent occurrence of R$^X$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

$R^3$ is $-(L)_mR$, $-(L)_mAr^2$, or $-(L)_mCy^2$; wherein L is an optionally substituted $C_{1-4}$ alkylidene chain wherein one methylene unit of L is optionally replaced by O, NR, NRCO, NRCONR, NRCO$_2$, CO, CO$_2$, CONR, OC(O)NR, SO$_2$, SO$_2$NR, NRSO$_2$, NRSO$_2$NR, C(O)C(O), or C(O)CH$_2$C(O); m is 0 or 1; Ar$^2$ is an optionally substituted aryl group selected from a 5-6 membered monocyclic or an 8-10 membered bicyclic ring having 0-5 heteroatoms independently selected from nitrogen, oxygen, or sulfur; and Cy$^2$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein Ar$^2$ and Cy$^2$ are each independently optionally substituted with 0-5 independent occurrences of Z-R$^Y$; wherein each independent occurrence of Z is a bond or is a $C_{1-6}$ alkylidene chain wherein up to two non-adjacent methylene units of Z are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^Y$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; or $R^2$ and $R^3$, taken together, form an optionally substituted group selected from a 5-7-membered saturated, partially unsaturated, or fully unsaturated monocyclic ring having 0-3 heteroatoms independently selected from nitrogen, oxygen, or sulfur, or an 8-10-membered saturated, partially unsaturated, or fully unsaturated bicyclic ring system having 0-3 heteroatoms independently selected from nitrogen, oxygen, or sulfur;

wherein any ring formed by $R^2$ and $R^3$ taken together, is optionally substituted with 0-5 independent occurrences of W—$R^W$; wherein each independent occurrence of W is a bond or is a $C_{1-6}$ alkylidene chain wherein up to two non-adjacent methylene units of W are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^W$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$; and each occurrence of R is independently selected from hydrogen or an optionally substituted $C_{1-6}$ aliphatic group; and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together, or two occurrences of R' taken together, form a 5-8 membered cycloalkyl, heterocyclyl, aryl, or heteroaryl ring having 0-3 heteroatoms independently selected from nitrogen, oxygen, or sulfur, provided that:

A) for compounds having the general structure:

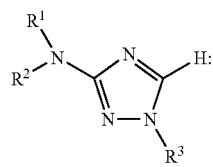

i) when $R^3$ is

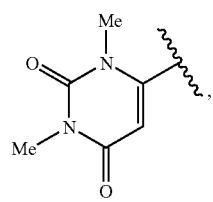

and $R^1$ is hydrogen, then $R^2$ is not

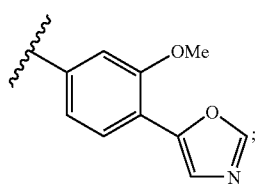

ii) when $R^3$ is methyl, and $R^1$ is hydrogen, then $R^2$ is not benz[cd]indol;

iii) when $R^3$ is —C(S)NHR" or —C(O)NHR", wherein R" is optionally substituted phenyl, benzyl, $CH_2C(O)OEt$, or naphthyl, and $R^1$ is hydrogen, then $R^2$ is not

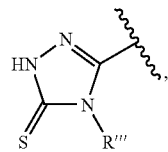

wherein R'" is optionally substituted group selected from phenyl, naphthyl, or benzyl, or is $CH_2C(O)OEt$;

iv) when $R^3$ is 4,6-dimethoxy 2-pyrimidinyl, and $R^1$ is hydrogen, then $R^2$ is not o-S(O)Me phenyl;

v) when $R^3$ is $C(O)NMe_2$, and $R^1$ is hydrogen, then $R^2$ is not substituted cycloheptatriene;

vi) when $R^3$ is Ac, and $R^1$ is hydrogen, then $R^2$ is not 2,4,6-trinitro-phenyl; or vii) when $R^3$ is unsubstituted phenyl, and $R^1$ is hydrogen, then $R^2$ is not unsubstituted phenyl or Ac;

viii) when $R^3$ is 2-methyl-phenyl or 4-methyl-phenyl, and $R^1$ is hydrogen, then $R^2$ is not 2-Me-phenyl or 4-Me-phenyl;

ix) when $R^1$ is H, and $R^2$ is —(C=O)$CH_2$-piperidinyl, or —(C=O)$CH_2$—Cl, then $R^3$ is not:

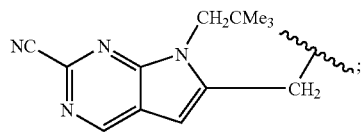

x) when $R^1$ is H, and $R^2$ is $COCH_3$, then $R_3$ is not $COCH_3$, —CH=$CH_2$, 1-(2,3,4,6-tetra-O-acetyl-β-D-glucopyranosyl, or

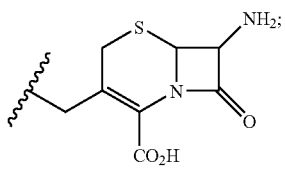

xi) when $R^1$ is H, and $R^2$ is —(C=O)benzyl, then $R^3$ is not phenyl substituted with 4-$NHCH_2CH(OH)NHCOCH_3$ or 2-fluoro-phenyl substituted with

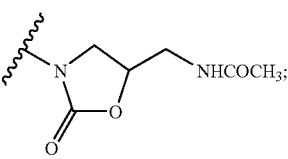

xii) when $R^1$ is H, and $R^2$ is —$(CH_2)_{11}CH_3$, then $R^2$ is not —CONH(2,6-isopropyl-phenyl);

xiii) when $R^1$ is H, and $R^2$ is —CO$(CH_2)_{12}$Me, then $R^3$ is not CH(COOEt)CONH(2-Cl, 5-$SO_2NHCOCH_3$)phenyl;

xiv) when $R^1$ is H, and $R^2$ is —CO(2-OH-phenyl) or —$COCH_3$, then $R^3$ is not —CH(OH)$CH_2$OH;

xv) when $R^1$ is H, and $R^2$ is CO(unsubstituted phenyl), then $R^3$ is not 4-Me-phenyl, 4-$NO_2$-phenyl, 4-OMe-phenyl, 4-Cl-phenyl, 3-Cl-phenyl, or 3-$NO_2$-phenyl;

xvi) when R¹ is H, R² is —OCF₃, then R³ is not (1-tricyclo [3.3.1.13,7]dec-1-yl);

xvii) when R¹ is H, and R² is 2-Cl-benzyl or 2-CO₂H-benzyl, then R³ is not 4,6-Me-pyrimidin-2-yl, or 4-OMe, 6-NMe₂-pyridin-2-yl;

xviii) when R¹ is H, and R² is —COC(=CH₂)Me, then R³ is not 4-NO₂-phenyl;

xix) when R¹ is hydrogen, and R² is —CO(CH₂)₂Cy¹, —COCH(isopropyl)Cy¹, —COCH(isobutyl)Cy¹, —COCH₂NHSO₂Cy¹, —COCH(Me)NHSO₂Cy¹, or —COCH(isopropyl)NHSO₂Cy¹, then R³ is not —COCH(isopropyl)Cy², —COCH(isobutyl)Cy², —COCH₂NHSO₂Cy², —COCH(Me)NHSO₂Cy², or —COCH(isopropyl)NHSO₂Cy²;

xx) when R¹ is hydrogen, and R² is —COR', where R' is hydrogen, CH₃, unsubstituted phenyl, —(CH₂)₂COOH, CF₃, n-propyl, ethyl, —CH₂Cl, —CCl₃, or cyclopropyl, then R³ is not 4-Me-phenyl, 4-NO₂-phenyl, or —CON(R')₂;

xxi) when R³ is 4,6-OMe-triazen-2-yl, and R¹ is H, then R² is not —CONH(3-Cl-phenyl), —CONH(2,3-Cl-phenyl), or —CONH(4-Cl-phenyl);

xxii) when R³ is unsubstituted benzyl, and R¹ is H, then R² is not —CO(4-Me-phenyl), —CO(2-Me-phenyl), —CO(3,4,5-OMe-phenyl), —CO(2,4-NO₂-phenyl), —CO(3,5-NO₂-phenyl), or —CO(4-SO₂NEt₂-phenyl);

xxiii) when R¹ is H, and R² is —CONHC(CF₃)₂Et, then R³ is not —CONHC(CF₃)₂Et;

xiv) when R¹ is H, and R² is —CO(CH₂)₂(5-Me-furan-2-yl), then R³ is not —CO(CH₂)₂(5-furan-2-yl);

xv) when R¹ is H, and R² is —C(CF₃)₂NHCOOEt, then R³ is not —C(CF₃)₂NHCOOEt;

xvi) when R³ is 3-Cl, 5-CF₃-pyridin-2-yl, and R¹ is H, then R² is not —CO(2-Cl-phenyl), —CO(4-Cl-phenyl), or —CONH(4-Cl-phenyl);

xvii) when R¹ is H, and R² is —COCF₂CF₂CF₃, then R³ is not —CH₂C(COOCH₂CH(CH₃)₂)NHCOCF₂CF₂CF₃; or xviii) when R¹ is H, and R² is —COCH₂CH₂CH₃, then R³ is not —COCH₂CH₂CH₃; and B) for compounds having the structure:

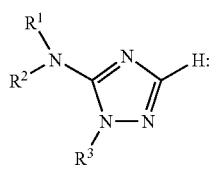

i) when R³ is methyl, R¹ is hydrogen, then R² is not optionally substituted benzopyran;

ii) when R¹ is C(S)NHAc, R² is 4-Me-phenyl, then R³ is not benzyl;

iii) when R¹ is hydrogen, and R² is optionally substituted phenyl, then R³ is not benzyl; or iv) when R¹ is hydrogen, and R² is 2,4,6-nitro-phenyl, then R³ is not 2,4,6-nitro-phenyl.

The present invention also relates to a compound of formula (I):

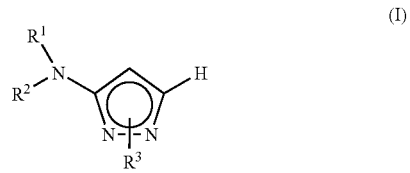

or a pharmaceutically acceptable salt thereof,
wherein R¹ is hydrogen or $C_{1-6}$ alkyl;

R² is —(T)ₙR, —(T)ₙAr¹, or —(T)ₙCy¹, wherein T is a $C_{1-4}$ alkylidene chain optionally substituted with J or J' wherein one methylene unit of T is optionally replaced by O, NR, NRCO, NRCONR, NRCO₂, CO, CO₂, CONR, OC(O)NR, SO₂, SO₂NR, NRSO₂, NRSO₂NR, C(O)C(O), or C(O)CH₂C(O); n is 0 or 1; Ar¹ is an aryl group selected from a 5-6 membered monocyclic or an 8-10 membered bicyclic ring having 0-5 heteroatoms independently selected from nitrogen, oxygen, or sulfur; and Cy¹ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur;

or R¹ and R², taken together with the nitrogen form an 5-8 membered heterocyclyl or heteroaryl ring having 1-3 heteroatoms independently selected from nitrogen, oxygen, or sulfur;

wherein Ar¹, Cy¹, or any ring formed by R¹ and R² taken together, are each independently and optionally substituted with 0-5 independent occurrences of Q-R$^X$; wherein each independent occurrence of Q is a bond or is a $C_{1-6}$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each independent occurrence of R$^X$ is independently selected from R', halogen, NO₂, CN, OR', SR', N(R')₂, NR'C(O)R', NR'C(O)N(R')₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R';

R³ is —(L)ₘR, —(L)ₘAr², or —(L)ₘCy²; wherein L is a $C_{1-4}$ alkylidene chain optionally substituted with J or J' wherein one methylene unit of L is optionally replaced by O, NR, NRCO, NRCONR, NRCO₂, CO, CO₂, CONR, OC(O)NR, SO₂, SO₂NR, NRSO₂, NRSO₂NR, C(O)C(O), or C(O)CH₂C(O); m is 0 or 1; Ar² is an optionally substituted aryl group selected from a 5-6 membered monocyclic or an 8-10 membered bicyclic ring having 0-5 heteroatoms independently selected from nitrogen, oxygen, or sulfur; and Cy² is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein Ar² and Cy² are each independently optionally substituted with 0-5 independent occurrences of Z-R$^Y$; wherein each independent occurrence of Z is a bond or is a $C_{1-6}$ alkylidene chain wherein up to two non-adjacent methylene units of Z are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of R$^Y$ is independently selected from R', halogen, NO₂, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; or R$^2$ and R$^3$, taken together, form an optionally substituted group selected from a 5-7-membered saturated, partially unsaturated, or fully unsaturated monocyclic ring having 0-3 heteroatoms independently selected from nitrogen, oxygen, or sulfur, or an 8-10-membered saturated, partially unsaturated, or fully unsaturated bicyclic ring system having 0-3 heteroatoms independently selected from nitrogen, oxygen, or sulfur;

wherein any ring formed by R$^2$ and R$^3$ taken together, is optionally substituted with 0-5 independent occurrences of W—R$^W$; wherein each independent occurrence of W is a bond or is a C$_{1-6}$ alkylidene chain wherein up to two non-adjacent methylene units of W are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^W$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; and each occurrence of R is independently selected from hydrogen or a C$_{1-6}$ aliphatic group optionally substituted with J or J'; and each occurrence of R' is independently selected from hydrogen or a group selected from C$_{1-8}$ aliphatic optionally substituted with J or J', C$_{6-10}$ aryl optionally substituted with J, a heteroaryl ring having 5-10 ring atoms optionally substituted with J, or a heterocyclyl ring having 3-10 ring atoms optionally substituted with J or J', or wherein R and R' taken together, or two occurrences of R' taken together, form a 5-8 membered cycloalkyl, heterocyclyl, aryl, or heteroaryl ring having 0-3 heteroatoms independently selected from nitrogen, oxygen, or sulfur, each ring being optionally and independently substituted with J (0, 1, 2, 3, 4, 5, or 6 J groups), each occurrence of J is independently selected from halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph) optionally substituted with R°; —CH═CH(Ph) optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)C(O)OR°; —C(O)C(O)N(R°)$_2$; —C(O)CH$_2$C(O)R°; —CO$_2$R°; —C(O)R°; —C(S)R°; —C(S)OR°, —C(O)N(R°)$_2$; —C(S)N(R°)$_2$; —C(═NH)—N(R°)$_2$, —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R')$_2$; —NR°SO$_2$R°; —N(OR°)R°; —C(═NH)—N(R°)$_2$; C(═NOR°)R°; (CH$_2$)$_{0-2}$NHC(O)R°; —P(O)$_2$R°; —PO(R°)$_2$; —OPO(R°)$_2$; or —P(O)(H)(OR°);

wherein each independent occurrence of R° is selected from hydrogen, optionally substituted C$_{1-6}$ aliphatic, optionally substituted 5-6 membered heteroaryl or heterocyclic ring, optionally substituted phenyl (Ph); optionally substituted —O(Ph); optionally substituted —(CH$_2$)$_{1-2}$(Ph); optionally substituted —CH═CH(Ph); or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur;

wherein a substituent for an aliphatic group of R° is optionally substituted heteroaryl, optionally substituted, heterocyclic, NH$_2$, NH(C$_{1-6}$ aliphatic), N(C$_{1-6}$ aliphatic)$_2$, halogen, C$_{1-6}$ aliphatic, OH, O(C$_{1-6}$ aliphatic), NO$_2$, CN, CO$_2$H, CO$_2$(C$_{1-6}$ aliphatic), O(halo C$_{1-6}$ aliphatic), or halo(C$_{1-6}$ aliphatic), wherein each of these C$_{1-6}$ aliphatic groups of R° is unsubstituted;

wherein a substituent for a phenyl, heteroaryl or heterocyclic group of R° is C$_{1-6}$ aliphatic, NH$_2$, NH(C$_{1-4}$ aliphatic), N(C$_{1-6}$ aliphatic)$_2$, halogen, C$_{1-6}$ aliphatic, OH, O(C$_{1-6}$ aliphatic), NO$_2$, CN, CO$_2$H, CO$_2$(C$_{1-6}$ aliphatic), O(halo C$_{1-6}$ aliphatic), or halo(C$_{1-6}$ aliphatic), wherein each of these C$_{1-6}$ aliphatic groups of R° is unsubstituted;

each occurrence of J' is independently selected from ═O, ═S, ═NNHR*, ═NN(R*)$_2$, ═NNHC(O)R*, ═NNHCO$_2$(alkyl), ═NNHSO$_2$(alkyl), or ═NR*, where each R* is independently selected from hydrogen or an optionally substituted C$_{1-6}$ aliphatic; wherein an aliphatic group of R* is optionally substituted with NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the C$_{1-4}$ aliphatic groups of R* is unsubstituted;

provided that when R$^3$ is a 6-membered aromatic or heteroaromatic ring, then R$^2$ is not H and T is not SO$_2$; and when R$^3$ is methyl then R$^2$ is not:

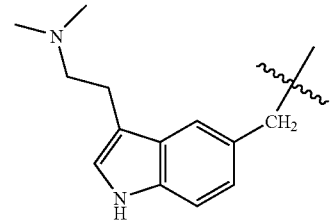

and provided that:

A) for compounds having the general structure:

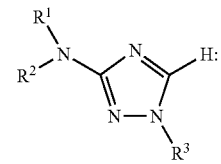

i) when R$^3$ is

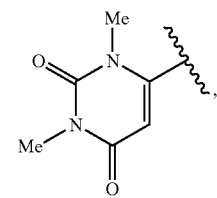

and $R^1$ is hydrogen, then $R^2$ is not

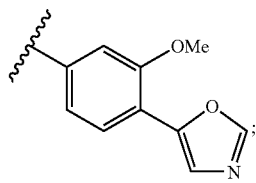

ii) when $R^3$ is methyl, and $R^1$ is hydrogen, then $R^2$ is not benz[cd]indol;

iii) when $R^3$ is —C(S)NHR″ or —C(O)NHR″, wherein R″ is optionally substituted phenyl, benzyl, $CH_2C(O)OEt$, or naphthyl, and $R^1$ is hydrogen, then $R^2$ is not

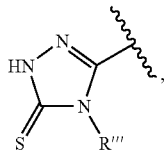

wherein R‴ is optionally substituted group selected from phenyl, naphthyl, or benzyl, or is $CH_2C(O)OEt$;

iv) when $R^3$ is 4,6-dimethoxy 2-pyrimidinyl, and $R^1$ is hydrogen, then $R^2$ is not o-S(O)Me phenyl;

v) when $R^3$ is $C(O)NMe_2$, and $R^1$ is hydrogen, then $R^2$ is not substituted cycloheptatriene;

vi) when $R^3$ is Ac, and $R^1$ is hydrogen, then $R^2$ is not 2,4,6-trinitro-phenyl; or vii) when $R^3$ is unsubstituted phenyl, and $R^1$ is hydrogen, then $R^2$ is not unsubstituted phenyl or Ac;

viii) when $R^3$ is 2-methyl-phenyl or 4-methyl-phenyl, and $R^1$ is hydrogen, then $R^2$ is not 2-Me-phenyl or 4-Me-phenyl;

ix) when $R^1$ is H, and $R^2$ is —(C=O)$CH_2$-piperidinyl, or —(C=O)$CH_2$—Cl, then $R^3$ is not:

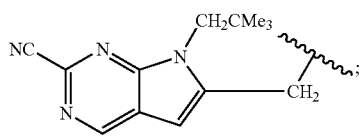

x) when $R^1$ is H, and $R^2$ is $COCH_3$, then $R_3$ is not $COCH_3$, —CH=$CH_2$, 1-(2,3,4,6-tetra-O-acetyl-β-D-glucopyranosyl, or

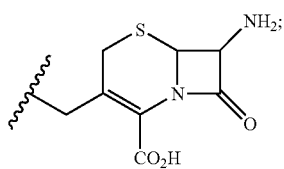

xi) when $R^1$ is H, and $R^2$ is —(C=O)benzyl, then $R^3$ is not phenyl substituted with 4-NH$CH_2$CH(OH)NHCOCH$_3$ or 2-fluoro-phenyl substituted with

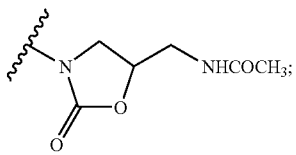

xii) when $R^1$ is H, and $R^2$ is —(CH$_2$)$_{11}$CH$_3$ or —(CH$_2$)$_{10}$CH$_3$, then $R^2$ is not —CONH(2,6-isopropyl-phenyl);

xiii) when $R^1$ is H, and $R^2$ is —CO(CH$_2$)$_{12}$Me, then $R^3$ is not CH(COOEt)CONH(2-Cl, 5-SO$_2$NHCOCH$_3$)phenyl;

xiv) when $R^1$ is H, and $R^2$ is —CO(2-OH-phenyl) or —COCH$_3$, then $R^3$ is not —CH(OH)CH$_2$OH;

xv) when $R^1$ is H, and $R^2$ is —CO(unsubstituted phenyl), then $R^3$ is not 4-Me-phenyl, 4-NO$_2$-phenyl, 4-OMe-phenyl, 4-Cl-phenyl, 3-Cl-phenyl, or 3-NO$_2$-phenyl;

xvi) when $R^1$ is H, $R^2$ is —COCF$_3$, then $R^3$ is not (1-tricyclo[3.3.1.13,7]dec-1-yl);

xvii) when $R^1$ is H, and $R^2$ is 2-Cl-benzyl or 2-CO$_2$H-benzyl, then $R^3$ is not 4,6-Me-pyrimidin-2-yl, or 4-OMe, 6-NMe$_2$-pyrimidin-2-yl;

xviii) when $R^1$ is H, and $R^2$ is —COC(=CH$_2$)Me, then $R^3$ is not 4-NO$_2$-phenyl;

xix) when $R^1$ is hydrogen, and $R^2$ is —CO(CH$_2$)$_2$Cy$^1$, —COCH(isopropyl)Cy$^1$, —COCH(isobutyl)Cy$^1$, —COCH$_2$NHSO$_2$Cy$^1$, —COCH(Me)NHSO$_2$Cy$^1$, or —COCH(isopropyl)NHSO$_2$Cy$^1$, then $R^3$ is not —COCH(isopropyl)Cy$^2$, —COCH(isobutyl)Cy$^2$, —COCH$_2$NHSO$_2$Cy$^2$, —COCH(Me)NHSO$_2$Cy$^2$, or —COCH(isopropyl)NHSO$_2$Cy$^2$;

xx) when $R^1$ is hydrogen, and $R^2$ is —COR', where R' is hydrogen, CH$_3$, unsubstituted phenyl, —(CH$_2$)$_2$COOH, CF$_3$, n-propyl, ethyl, —CH$_2$Cl, —CCl$_3$, or cyclopropyl, then $R^3$ is not 4-Me-phenyl, 4-NO$_2$-phenyl, or —CON(R')$_2$;

xxi) when $R^3$ is 4,6-OMe-triazen-2-yl, and $R^1$ is H, then $R^2$ is not —CONH(3-Cl-phenyl), —CONH(2,3-Cl-phenyl), or —CONH(4-Cl-phenyl);

xxii) when $R^3$ is unsubstituted benzyl, and $R^1$ is H, then $R^2$ is not —CO(4-Me-phenyl), —CO(2-Me-phenyl), —CO(3,4, 5-OMe-phenyl), —CO(2,4-NO$_2$-phenyl), —CO(3,5-NO$_2$-phenyl), or —CO(4-SO$_2$NEt$_2$-phenyl);

xxiii) when $R^1$ is H, and $R^2$ is —CONHC(CF$_3$)$_2$Et, then $R^3$ is not —CONHC(CF$_3$)$_2$Et;

xiv) when $R^1$ is H, and $R^2$ is —CO(CH$_2$)$_2$(5-Me-furan-2-yl), then $R^3$ is not —CO(CH$_2$)$_2$(5-furan-2-yl);

xv) when $R^1$ is H, and $R^2$ is —C(CF$_3$)$_2$NHCOOEt, then $R^3$ is not —C(CF$_3$)$_2$NHCOOEt;

xvi) when $R^3$ is 3-Cl, 5-CF$_3$-pyridin-2-yl, and $R^1$ is H, then $R^2$ is not —CO(2-Cl-phenyl), —CO(4-Cl-phenyl), or —CONH(4-Cl-phenyl);

xvii) when $R^1$ is H, and $R^2$ is —COCF$_2$CF$_2$CF$_3$, then $R^3$ is not —CH$_2$C(COOCH$_2$CH(CH$_3$)$_2$)NHCOCF$_2$CF$_2$CF$_3$; or xviii) when $R^1$ is H, and $R^2$ is —COCH$_2$CH$_2$CH$_3$, then $R^3$ is not —COCH$_2$CH$_2$CH$_3$; and B) for compounds having the structure:

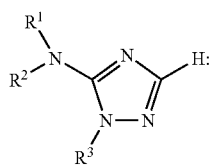

i) when $R^3$ is methyl, $R^1$ is hydrogen, then $R^2$ is not optionally substituted benzopyran;

ii) when $R^1$ is C(S)NHAc, $R^2$ is 4-Me-phenyl, then $R^3$ is not benzyl;

iii) when $R^1$ is hydrogen, and $R^2$ is optionally substituted phenyl, then $R^3$ is not benzyl;

iv) when $R^1$ is hydrogen, and $R^2$ is 2,4,6-nitro-phenyl, then $R^3$ is not 2,4,6-nitro-phenyl; or v) when $R^1$ is H, and $R^2$ is —$(CH_2)_{11}CH_3$ or —$(CH_2)_{10}CH_3$, then $R^2$ is not —CONH(2,6-isopropyl-phenyl).

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999; "March's Advanced Organic Chemistry", 5th Ed., Ed.: Smith, M. B. and March, J., John Wiley & Sons, New York: 2001; "Encyclopedia of Organic Transformations"; Ed.: Richard C. Larock, John Wiley & Sons, New York: 1999; "Encyclopedia of Reagents for Organic Synthesis" Ed.: Leo A. Paquette, John Wiley & Sons, New York: 1995; T. W. Greene & P. G. M Wutz, "Protective Groups in Organic Synthesis", 3rd Edition, John Wiley & Sons, Inc. (1999) (and earlier editions) the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle", "cycloaliphatic", or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle", or "cycloalkyl") refers to a monocyclic $C_{3-8}$ hydrocarbon or bicyclic $C_{8-12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include benzimidazolone (e.g., 3-1H-benzimidazol-2-one, 3-(1-alkyl)-benzimidazol-2-one), tetrahydrofuranyl (e.g., 2-tetrahydrofuranyl, 3-tetrahydrofuranyl), tetrahydrothiophenyl (e.g., 2-tetrahydrothiophenyl, 3-tetrahydrothiophenyl), morpholino (e.g., 2-morpholino, 3-morpholino, 4-morpholino), thiomorpholino (e.g., 2-thiomorpholino, 3-thiomorpholino, 4-thiomorpholino), pyrrolidinyl (e.g., 1-pyrrolidinyl, 2-pyrrolidinyl, 3-pyrrolidinyl), tetrahydropiperazinyl (e.g., 1-tetrahydropiperazinyl, 2-tetrahydropiperazinyl, 3-tetrahydropiperazinyl), piperidinyl (e.g., 1-piperidinyl, 2-piperidinyl, 3-piperidinyl, 4-piperidinyl), pyrazolinyl (e.g., 1-pyrazolinyl, 3-pyrazolinyl, 4-pyrazolinyl, 5-pyrazolinyl), thiazolidinyl (e.g., 2-thiazolidinyl, 3-thiazolidinyl, 4-thiazolidinyl), imidazolidinyl (e.g., 1-imidazolidinyl, 2-imidazolidinyl, 4-imidazolidinyl, 5-imidazolidinyl), indolinyl, tetrahydroquinolinyl, tetrahydroisoquinolinyl, benzothiolane, benzodithiane, and dihydro-imidazol-2-one (1,3-dihydro-imidazol-2-one).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl), or NR$^+$ (as in N-substituted pyrrolidinyl)).

The term "unsaturated", as used herein, means that a moiety has one or more units of unsaturation.

The term "alkoxy" or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

Examples of heteroaryl rings include furanyl (e.g., 2-furanyl, 3-furanyl), imidazolyl (e.g., N-imidazolyl, 2-imidazolyl, 4-imidazolyl, 5-imidazolyl)benzimidazolyl, isoxazolyl (e.g., 3-isoxazolyl, 4-isoxazolyl, 5-isoxazolyl)oxazolyl (e.g., 2-oxazolyl, 4-oxazolyl, 5-oxazolyl), pyrrolyl, (e.g., N-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), tetrazolyl (e.g., 5-tetrazolyl), triazolyl (e.g., 2-triazolyl and 5-triazolyl), thienyl, (e.g., 2-thienyl, 3-thienyl), benzofuryl, thiophenyl, benzothiophenyl, indolyl (e.g., 2-indolyl), pyrazolyl (e.g., 2-pyrazolyl), isothiazolyl, oxadiazolyl (e.g., 1,2,3-oxadiazolyl), oxadiazolyl (e.g., 1,2,5-oxadiazolyl), oxadiazolyl (e.g., 1,2,4-oxadiazolyl), triazolyl (e.g., 1,2,3-triazolyl), thiadiazolyl (e.g., 1,2,3-thiadiazolyl), thiadiazolyl (e.g., 1,3,4-thiadiazolyl), thiadiazolyl (e.g., 1,2,5-thiadiazolyl), purinyl, pyrazinyl, triazinyl (e.g., 1,3,5-triazinyl), quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R$^o$; —OR$^o$; —SR$^o$; 1,2-methylenedioxy; 1,2-ethylenedioxy; phenyl (Ph) optionally substituted with R$^o$; —O(Ph) optionally substituted with R$^o$; —(CH$_2$)$_{1-2}$(Ph) optionally substituted with R$^o$; —CH=CH(Ph) optionally substituted with R$^o$; —NO$_2$; —CN; —N(R$^o$)$_2$; —NR$^o$C(O)R$^o$; —NR$^o$C(S) R$^o$; —NR$^o$C(O)N(R$^o$)$_2$; —NR$^o$C(S)N(R$^o$)$_2$; —NR$^o$CO$_2$R$^o$; —NR$^o$NR$^o$C(O)R$^o$; —NR$^o$NR$^o$C(O)N(R$^o$)$_2$; —NR$^o$NR$^o$CO$_2$R$^o$; —C(O)C(O)R$^o$; —C(O)CH$_2$C(O)R$^o$; —CO$_2$R$^o$; —C(O)R$^o$; —C(S)R$^o$; —C(O)N(R$^o$)$_2$; —C(S)N (R$^o$)$_2$; —C(=NH)—N(R$^o$)$_2$, —OC(O)N(R$^o$)$_2$; —OC(O)R$^o$; —C(O)N(OR$^o$) R$^o$; —C(NOR$^o$)R$^o$; —S(O)$_2$R$^o$; —S(O)$_3$R$^o$; —SO$_2$N(R$^o$)$_2$; —S(O)R$^o$; —NR$^o$SO$_2$N(R$^o$)$_2$; —NR$^o$SO$_2$R$^o$; —N(OR$^o$)R$^o$; —C(=NH)—N(R$^o$)$_2$; or —(CH$_2$)$_{0-2}$NHC(O) R$^o$ wherein each independent occurrence of R$^o$ is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R$^o$, on the same substituent or different substituents, taken together with the atom(s) to which each R$^o$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R$^o$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R$^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O) R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, Cl$_4$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R* is unsubstituted.

Optional substituents on the nitrogen of a non-aromatic heterocyclic ring are selected from —R$^+$, —N(R$^+$)$_2$, —C(O) R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N (R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$ (Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R$^o$ (or R$^+$, or any other variable similarly defined herein), are taken together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R$^o$ (or R$^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of $OR^o$

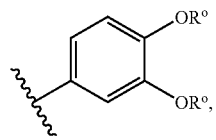

these two occurrences of $R^o$ are taken together with the oxygen atoms to which they are bound to form a fused 6-membered oxygen containing ring:

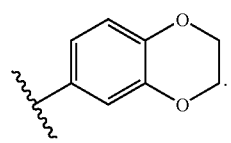

It will be appreciated that a variety of other rings can be formed when two independent occurrences of $R^o$ (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a $^{12}C$ carbon by a $^{13}C$ or $^{14}C$ carbon are within the scope of this invention. Such compounds are useful, for example, as analytical tools or probes in biological assays.

3. Description of Exemplary Compounds

As described generally above for compounds of formula I, in certain embodiments, $R^2$ is $—(T)_n Ar^1$. In certain preferred embodiments, $Ar^1$ is selected from one of the following groups:

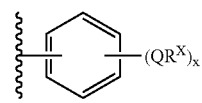 a

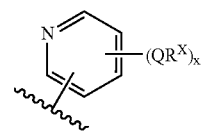 b

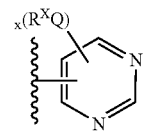 c

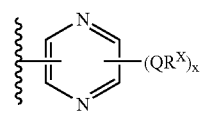 d

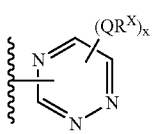 e

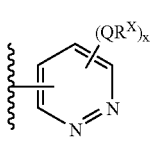 f

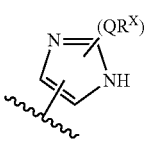 g

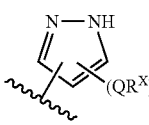 h

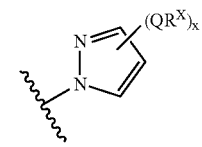 i

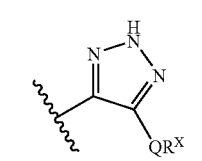 j

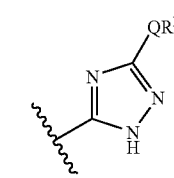 k

-continued

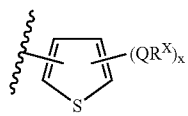 l

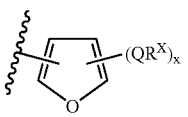 m

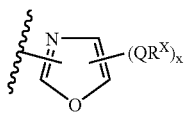 n

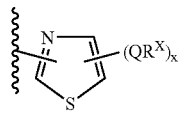 o

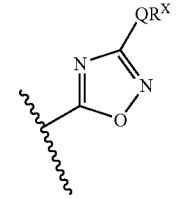 p

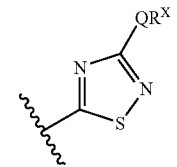 q

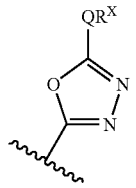 r

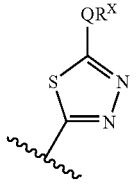 s

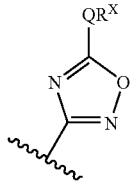 t

-continued

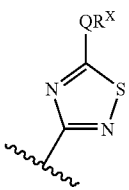 u wherein Q and $R^X$ are as defined generally above and in classes and subclasses herein, and x is 0-5.

In more preferred embodiments, $Ar^1$ is selected from optionally substituted phenyl (a), pyridyl (b) (preferably attached in the 2-, 3-, or 4-position as shown by b-i, b-ii, and b-iii), pyrimidinyl (c) (preferably attached in the 2-, 5-, or 6-position as shown by c-i, c-ii, and c-iii), and pyrazinyl (d):

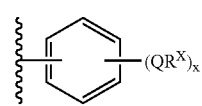 a

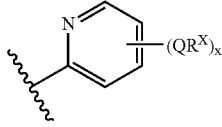 b-i

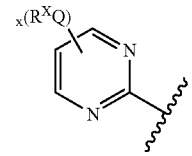 c-i

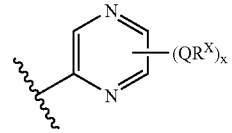 d

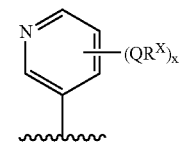 b-ii

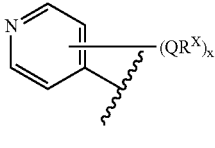 b-iii

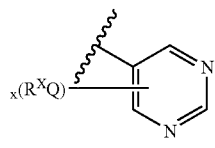 c-ii

-continued

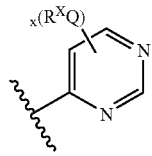
c-iii

In most preferred embodiments R¹ is hydrogen; R² is —(T)$_n$Ar¹; Ar¹ is optionally substituted phenyl (a); and compounds have the formula I-A or I-A':

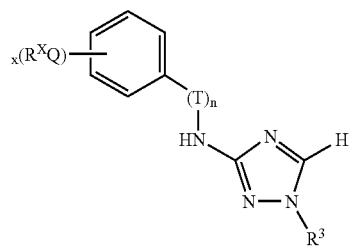
I-A

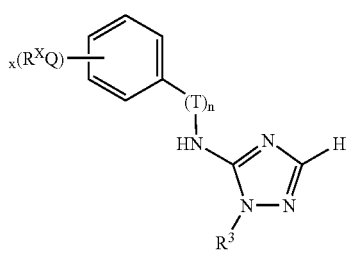
I-A' wherein x is 0-5 and n is 0 or 1.

In other embodiments, R² is —(T)$_n$Cy¹. In preferred embodiments, Cy¹ is selected from one of the following groups:

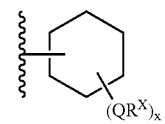
v

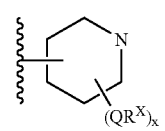
w

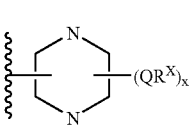
x

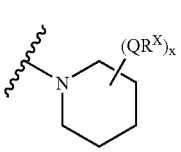
y

-continued

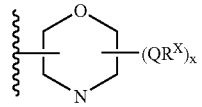
z

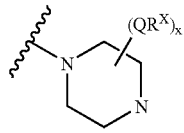
aa

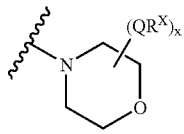
bb

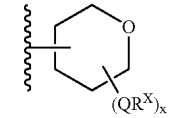
cc

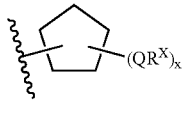
dd

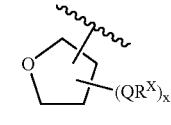
ee ff wherein Q and R$^X$ are as defined generally above and in classes and subclasses herein, x is 0-5, and n is 0 or 1.

In more preferred embodiments, Cy¹ is selected from one of the following groups:

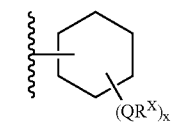
v

dd

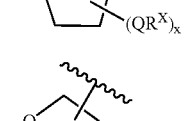
ee

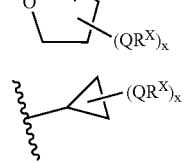
ff

In most preferred embodiments $R^1$ is hydrogen; $Cy^1$ is optionally substituted cyclohexyl (v), tetrahydrofuranyl (ee) (preferably attached in the 2-position), or cyclopropyl (ff); and compounds have one of the following formulas I-B, I-C, I-D, I-B', I-C', or I-D':

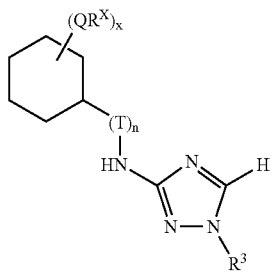

I-B

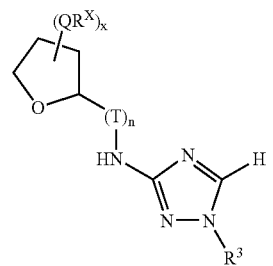

I-C

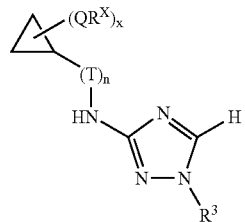

I-D

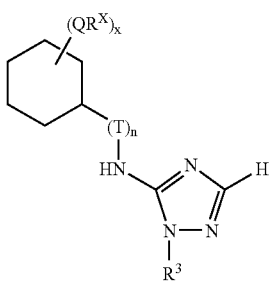

I-B'

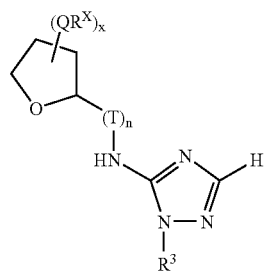

I-C'

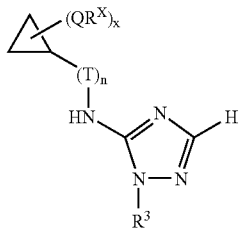

I-D'

In certain preferred embodiments, $R^1$ is hydrogen or $C_{1-4}$ alkyl. In most preferred embodiments, $R^1$ is hydrogen.

Preferred T groups, when present, include $CH_2$ or $-CH_2CH_2-$. In certain other preferred embodiments, n is 0 and T is absent.

As detailed above, $Ar^1$ or $Cy^1$ can be optionally substituted with up to 5 occurrences of $QR^X$. In certain preferred embodiments, x is 0-3, and thus $Ar^1$ or $Cy^1$ are each independently substituted with 0-3 occurrences of $QR^X$. In still other preferred embodiments, x is 0 and $Ar^1$ or $Cy^1$ are unsubstituted.

In preferred embodiments, $QR^X$ groups are each independently halogen, CN, $NO_2$, or an optionally substituted group selected from $C_{1-4}$ alkyl, aryl, aralkyl, $-N(R')_2$, $-CH_2N(R')_2$, $-OR'$, $-CH_2OR'$, $-SR'$, $-CH_2SR'$, $-COOR'$, $-NRCOR'$, $-CON(R')_2$, or $-SO_2N(R')_2$. In more preferred embodiments, $QR^X$ groups are each independently Cl, Br, F, $CF_3$, Me, Et, CN, $-COOH$, $-N(CH_3)_2$, $-N(Et)_2$, $-N(iPr)_2$, $-O(CH_2)_2OCH_3$, $-CONH_2$, $-COOCH_3$, $-OH$, $-CH_2OH$, $-NHCOCH_3$, $-SO_2NH_2$, methylenedioxy, ethylenedioxy, piperidinyl, piperizinyl, morpholino, or an optionally substituted group selected from $C_{1-4}$ alkoxy, phenyl, phenyloxy, benzyl, or benzyloxy. Most preferred $QR^X$ groups include those shown below in Table 1.

It will be appreciated that certain classes of compounds of general formula I are of special interest. In certain embodiments, the present invention provides monocyclic triazole compounds wherein compounds have the general formula II or II':

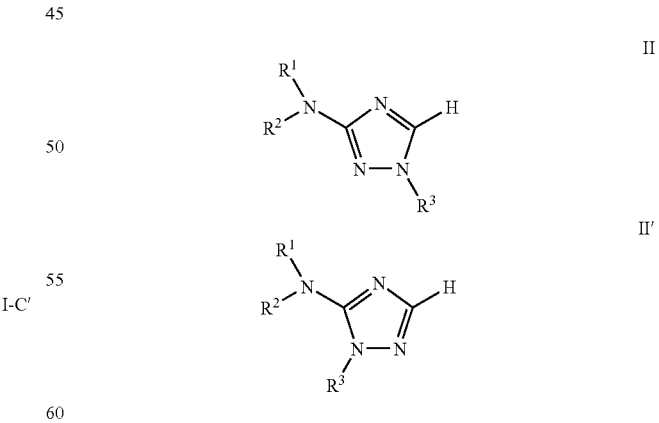

wherein $R^1$ and $R^2$ are defined generally above and in classes and subclasses herein;

$R^3$ is $-(L)_mR$, $-(L)_mAr^2$, or $-(L)_mCy^2$; L is an optionally substituted $C_{1-4}$ alkylidene chain wherein one methylene unit of L is optionally replaced by O, NR, NRCO, NRCONR, $NRCO_2$, CO, $CO_2$, CONR, OC(O)NR, $SO_2$, $SO_2NR$, NRSO$_2$, NRSO$_2$NR, C(O)C(O), or C(O)CH$_2$C(O); m is 0 or 1; Ar$^2$ is an optionally substituted aryl group selected from a 5-6 membered monocyclic or an 8-10 membered bicyclic ring having 0-5 heteroatoms independently selected from nitrogen, oxygen, or sulfur; and Cy$^2$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein Ar$^2$ and Cy$^2$ are each independently optionally substituted with up to five substituents selected from Z-R$^Y$; wherein Z is a bond or is a C$_{1-6}$ alkylidene chain wherein up to two non-adjacent methylene units of Z are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^Y$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

each occurrence of R is independently selected from hydrogen or an optionally substituted C$_{1-6}$ aliphatic group; and each occurrence of R' is independently selected from hydrogen or an optionally substituted group selected from C$_{1-8}$ aliphatic, C$_{6-10}$ aryl, a heteroaryl ring having 5-10 ring atoms, or a heterocyclyl ring having 3-10 ring atoms, or wherein R and R' taken together, or two occurrences of R' taken together, form a 5-8 membered cycloalkyl, heterocyclyl, aryl, or heteroaryl ring having 0-3 heteroatoms independently selected from nitrogen, oxygen, or sulfur.

As described generally above, in certain preferred embodiments, R$^2$ is —(T)$_n$Ar$^1$ and Ar$^1$ is selected from any one of a through u depicted above (including certain subsets such as b-i, b-ii, b-iii, c-i, c-ii, or c-iii), and in certain other embodiments, R$^2$ is —(T)$_n$Cy$^1$ and Cy$^1$ is selected from any one of v through ff depicted above. It will be appreciated, however, that for compounds of formula II or II' as described above, certain additional compounds are of special interest. For example, in certain exemplary embodiments, for compounds of general formula II or II' above, compounds of special interest include those compounds where R$^1$ is hydrogen; R$^2$ is —(T)$_n$Ar$^1$; Ar$^1$ is optionally substituted phenyl (a); R$^3$ is —(L)$_m$R, —(L)$_m$Ar$^2$, or (L)$_m$Cy$^2$; and compounds have the formula II-A-(i), II-A-(ii), II-A-(iii), II-A-(i)', II-A-(ii)', or II-A-(iii)':

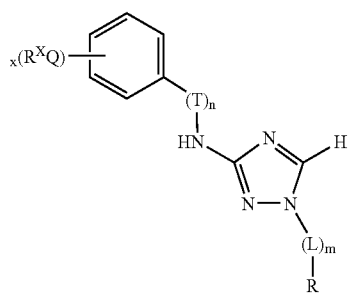

II-A-(i)

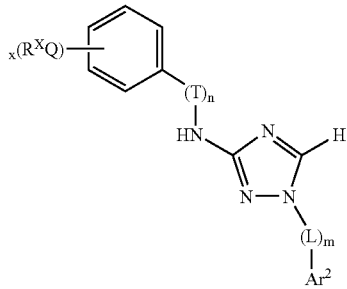

II-A-(ii)

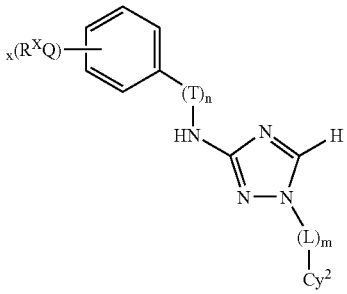

II-A-(iii)

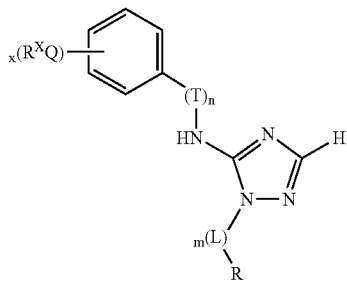

II-A-(i)'

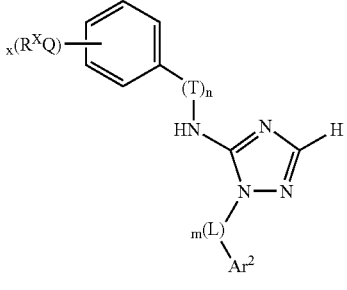

II-A-(ii)'

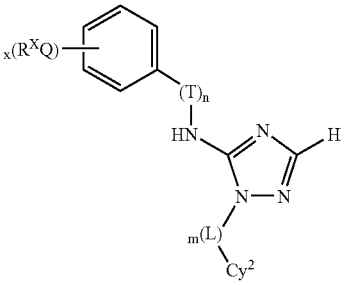

II-A-(iii)' wherein x is 0-5, n is 0 or 1, and m is 0 or 1.

In certain other exemplary embodiments, R$^1$ is hydrogen; R$^2$ is —(T)$_n$Cy$^1$; Cy$^1$ is optionally substituted cyclohexyl (v), tetrahydrofuranyl (ee) (preferably attached in the 2-position), or cyclopropyl (ff); R$^3$ is —(L)$_m$R, —(L)$_m$Ar$^2$, or (L)$_m$Cy$^2$; and compounds have one of the following formulas II-B-(i), II-B-(ii), II-B-(iii), II-C-(i), II-C-(ii), II-C-(iii), II-D-(i), II-D-(ii), II-D-(iii), II-B-(i)', II-B-(ii)', II-B-(iii)', II-C-(i)', II-C-(ii)', II-C-(iii)', II-D-(i)', II-D-(ii)', or II-D-(iii)':
II-B-(i)
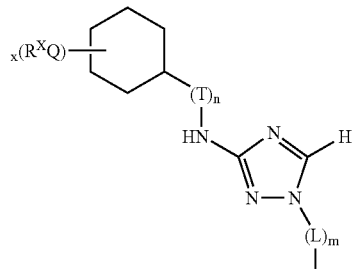
II-B-(ii)
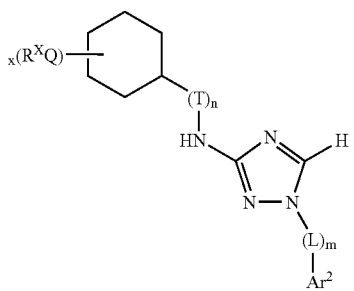
II-B-(iii)
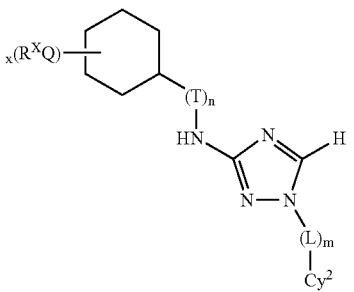
II-B-(i)'
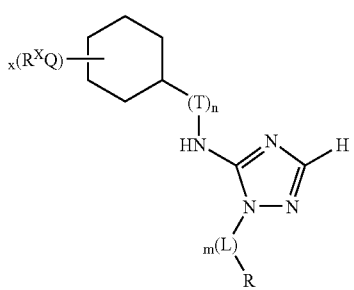
II-B-(ii)'
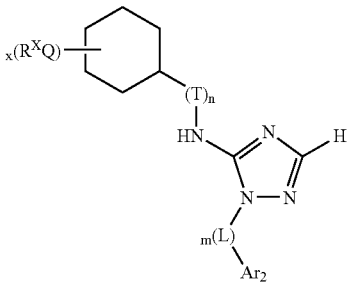
-continued
II-B-(iii)'
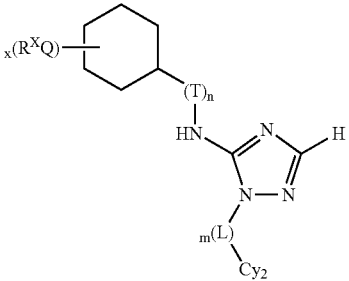
II-C-(i)
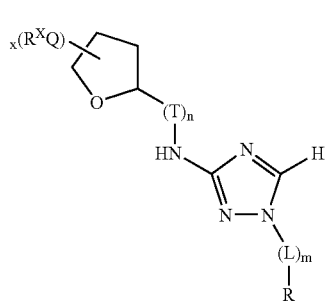
II-C-(ii)
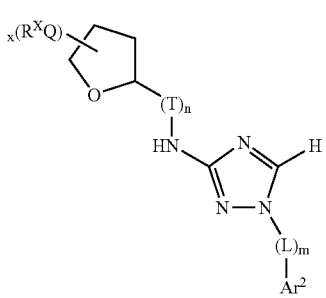
II-C-(iii)
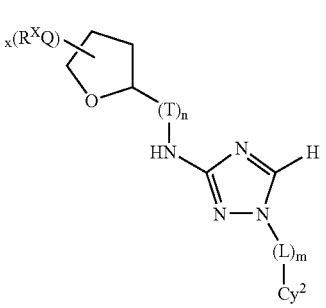
II-C-(i)'
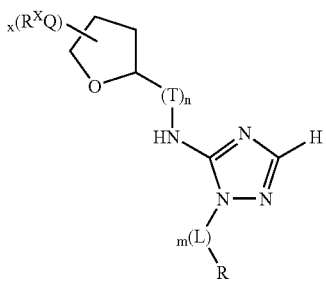

-continued

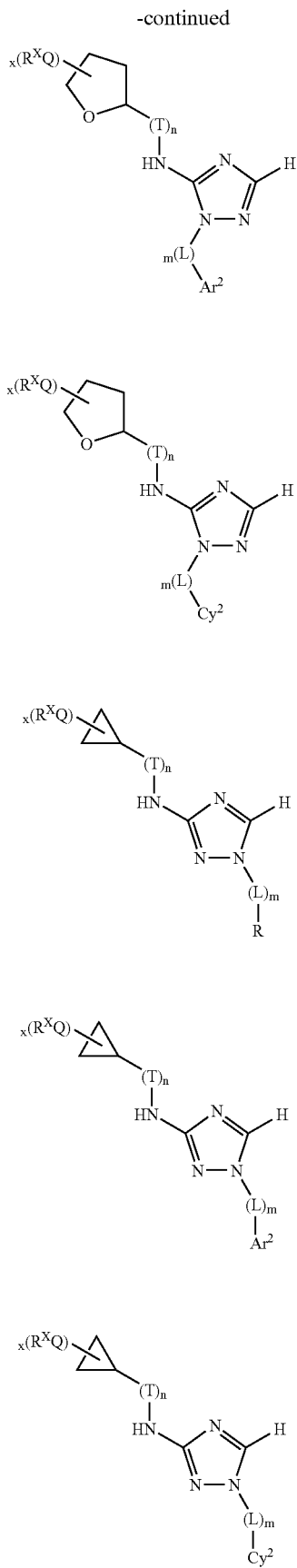

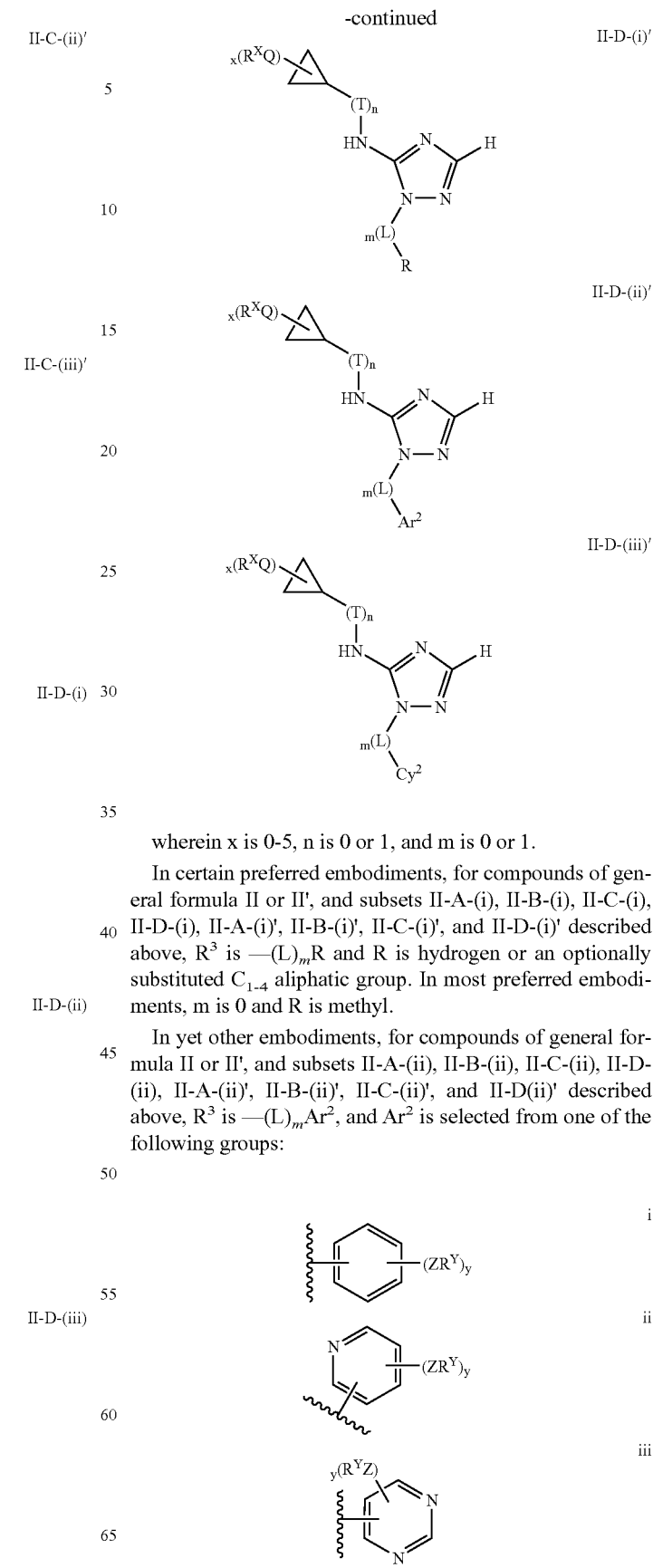

wherein x is 0-5, n is 0 or 1, and m is 0 or 1.

In certain preferred embodiments, for compounds of general formula II or II', and subsets II-A-(i), II-B-(i), II-C-(i), II-D-(i), II-A-(i)', II-B-(i)', II-C-(i)', and II-D-(i)' described above, $R^3$ is —(L)$_m$R and R is hydrogen or an optionally substituted $C_{1-4}$ aliphatic group. In most preferred embodiments, m is 0 and R is methyl.

In yet other embodiments, for compounds of general formula II or II', and subsets II-A-(ii), II-B-(ii), II-C-(ii), II-D-(ii), II-A-(ii)', II-B-(ii)', II-C-(ii)', and II-D(ii)' described above, $R^3$ is —(L)$_m$Ar$^2$, and Ar$^2$ is selected from one of the following groups:

-continued
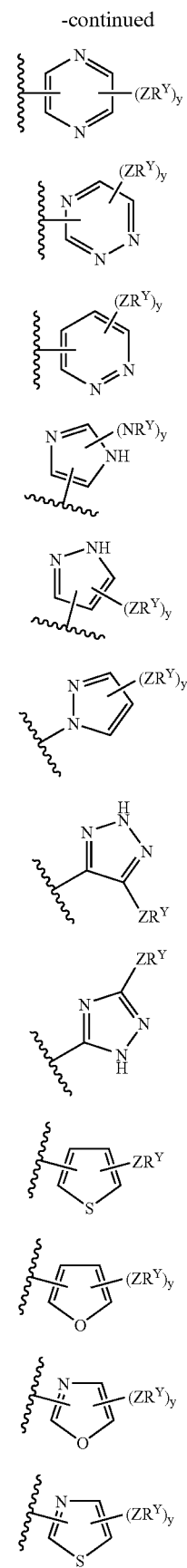
iv
v
vii
viii
ix
x
xi
xii
xiii
xiv
xv
xvi
-continued
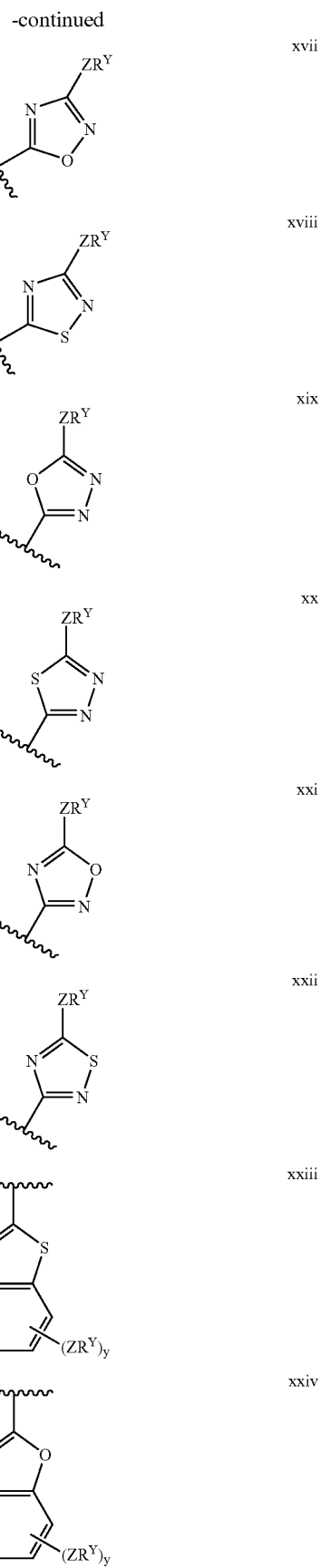
xvii
xviii
xix
xx
xxi
xxii
xxiii
xxiv -continued

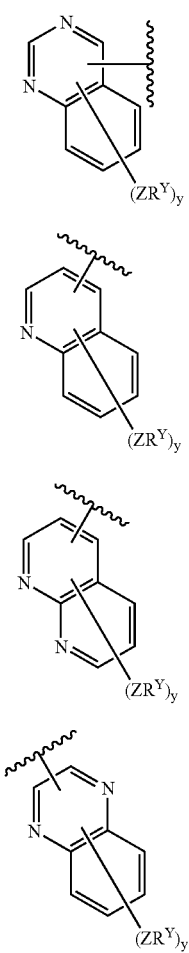

xxv xxvi xxvii xxviii wherein Z and $R^Y$ are as described generally above and in classes and subclasses herein and y is 0-5.

In more preferred embodiments, $Ar^2$ is selected from one of the following groups:

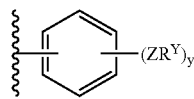

i

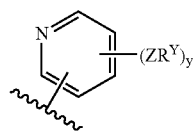

ii

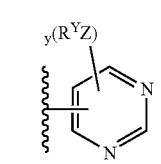

iii

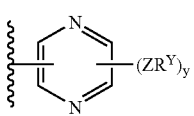

iv

-continued

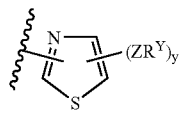

xvi

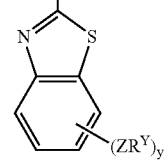

xxiii

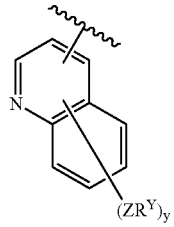

xxvi

In yet other embodiments, for compounds of general formula II or II', and subsets II-A-(iii) II-B-(iii) II-C-(iii) II-D-(iii) II-A-(iii)', II-B-(iii)', II-C-(iii)', and II-D-(iii)' described above, $R^3$ is —$(L)_m Cy^2$ and $Cy^2$ is selected from one of the following groups:

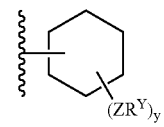

xxix

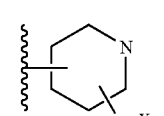

xxx

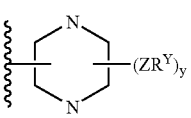

xxxi

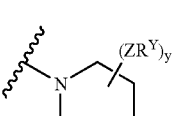

xxxii

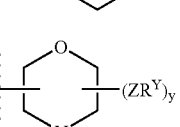

xxxiii

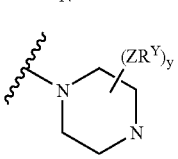

xxxiv

-continued

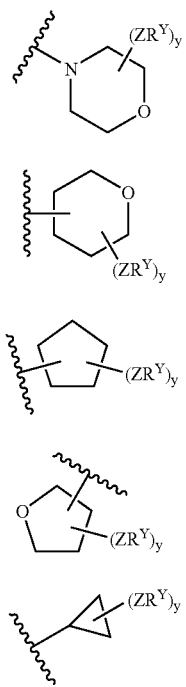

xxxv xxxvi xxxvii xxxviii xxxix wherein Z and $R^Y$ are as described generally above and in classes and subclasses herein and y is 0-5.

In more preferred embodiments, $Cy^2$ is selected from one of the following groups:

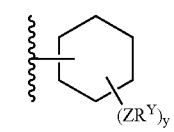

xxix xxxvii

In certain other preferred embodiments, for compounds of general formula II or II', $R^1$ is hydrogen; $R^2$ is as described generally above and in classes and subclasses herein; $R^3$ is —$(L)_m R$; m is 0; R is methyl; and compounds have one the following formulas II-E-(i), II-E-(ii), II-E-(i)', or II-E(ii)':

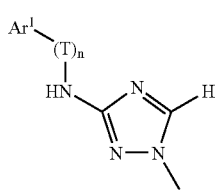

II-E-(i)

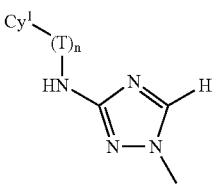

II-E-(ii)

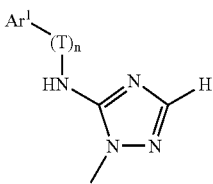

II-E-(i)'

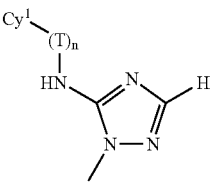

II-E-(ii)'

In certain other preferred embodiments, for compounds of general formula II or II', $R^1$ is hydrogen; $R^2$ is as described generally above and in classes and subclasses herein; $R^3$ is —$(L)_m Ar^2$, m is 0, and $Ar^2$ is optionally substituted phenyl (i), pyridyl (ii) (preferably attached in the 2-position), thiazolyl (xvi) (preferably attached in the 2-position), pyrimidinyl (iii) (preferably attached in the 2- or 4-position), or quinolinyl (xxvi) (preferably attached in the 2-position), and compounds have one of the following formulas II-F-(i), II-F-(ii), II-G-(i), II-G-(ii), II-H-(i), II-H-(ii), II-I-(i), II-I-(ii), II-J-(i), II-J-(ii), II-K-(i), II-K-(ii), II-E-(i)', II-E-(ii)', II-F-(i)', II-F-(ii)', II-G-(i)', II-G-(ii)', II-H-(i)', II-H-(ii)', II-I-(i)', II-I-(ii)', II-J-(i)', II-J-(ii)', II-K-(i)', or II-K-(ii)':

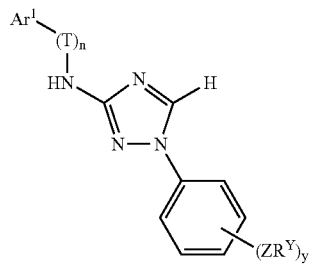

II-F-(i)

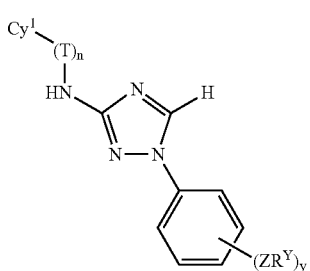

II-F-(ii)

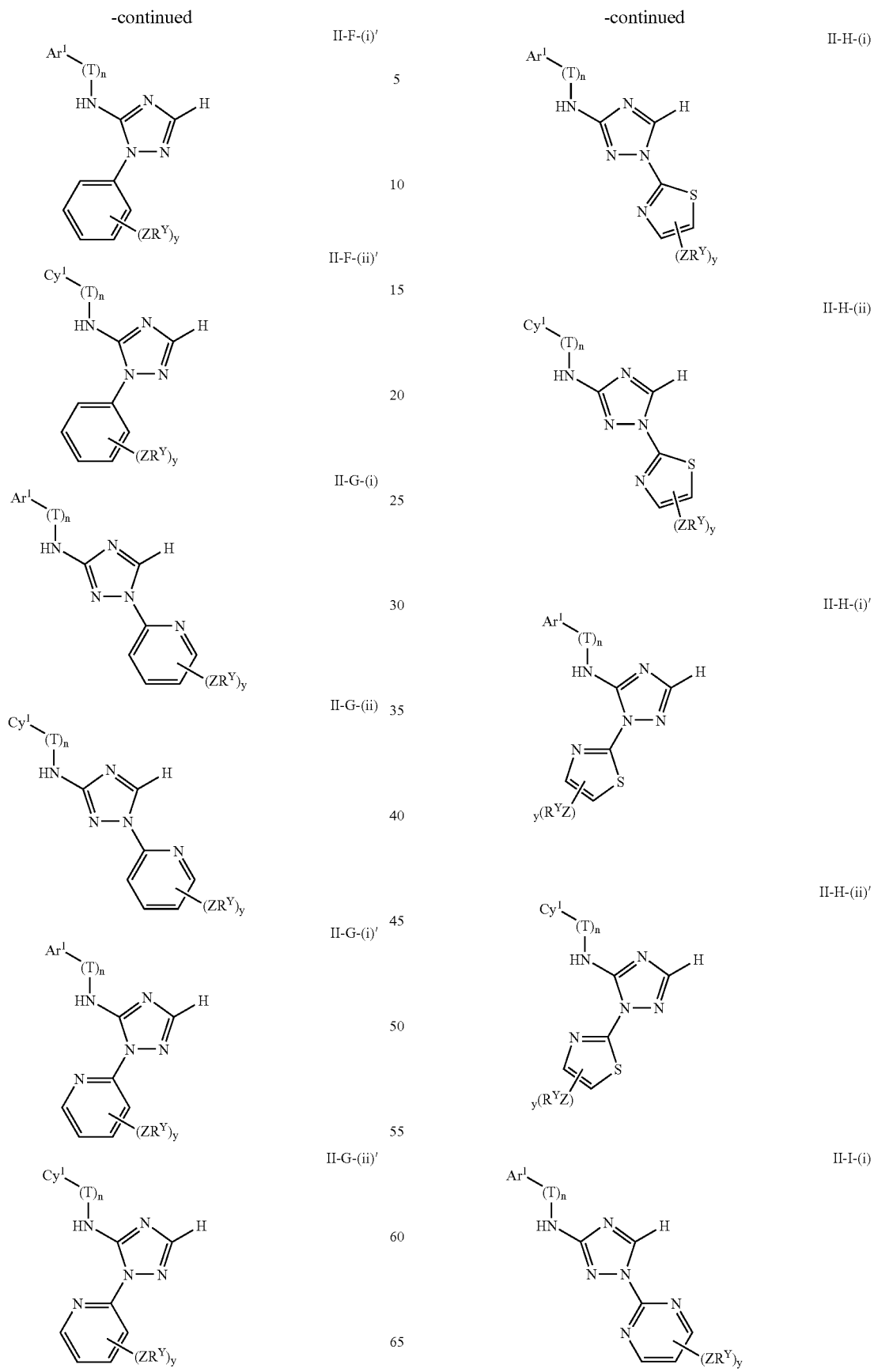

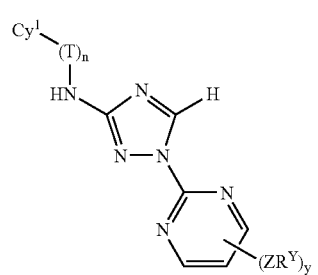
II-I-(ii)
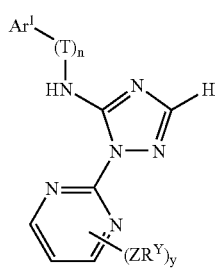
II-I-(i)'
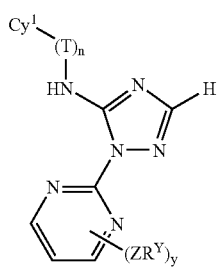
II-I-(ii)'
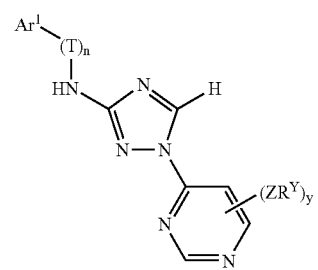
II-J-(i)
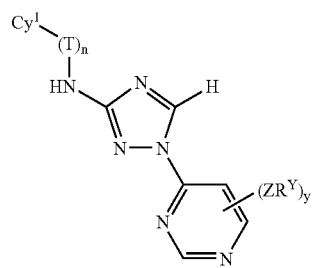
II-J-(ii)
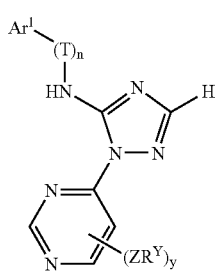
II-J-(i)'
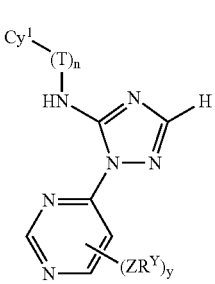
II-J-(ii)'
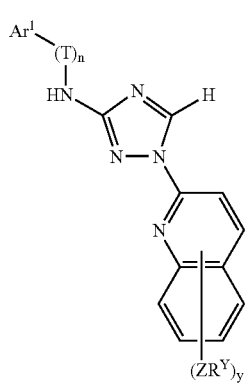
II-K-(i)
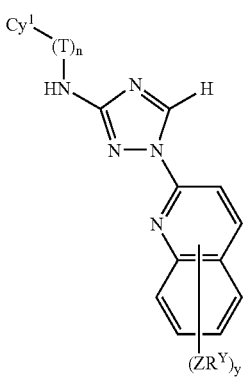
II-K-(ii)
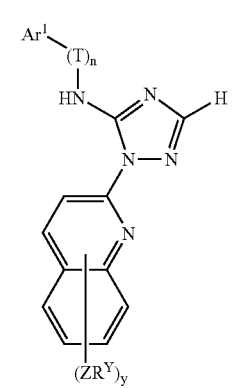
II-K-(i)'

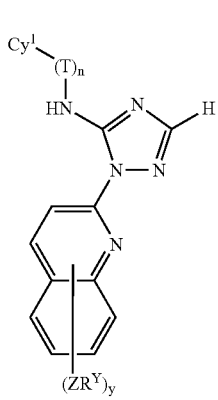

wherein y is 0-5 and n is 0 or 1.

In still other preferred embodiments, $R^1$ is hydrogen, $R^3$ is —$(L)_m Cy^2$, m is 0, and $Cy^2$ is optionally substituted cyclohexyl (xxix) and compounds have one the following formulas II-L-(i), II-L-(ii), II-L-(i)', or II-L-(ii)':

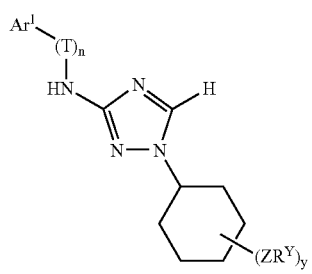

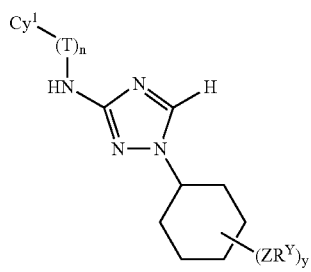

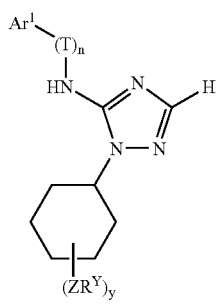

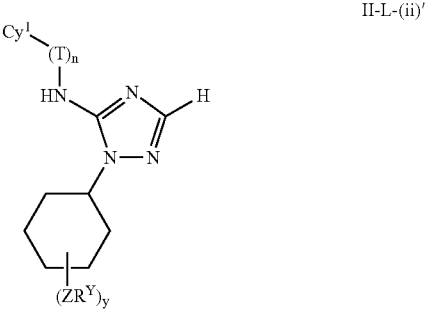

wherein y is 0-5 and n is 0 or 1.

As detailed above, $Ar^2$ or $Cy^2$ can be optionally substituted with up to 5 occurrences of $ZR^Y$. In certain preferred embodiments, y is 0-3 and thus $Ar^2$ or $Cy^2$ are each independently substituted with 0-3 occurrences of $ZR^Y$. In yet other preferred embodiments, y is 0 and $Ar^2$ or $Cy^2$ are unsubstituted.

In preferred embodiments, $ZR^Y$ groups are each independently halogen, CN, $NO_2$, or an optionally substituted group selected from $C_{1-4}$ alkyl, aryl, aralkyl, —$N(R')_2$, —$CH_2N(R')_2$, —OR', —$CH_2OR'$, —SR', —$CH_2SR'$, —COOR', —NRCOR', —$CON(R')_2$, or —$SO_2N(R')_2$. In more preferred embodiments, $ZR^Y$ groups are each independently Cl, Br, F, $CF_3$, Me, Et, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, methylenedioxy, ethylenedioxy, piperidinyl, piperizinyl, morpholino, or an optionally substituted group selected from $C_{1-4}$ alkoxy, phenyl, phenyloxy, benzyl, or benzyloxy. Most preferred $ZR^Y$ groups include those shown below in Table 1.

It will be appreciated that certain subclasses of the foregoing compounds are of particular interest.

For example, in certain preferred embodiments, for compounds of formulas II-A-(ii), II-A-(iii), II-B-(ii), II-B-(iii), II-C-(ii), II-C-(iii), II-D-(ii), II-D-(iii), II-A-(ii)', II-A-(iii)', II-B-(ii)', II-B-(iii)', II-C-(ii)', II-C-(iii)', II-D-(ii)', or II-D-(iii)', $R^3$ is —$(L)_m Ar^2$ and $Ar^2$ is phenyl (i), pyridyl (ii), pyrimidinyl (iii), thiazolyl (xvi), or quinolinyl (xxvi), each optionally substituted with 0-3 occurrences of $ZR^Y$; or $R^3$ is —$(L)_m Cy^2$ and $Cy^2$ is cyclohexyl (xxix), optionally substituted with 0-3 occurrences of $ZR^Y$. In more preferred embodiments for compounds described above, n is 0, or n is 1 and T is $CH_2$; m is 0; x is 0-3; y is 0-3; and each occurrence of $QR^X$ or $ZR^Y$ is independently halogen, CN, $NO_2$, or an optionally substituted group selected from $C_{1-4}$ alkyl, aryl, aralkyl, —$N(R')_2$, —$CH_2N(R')_2$, —OR', —$CH_2OR'$, —SR', —$CH_2SR'$, —COOR', —NRCOR', —$CON(R')_2$, or —$SO_2N(R')_2$. In more preferred embodiments, $QR^X$ or $ZR^Y$ groups are each independently Cl, Br, F, $CF_3$, Me, Et, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, methylenedioxy, ethylenedioxy, piperidinyl, piperizinyl, morpholino, or an optionally substituted group selected from $C_{1-4}$ alkoxy, phenyl, phenyloxy, benzyl, or benzyloxy.

For compounds of formulas II-E-(i), II-E-(ii), II-F-(i), II-F-(ii), II-G-(i), II-G-(ii), II-H-(i), II-H-(ii), II-I-(i), II-I-(ii), II-J-(i), II-J-(ii), II-K-(i), II-K-(ii), II-E-(i)', II-E-(ii)', II-F-(i)', II-F-(ii)', II-G-(i)', II-G-(ii)', II-H-(i)', II-H-(ii)', II-I-(i)', II-I-(ii)', II-J-(i)', II-J-(ii)', II-K-(i)', II-K-(ii)', II-L-(i)', or II-L-(ii)', $R^2$ is —$(T)_n Ar^1$ and $Ar^1$ is phenyl (a), optionally substituted with 0-3 occurrences of $QR^X$; or $R^2$ is —$(T)_n Cy^1$ and Cy¹ is selected from cyclohexyl (v), tetrahydrofuranyl (ee), or cyclopropyl (ff), optionally substituted with 0-3 occurrences of $QR^X$. In more preferred embodiments for compounds described above, n is 0, or n is 1 and T is $CH_2$; m is 0; x is 0-3; y is 0-3; and each occurrence of $QR^X$ or $ZR^Y$ is independently halogen, CN, $NO_2$, or an optionally substituted group selected from $C_{1-4}$ alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, or —SO$_2$N(R')$_2$. In more preferred embodiments, $QR^X$ or $ZR^Y$ groups are each independently Cl, Br, F, $CF_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, methylenedioxy, ethylenedioxy, piperidinyl, piperizinyl, morpholino, or an optionally substituted group selected from $C_{1-4}$ alkoxy, phenyl, phenyloxy, benzyl, or benzyloxy.

Certain other classes of special interest for compounds of formula I include bicyclic triazole compounds wherein compounds have the general formula II':

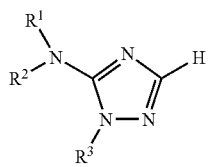

II' wherein R¹ is as defined generally above and in classes and subclasses herein;

wherein R² and R³, taken together form an optionally substituted group selected from a 5-7-membered saturated, partially unsaturated, or fully unsaturated monocyclic ring having 0-3 heteroatoms independently selected from nitrogen, oxygen, or sulfur, or an 8-10-membered saturated, partially unsaturated, or fully unsaturated bicyclic ring system having 0-3 heteroatoms independently selected from nitrogen, oxygen, or sulfur;

wherein a ring formed by R² and R³ taken together, is optionally substituted with 0-5 independent occurrences of $W—R^W$; wherein each independent occurrence of W is a bond or is a $C_{1-6}$ alkylidene chain wherein up to two non-adjacent methylene units of W are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^W$ is independently selected from R', halogen, $NO_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; and each occurrence of R is independently selected from hydrogen or an optionally substituted $C_{1-6}$ aliphatic group; and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together, or two occurrences of R' taken together, form a 5-8 membered cycloalkyl, heterocyclyl, aryl, or heteroaryl ring having 0-3 heteroatoms independently selected from nitrogen, oxygen, or sulfur.

In certain preferred embodiments, compounds having one of the following formulas: II-M', II-N', II-O', II-P', II-Q', II-R', II-S', II-T', II-U', II-V' or II-W':

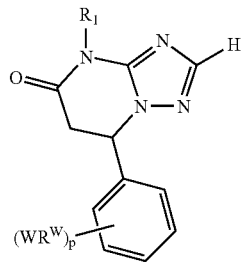

II-M'

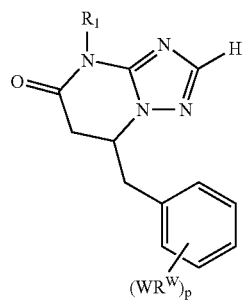

II-N'

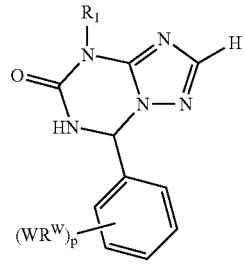

II-O'

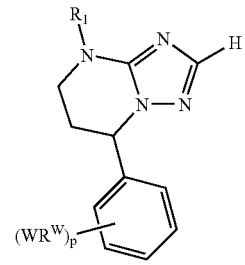

II-P'

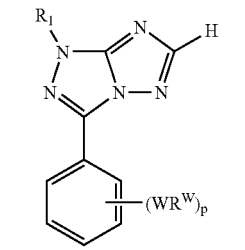

II-Q'

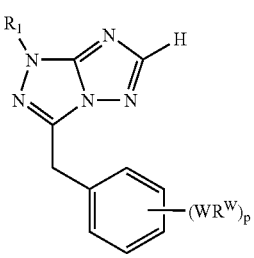

II-R'

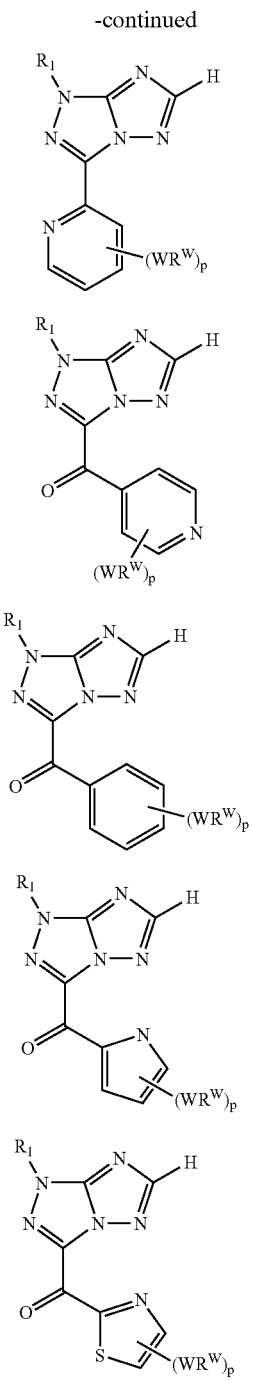

wherein W and $R^W$ are as described generally above and in classes and subclasses herein and p is 0-5.

As detailed above, any ring formed by $R^2$ and $R^3$ taken together can be optionally substituted with up to 5 occurrences of $WR^W$. In certain preferred embodiments, p is 0-3. In still other preferred embodiments, p is 0 and the ring formed by $R^2$ and $R^3$ is unsubstituted.

In preferred embodiments, $WR^W$ groups are each independently halogen, CN, $NO_2$, or an optionally substituted group selected from $C_{1-4}$ alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$. In more preferred embodiments, $WR^W$ groups are each independently Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, methylenedioxy, ethylenedioxy, piperidinyl, piperizinyl, morpholino, or an optionally substituted group selected from $C_{1-4}$ alkoxy, phenyl, phenyloxy, benzyl, or benzyloxy. Most preferred $WR^W$ groups include those shown below in Table 1.

In other preferred embodiments, $R^1$ is hydrogen or $C_{1-4}$ alkyl. In more preferred embodiments, $R^1$ is hydrogen or methyl. In most preferred embodiments, $R^1$ is hydrogen.

Another embodiment of this invention provides a compound having the general formula II:

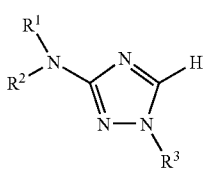

II wherein $R^3$ is —(L)$_m$R, —(L)$_m$Ar$^2$, or —(L)$_m$Cy$^2$; L is an optionally substituted $C_{1-4}$ alkylidene chain wherein one methylene unit of L is optionally replaced by O, NR, NRCO, NRCONR, NRCO$_2$, CO, CO$_2$, CONR, OC(O)NR, SO$_2$, SO$_2$NR, NRSO$_2$, NRSO$_2$NR, C(O)C(O), or C(O)CH$_2$C(O); m is 0 or 1; Ar$^2$ is an optionally substituted aryl group selected from a 5-6 membered monocyclic or an 8-10 membered bicyclic ring having 0-5 heteroatoms independently selected from nitrogen, oxygen, or sulfur; and Cy$^2$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein Ar$^2$ and Cy$^2$ are each independently optionally substituted with up to five substituents selected from Z-R$^Y$; wherein Z is a bond or is a $C_{1-6}$ alkylidene chain wherein up to two non-adjacent methylene units of Z are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^Y$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; and the other variables are as defined herein. More specific forms of this embodiment are as defined in any of the embodiments herein.

In certain of these more specific forms, $R^1$ is hydrogen or $C_{1-4}$ alkyl. In other embodiments, $R^1$ is hydrogen.

In certain embodiments, $R^3$ is —(L)$_m$Ar$^2$ and Ar$^2$ is as defined herein. In more specific embodiments, Ar$^2$ is selected from one of the following groups:

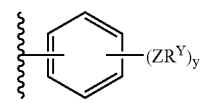

i

-continued

-continued
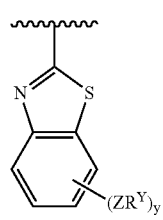
xxiii
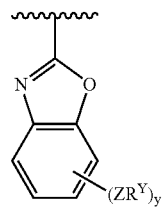
xxiv
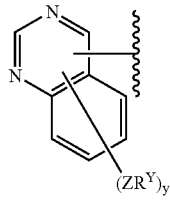
xxv
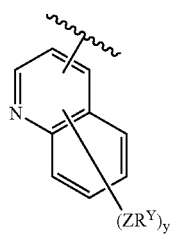
xxvi
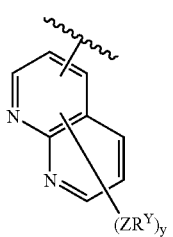
xxvii
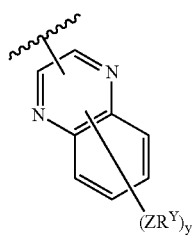
xxviii
wherein y is 0-5.
In other embodiments, Ar² is selected from one of the following groups:
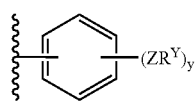
i
-continued
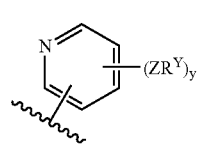
ii
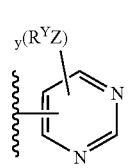
iii
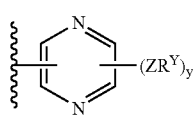
iv
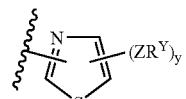
xvi
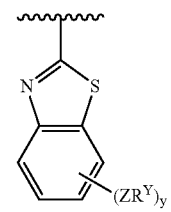
xxiii
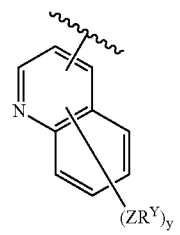
xxvi
In still other embodiments, Ar² is selected from one of the following groups:
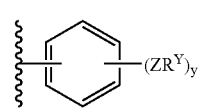
i
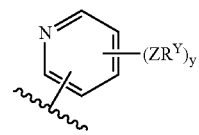
ii
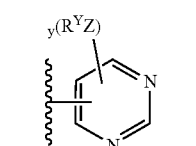
iii
Specific forms of any embodiments of this invention, include those wherein Ar² is:

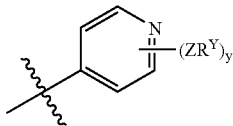

Other specific forms of any embodiments of this invention, include those wherein Ar² is:

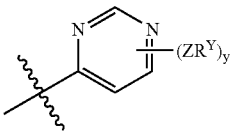

Even more specific forms are those wherein Ar² is

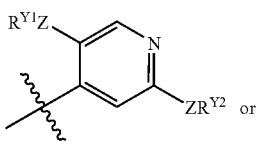

or

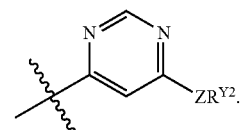

The embodiments of this invention may be combined to provide compounds wherein R¹ is hydrogen; R² is —(T)$_n$Ar¹; n is 0 or 1; R³ is —(L)$_m$Ar²; m is 0; Ar² is optionally substituted phenyl (i), pyridyl (ii), pyrimidinyl (iii) (preferably attached in the 2- or 4-position); and the compounds have one of the following formulas II-F-(i), 1-G-(i), II-J-(i), or II-X-(i):

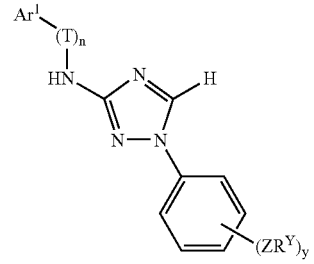

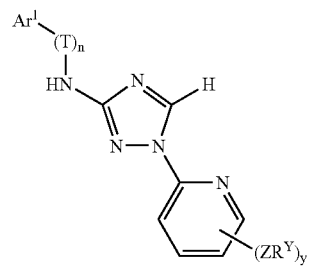

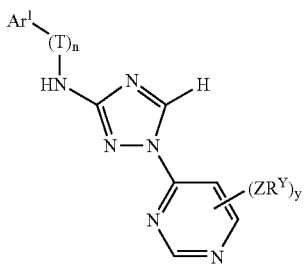

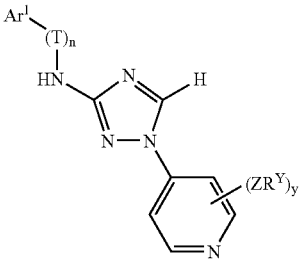

wherein y is 0-5.

Another embodiment provides a compound wherein R¹ is hydrogen; R² is —(T)$_n$Ar¹; n is 0 or 1; R³ is —(L)$_m$Ar²; m is 0; Ar² is optionally substituted pyridyl (ii) (preferably attached in the 2-position); and the compound has the following formula II-X-(i):

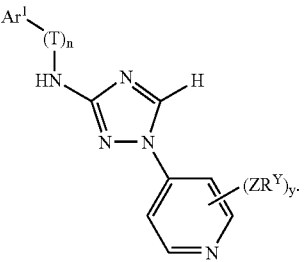

Another embodiment provides a compound wherein R¹ is hydrogen; R² is —(T)$_n$Ar¹; n is 0 or 1; R³ is —(L)$_m$Ar²; m is 0; Ar² is optionally substituted pyrimidinyl (iii) (preferably attached in the 2- or 4-position); and compounds have one of the following formulas II-J-(i):

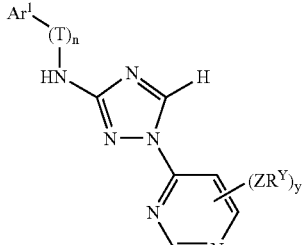

Another embodiment provides a compound wherein R¹ is hydrogen; R² is —(T)$_n$Ar¹; n is 0 or 1; R³ is —(L)$_m$Ar²; m is 0; Ar² is optionally substituted pyridyl (ii) (preferably attached in the 2-position); and compounds have one of the following formulas II-X-(i):

II-X-(i)-(a)
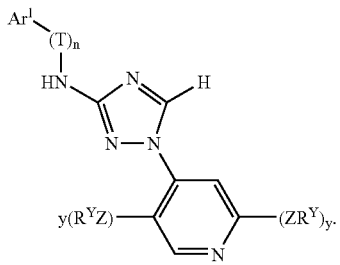

Another embodiment provides a compound wherein R¹ is hydrogen; R² is —(T)$_n$Ar¹; n is 0 or 1; R³ is —(L)$_m$Ar²; m is 0; Ar² is optionally substituted pyrimidinyl (iii) (preferably attached in the 2- or 4-position); and compounds have one of the following formulas II-J-(i):

II-J-(i)-(a)
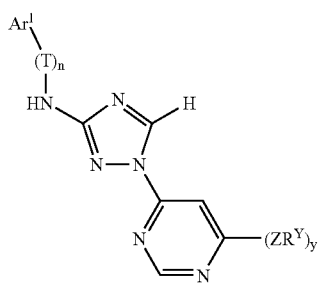

Another embodiment provides a compound wherein R³ is —(L)$_m$Ar² and Ar² is phenyl (i), pyridyl (ii), pyrimidinyl (iii), thiazolyl (xvi), or quinolinyl (xxvi), each optionally substituted with 0-3 occurrences of ZR$^Y$.

This invention also provides compounds wherein R² is —(T)$_n$Ar¹. It should be recognized that this embodiment of R² may be combined with any other embodiment herein. In certain forms of this embodiment, Ar¹ is an aromatic ring (e.g., phenyl optionally substituted with up to 5 QR$^X$ groups). In other forms, Ar¹ is optionally substituted heteroaromatic (where the maximum number of QR$^X$ groups varies with, e.g., ring size).

In one embodiment of this invention wherein R² is —(T)$_n$Ar¹, Ar¹ is selected from the following groups:

a
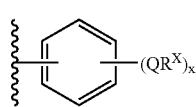

b
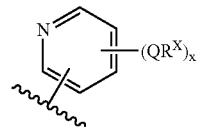

-continued c
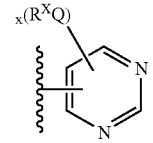

d
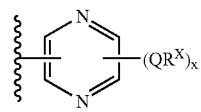

e
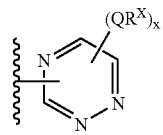

f
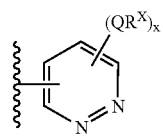

g
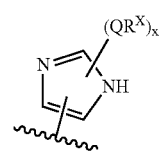

h
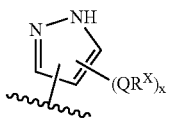

i
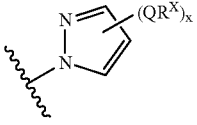

j
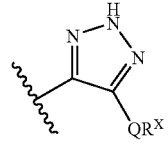

k
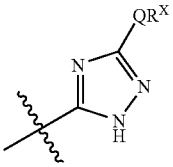

l
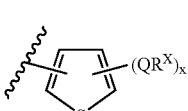

m
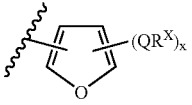

-continued n 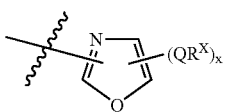

o 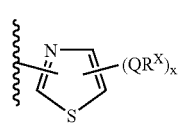

p 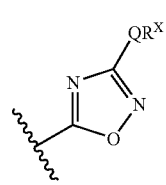

q 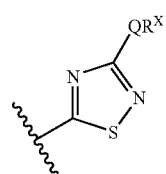

r 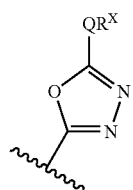

s 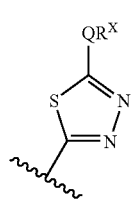

t 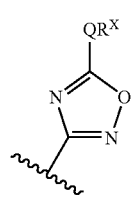

u 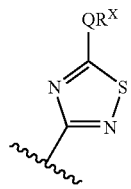

wherein x is 0-5.

Alternatively, $Ar^1$ is selected from one of the following groups:

a 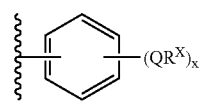

b-i 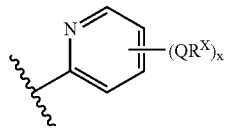

c-i 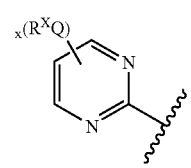

d 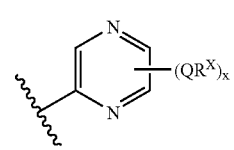

b-ii 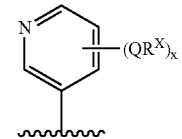

b-iii 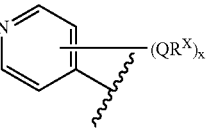

c-ii 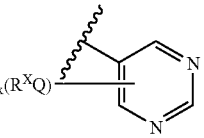

c-iii 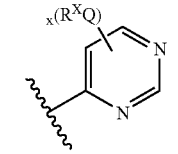

In certain embodiments, this invention also provides a compound wherein $R^1$ is hydrogen; $R^2$ is $—(T)_n Ar^1$; $Ar^1$ is an optionally substituted heteroaromatic or an optionally substituted phenyl (a). Compounds wherein $Ar^1$ is an optionally substituted phenyl, have the formula I-A:

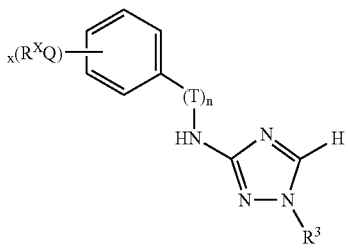

I-A wherein x is 0-5 and n is 0 or 1.

In a specific form of this embodiment, $R^1$ is hydrogen; $R^2$ is —$(T)_n Ar^1$; $Ar^1$ is optionally substituted heteroaryl or an optionally substituted phenyl (a); $R^3$ is —$(L)_m Ar^2$. Compounds wherein $Ar^1$ is an optionally substituted phenyl, have the following formula I-A-(ii):

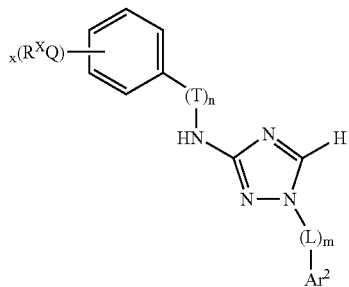

II-A-(ii)

wherein x is 0-5, n is 0 or 1, and m is 0 or 1.

In compounds comprising $Ar^1$, x may be any number up to the maximum allowed substitutions on an $Ar^1$ (e.g., up to 5 if $Ar^1$ is phenyl). In preferred embodiments, x is 0, 1, 2, or 3. In certain embodiments, x is 1.

In certain embodiments compounds are provided wherein $R^1$ is hydrogen; $R^2$ is —$(T)_n Ar^1$; n is 0; $Ar^1$ is optionally substituted phenyl (a); and the compounds have the formula I-A-a (wherein $R^3$ is as defined herein):

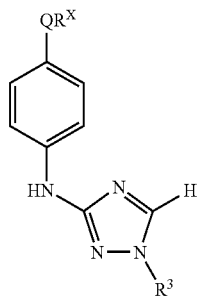

I-A-a

Certain embodiments of this invention provide compounds comprising a $QR^X$ group. In certain forms of these embodiments, the $QR^X$ groups are each independently halogen, CN, $NO_2$, or an optionally substituted group selected from $C_{1-4}$ alkyl, aryl, aralkyl, —$N(R')_2$, —$CH_2 N(R')_2$, —OR', —$CH_2 OR'$, —SR', —$CH_2 SR'$, —COOR', —COR', —NRCOR', —NRCONRR', —NRCOOR', —$CON(R')_2$, or —$SO_2 N(R')_2$. In other forms, the $QR^X$ groups are each independently Cl, Br, F, $CF_3$, Me, Et, CN, —COOH, —$N(CH_3)_2$, —$N(Et)_2$, —$N(iPr)_2$, —$O(CH_2)_2 OCH_3$, —$CONH_2$, —$COOCH_3$, —OH, —$CH_2 OH$, —$NHCOCH_3$, —N(H)C(O)N(H)CH_3, —N(H)C(O)OCH_3, —N(H)C(O)N(H)Et, —N(H)C(O)OEt, —N(H)C(O)N(H)-iPr, —N(H)C(O)O-iPr, —N(H)C(O)N(H)-nPr, —N(H)C(O)O-nPr, —$SO_2 NH_2$, methylenedioxy, ethylenedioxy, piperidinyl, piperizinyl, morpholino, or an optionally substituted group selected from $C_{1-4}$ alkoxy, phenyl, phenyloxy, benzyl, or benzyloxy. In still other forms, the $QR^X$ groups are —$N(R')_2$, —NRR', —$N(R)_2$, —NRCOR', —NRCONRR', —NRCOOR', piperidinyl, piperizinyl, or morpholino, wherein the piperidinyl, piperizinyl, morpholino is optionally substituted with —COR', —COOR', —$CON(R')_2$, or —$SO_2 N(R')_2$. In these embodiments, R in $QR^X$ is H and R' in $QR^X$ is $C_{1-6}$ alkyl.

More specific forms of $QR^X$ are also provided by this invention:

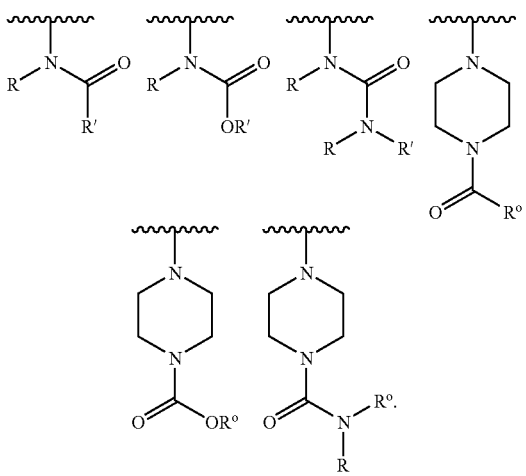

In even more specific forms, R is H and each R' and $R^o$ is selected from $C_{1-6}$ alkyl.

In another embodiment, $QR^X$ is H.

In a specific form of this invention, $R^1$ is hydrogen; $R^2$ is —$(T)_n Ar^1$; n is 0 or 1; $R^3$ is —$(L)_m Ar^2$; m is 0; $Ar^2$ is optionally substituted pyridinyl (ii) (preferably attached in the 2- or 4-position); and compounds have the formula III-A:

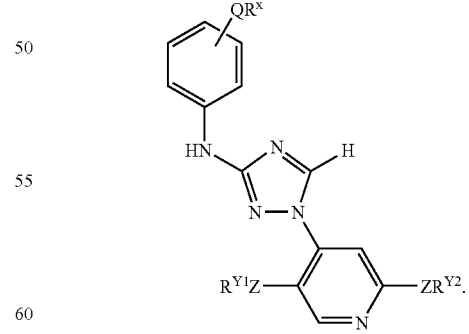

III-A

In another specific form of this invention, $R^1$ is hydrogen; $R^2$ is —$(T)_n Ar^1$; n is 0 or 1; $R^3$ is —$(L)_m Ar^2$; m is 0; $Ar^2$ is optionally substituted pyrimidinyl (iii) (preferably attached in the 2- or 4-position); and compounds have the following formula III-B:

III-B

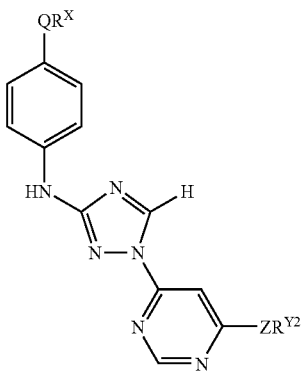

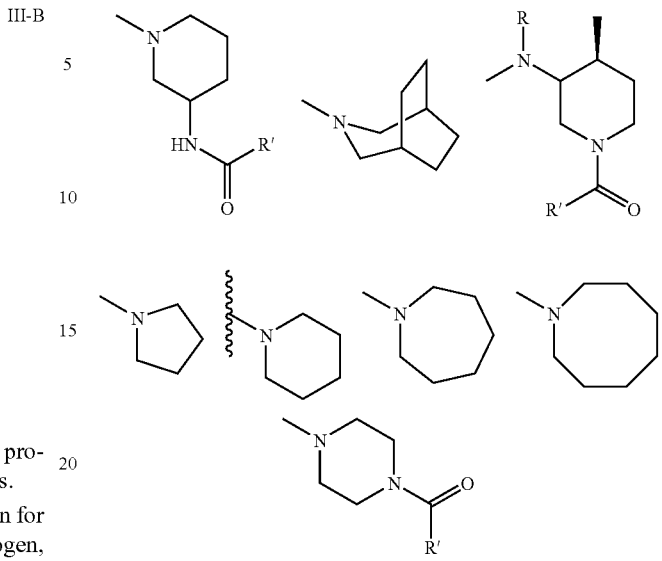

Accordingly, certain embodiments of this invention provide compounds comprising $ZR^Y$, $ZR^{Y1}$, or $ZR^{Y2}$ groups.

In any of these embodiments, $ZR^{Y1}$ is as defined herein for $ZR^Y$. In a preferred embodiment, $ZR^{Y1}$ is hydrogen, halogen, $C_{1-6}$ alkyl, $C_{1-4}$ alkoxy, CN, or $NO_2$. In more preferred embodiments, $ZR^{Y1}$ is hydrogen, halogen, methyl, or ethyl.

In any of these embodiments, $ZR^{Y2}$ is also as defined herein for $ZR^Y$. In a preferred embodiment, $ZR^{Y2}$ is halogen, $C_{1-6}$ alkyl, CN, $NO_2$, or an optionally substituted group selected from $C_{1-4}$ alkyl, aryl, aralkyl, —N(R')$_2$, —CH$_2$N(R')$_2$, —OR', —CH$_2$OR', —SR', —CH$_2$SR', —COOR', —COR', —NRCOR', —NRCONRR', —NRCOOR', —CON(R')$_2$, or —SO$_2$N(R')$_2$. In a more preferred embodiment, $ZR^{Y2}$ is —N(R)$_2$, —N(R')$_2$, or —NRR', wherein R is H or $C_{1-6}$ alkyl and R' is $C_{1-6}$ alkyl, wherein the $C_{1-6}$ alkyl is optionally substituted with halo, CN, OH, or —OC$_{1-6}$ alkyl. In other embodiments, $ZR^{Y2}$ is —N(R')$_2$, where each occurrences of R' taken together, forms a 5-10 membered heterocyclic ring having 1-3 heteroatoms independently selected from nitrogen, oxygen, or sulfur, wherein the heterocyclic ring is optionally substituted with halo, $C_{1-6}$ alkyl, —COR', —COOR', —CON(R')$_2$, —NRCOR', —NRCOOR', —NRCONRR', or —SO$_2$N(R')$_2$, where each occurrence of R is hydrogen or $C_{1-6}$ alkyl and each occurrence of R' is $C_{1-6}$ alkyl.

In more specific embodiments, $ZR^{Y2}$ is:

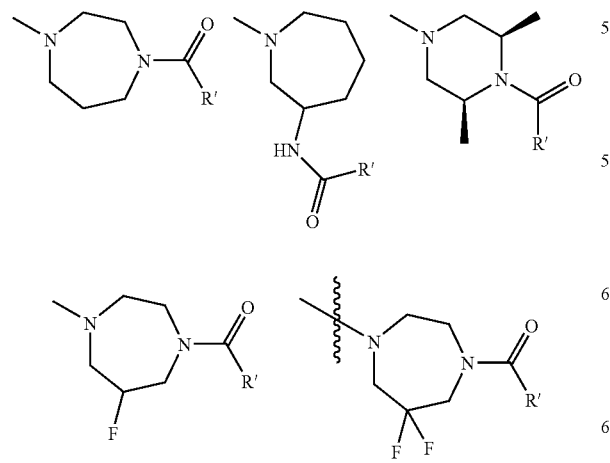

wherein R' is $C_{1-8}$ alkyl, wherein the alkyl is optionally substituted with halo, CN, OH, or —OC$_{1-6}$ alkyl; and wherein any ring is optionally substituted with aryl, heterocyclic, heteroaryl, $C_{1-6}$ alkyl, wherein each aryl, heterocyclic, heteroaryl, $C_{1-6}$ alkyl is optionally substituted with halo, CN, $C_{1-6}$ alkyl, OH, or —OC$_{1-6}$ alkyl.

In certain embodiments, $ZR^{Y2}$ is:

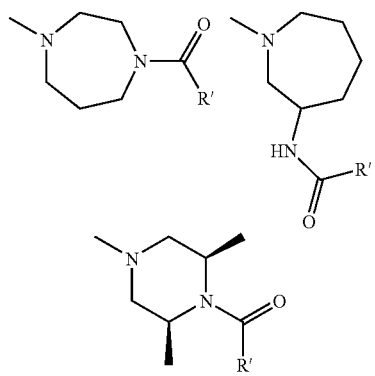

wherein R' is $C_{1-8}$ alkyl, wherein the alkyl is optionally substituted with halo, CN, OH, or —OC$_{1-6}$ alkyl; and wherein any ring is optionally substituted with aryl, heterocyclic, heteroaryl, $C_{1-6}$ alkyl, wherein each aryl, heterocyclic, heteroaryl, $C_{1-6}$ alkyl is optionally substituted with halo, CN, $C_{1-6}$ alkyl, OH, or —OC$_{1-6}$ alkyl.

In preferred embodiments, R, in $ZR^{Y1}$ or $ZR^{Y2}$, is hydrogen.

In a preferred embodiment, compounds of this invention are those wherein n is 0. In other preferred embodiments, compounds of this invention are those wherein m is 0.

Representative examples of compounds of formula I are set forth below in Table 1.

TABLE 1
Examples of Compounds of Formula I:
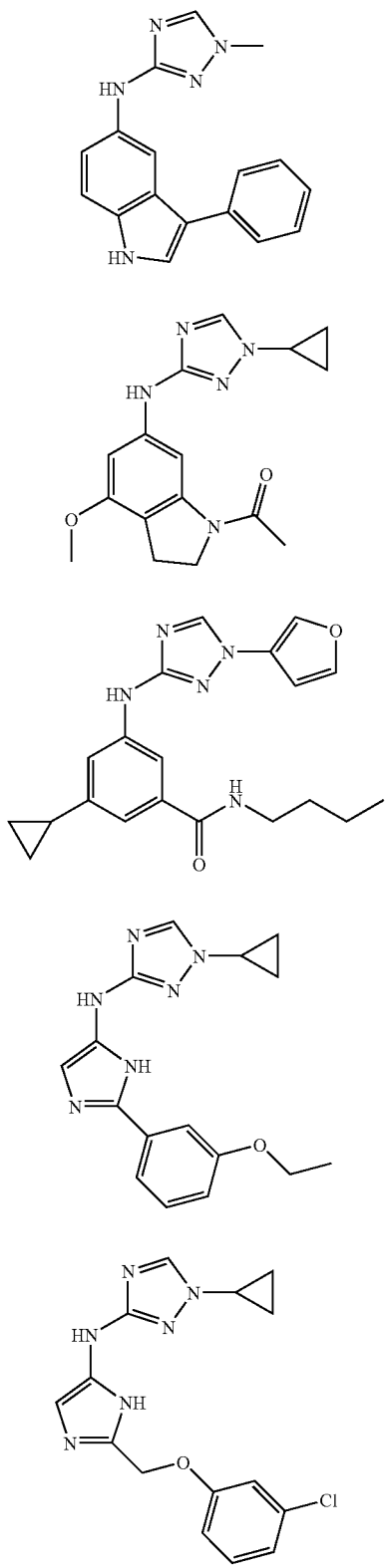
TABLE 1-continued
Examples of Compounds of Formula I:
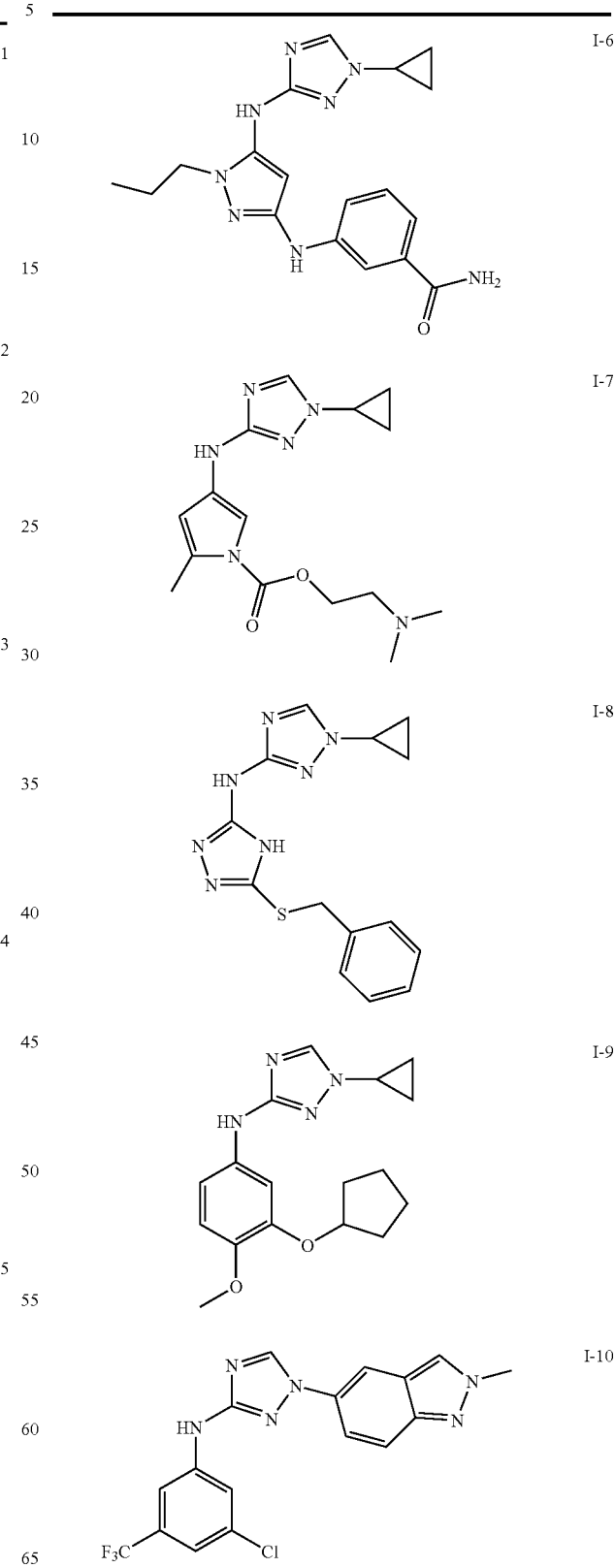

TABLE 1-continued
Examples of Compounds of Formula I:
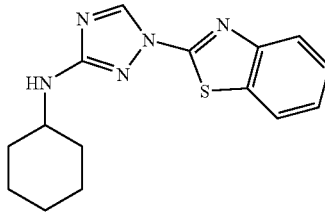
I-11
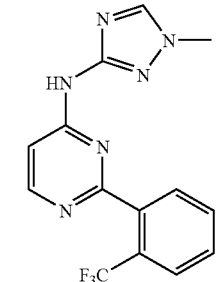
I-12
I-13
I-14
I-15
I-16
TABLE 1-continued
Examples of Compounds of Formula I:
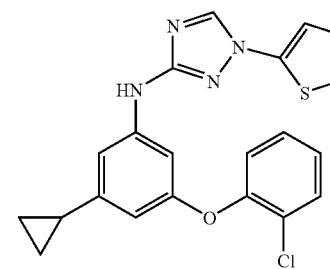
I-17
I-18
I-19
I-20
I-21
I-22

TABLE 1-continued

Examples of Compounds of Formula I:

I-23, I-24, I-25, I-26, I-27, I-28, I-29, I-30, I-31, I-32

TABLE 1-continued
Examples of Compounds of Formula I:
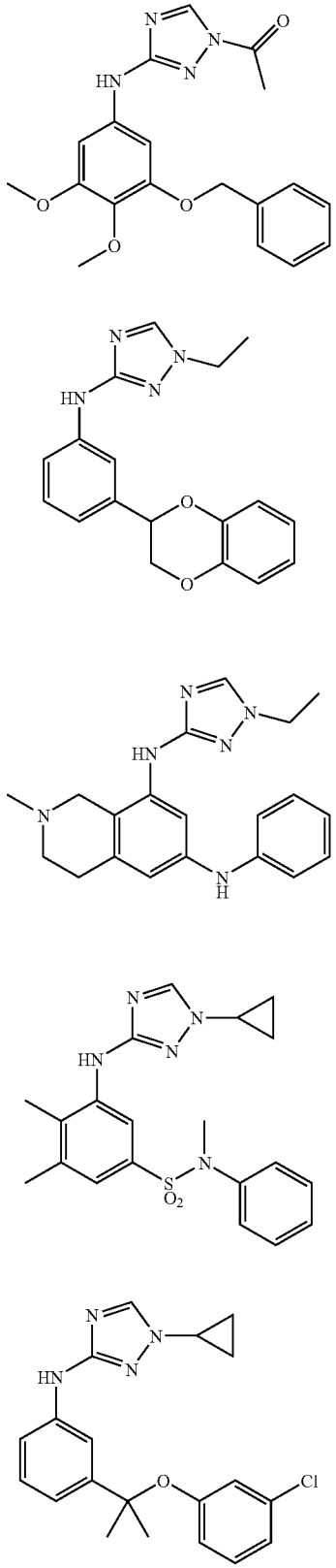
I-33
I-34
I-35
I-36
I-37
TABLE 1-continued
Examples of Compounds of Formula I:
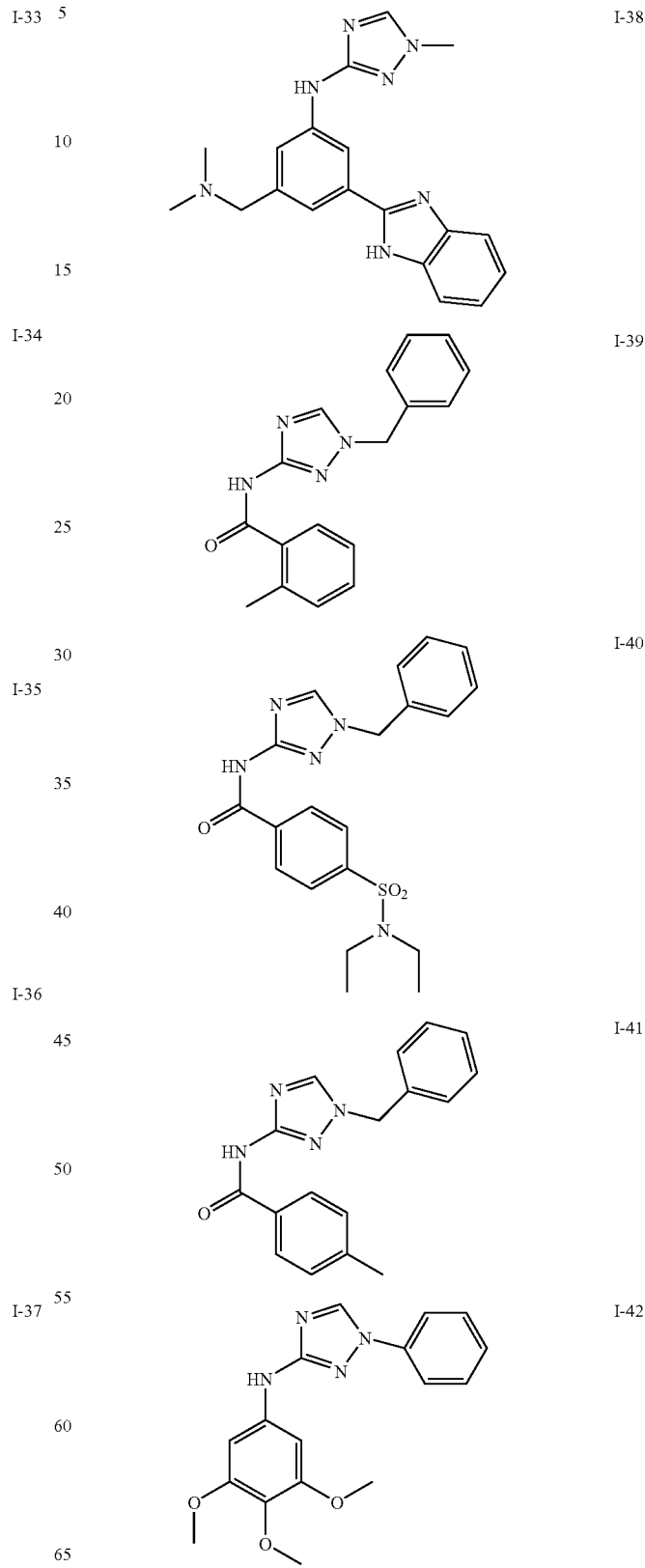
I-38
I-39
I-40
I-41
I-42

TABLE 1-continued

Examples of Compounds of Formula I:

I-43

I-44

I-45

I-46

I-47

I-48

I-49

I-50

I-51

TABLE 1-continued

Examples of Compounds of Formula I:

TABLE 1-continued
Examples of Compounds of Formula I:
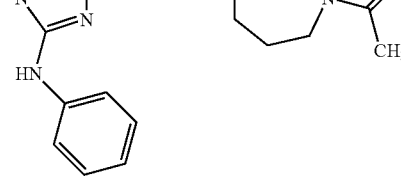
I-62
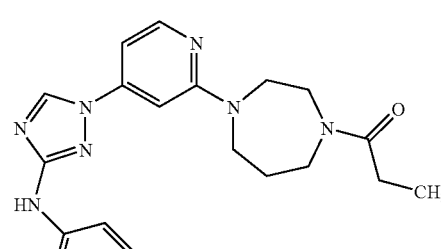
I-63
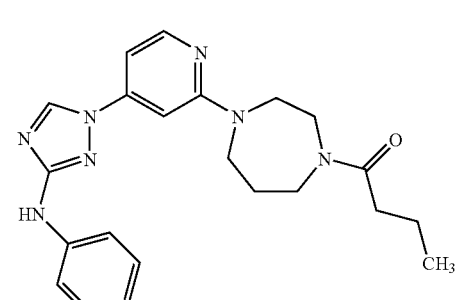
I-64
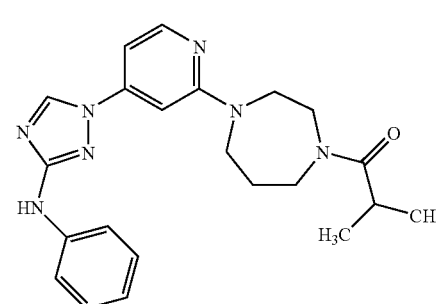
I-65
TABLE 1-continued
Examples of Compounds of Formula I:
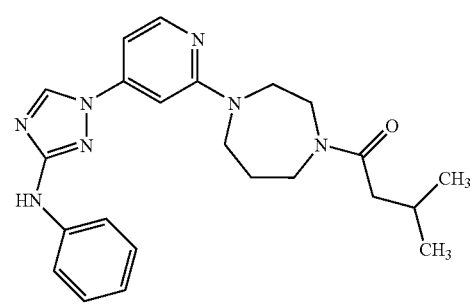
I-66
I-67
I-68
I-69
I-70

TABLE 1-continued

Examples of Compounds of Formula I:

I-71, I-72, I-73, I-74, I-75, I-76, I-77, I-78, I-79

TABLE 1-continued
Examples of Compounds of Formula I:
I-80
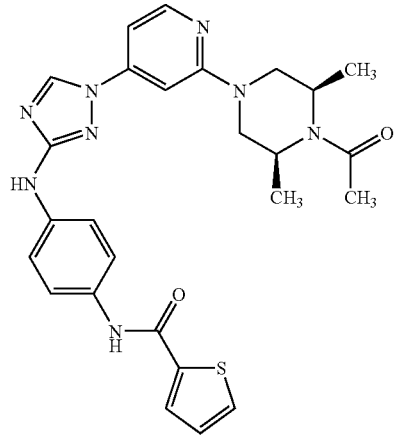
I-81
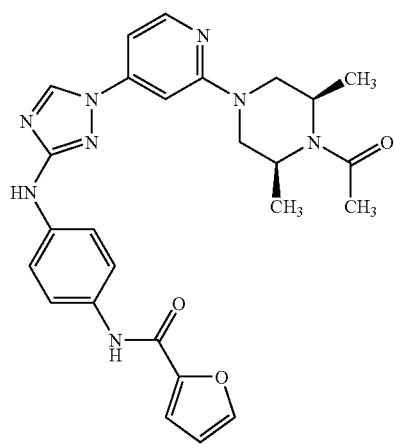
I-82
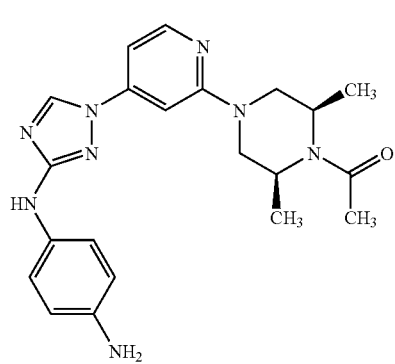
I-83
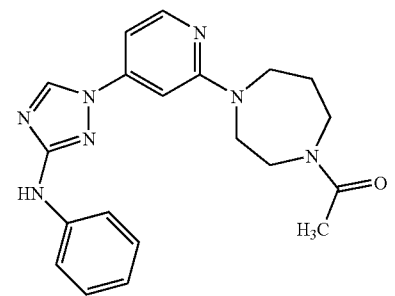
TABLE 1-continued
Examples of Compounds of Formula I:
I-84
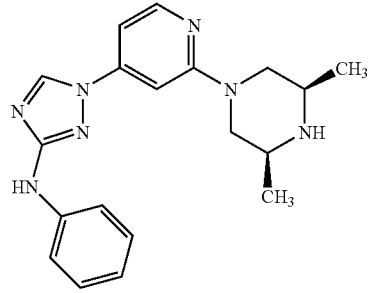
I-85
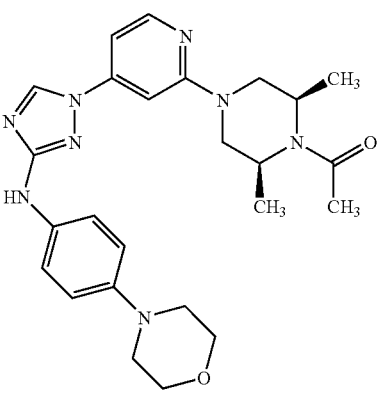
I-86
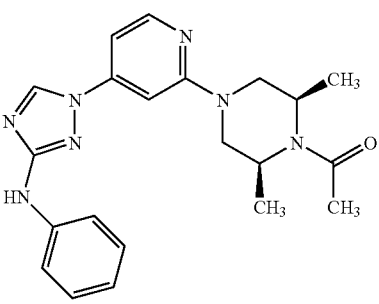
I-87
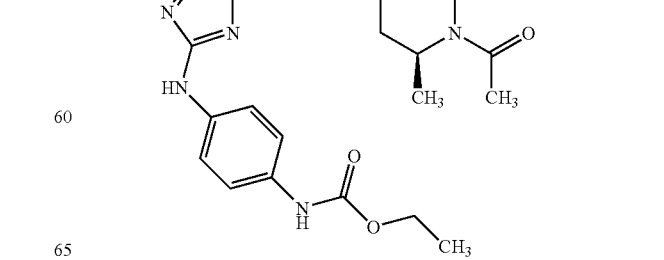

TABLE 1-continued
Examples of Compounds of Formula I:
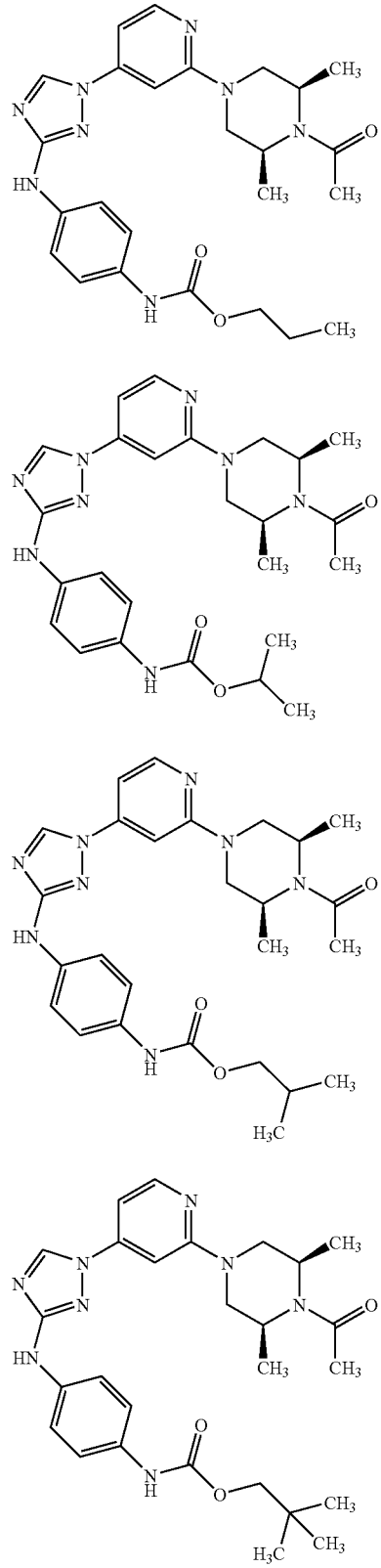
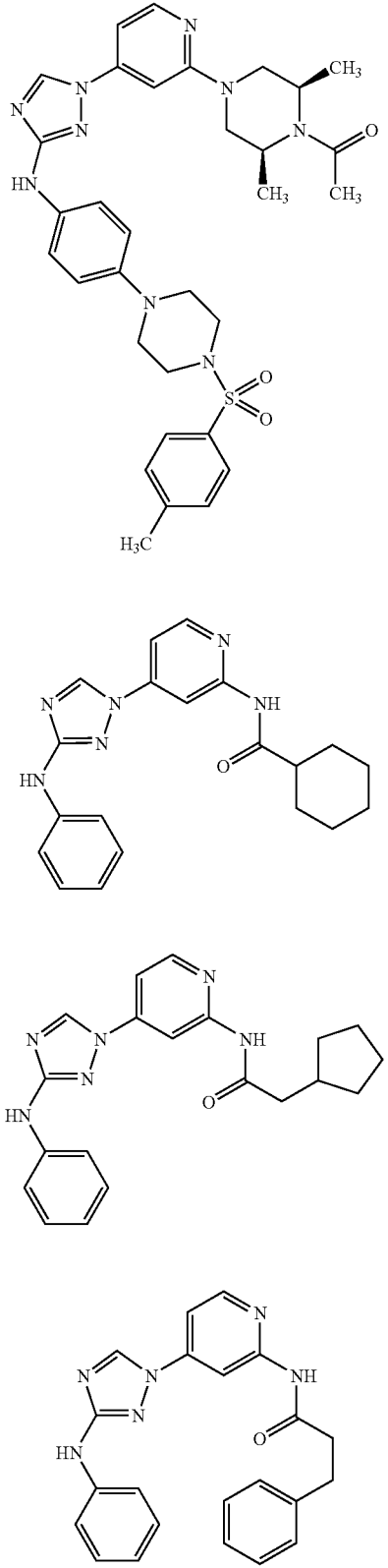

TABLE 1-continued
Examples of Compounds of Formula I:
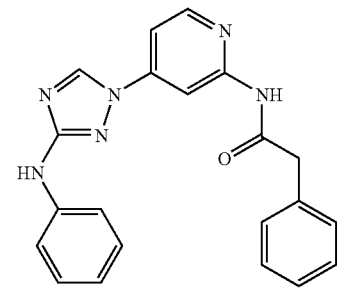
I-96
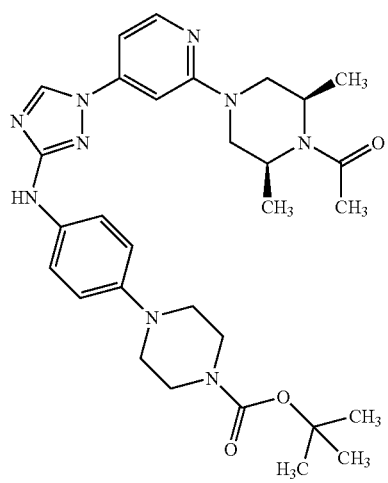
I-97
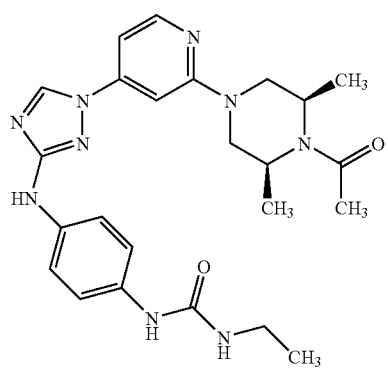
I-98
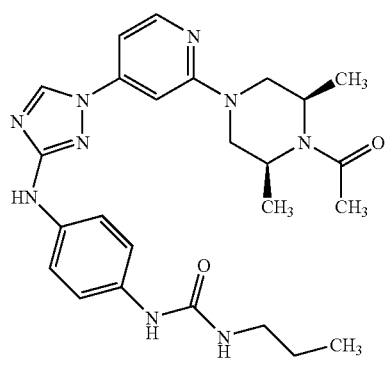
I-99
TABLE 1-continued
Examples of Compounds of Formula I:
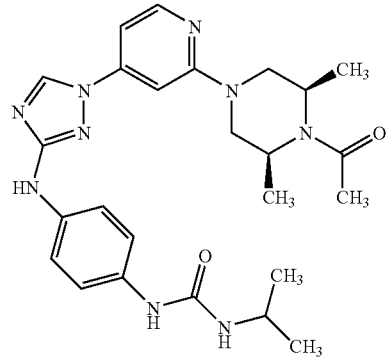
I-100
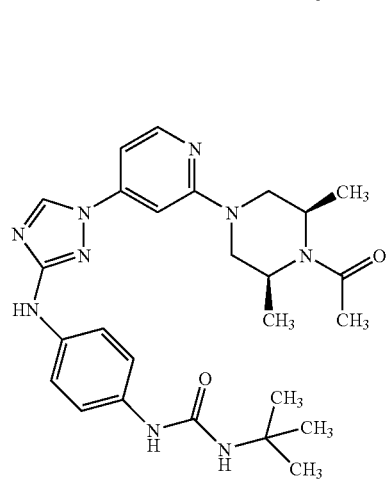
I-101
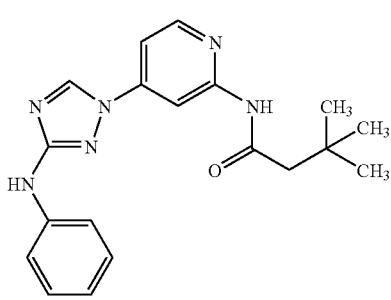
I-102
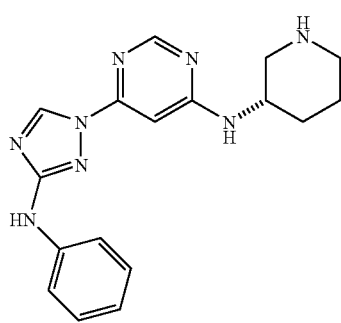
I-103

TABLE 1-continued
Examples of Compounds of Formula I:
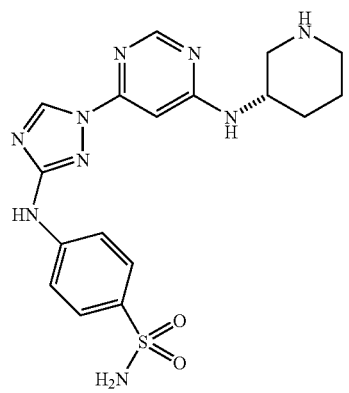
I-104
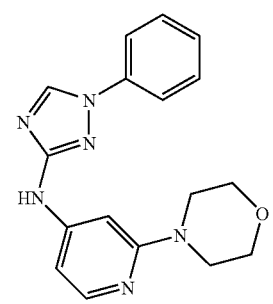
I-105
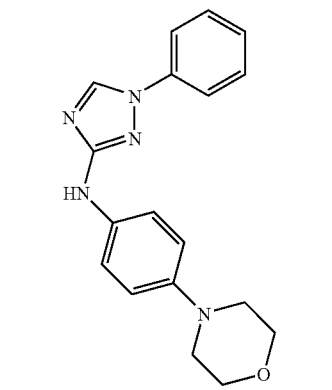
I-106
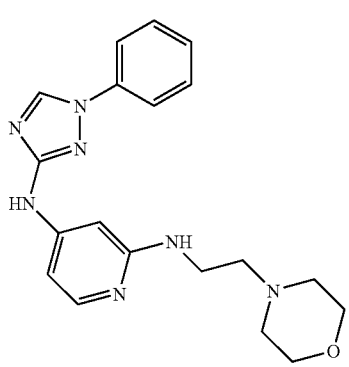
I-107
TABLE 1-continued
Examples of Compounds of Formula I:
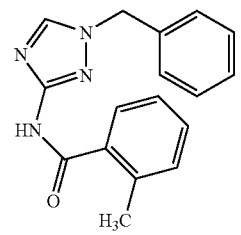
I-108
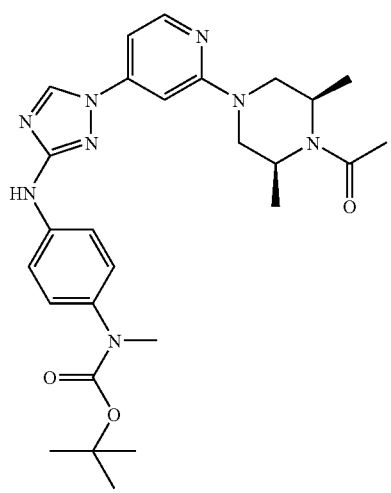
I-109
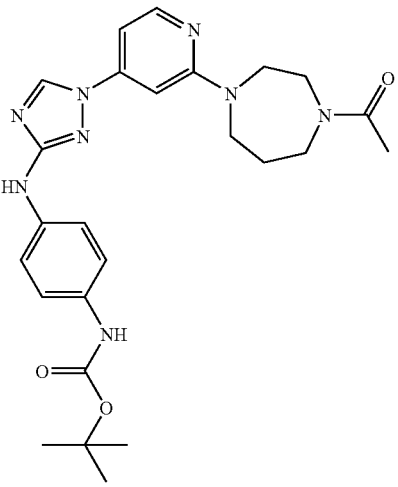
I-110

TABLE 1-continued
Examples of Compounds of Formula I:
I-111
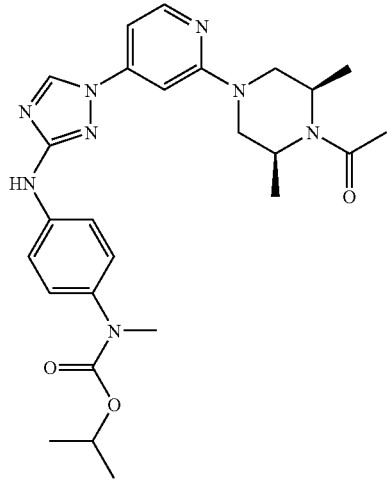
I-112
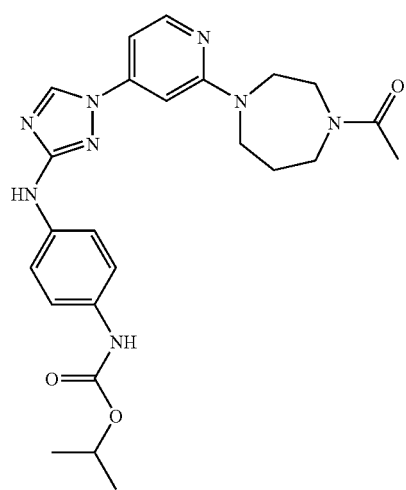
I-113
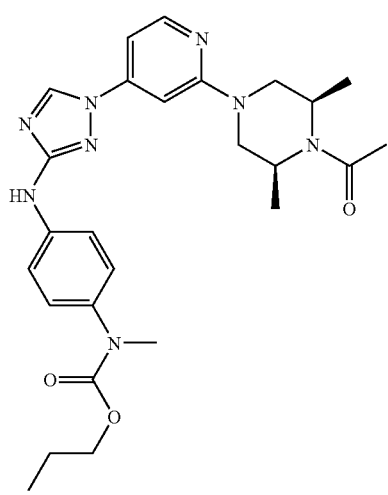
TABLE 1-continued
Examples of Compounds of Formula I:
I-114
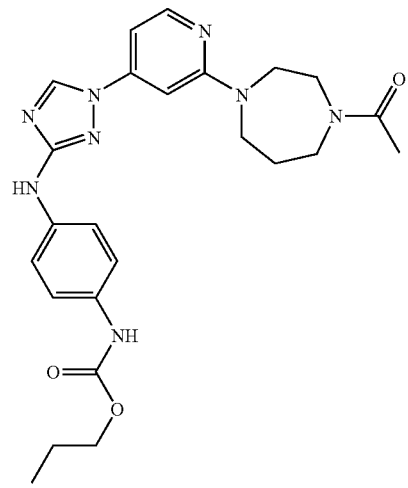
I-115
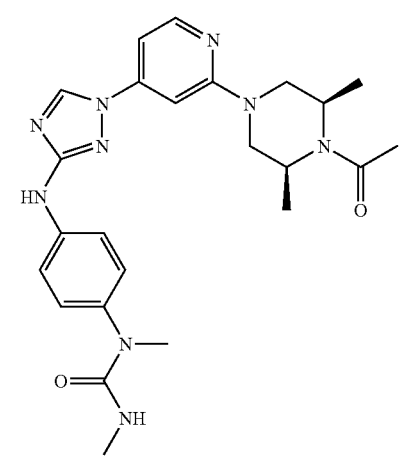
I-116
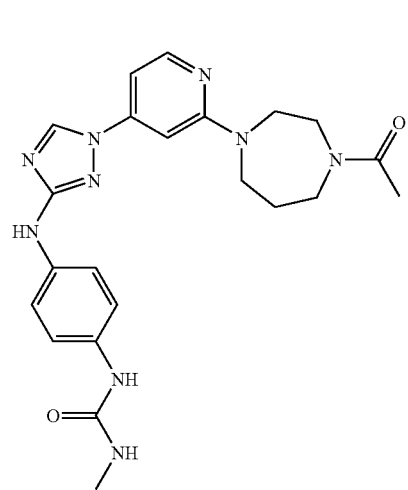

TABLE 1-continued
Examples of Compounds of Formula I:
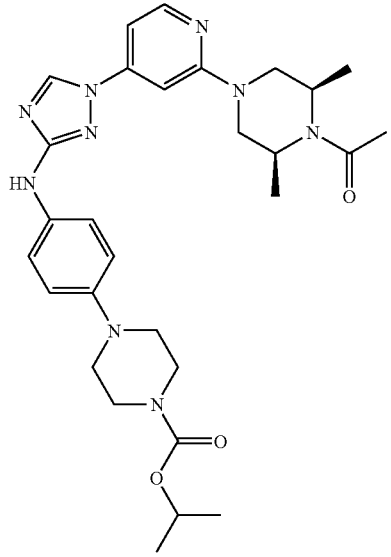
I-117
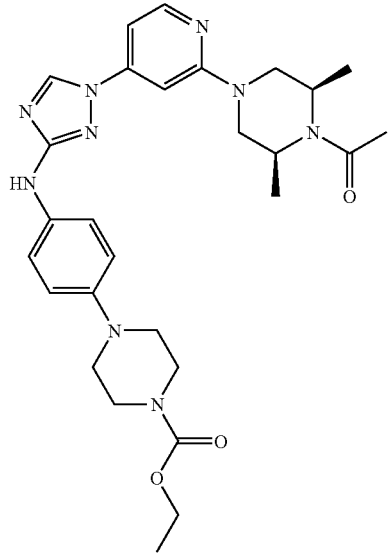
I-119
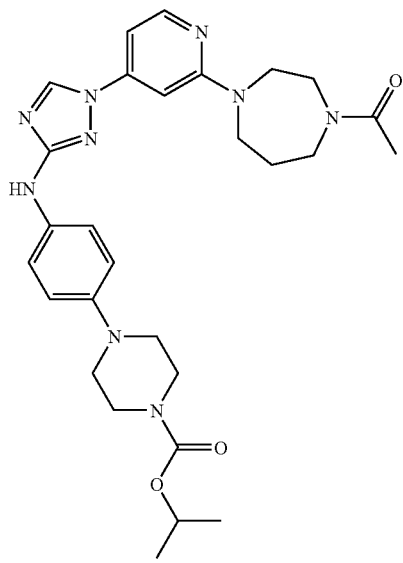
I-118
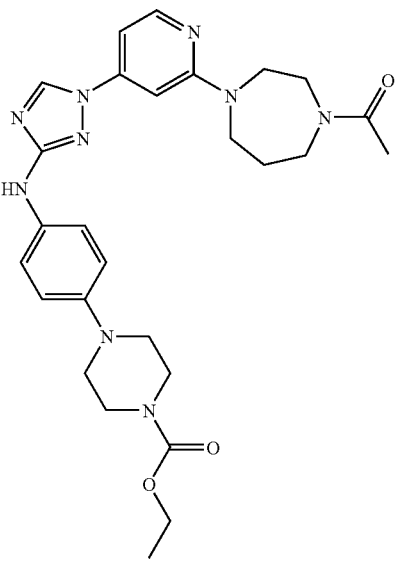
I-120

TABLE 1-continued
Examples of Compounds of Formula I:
I-121
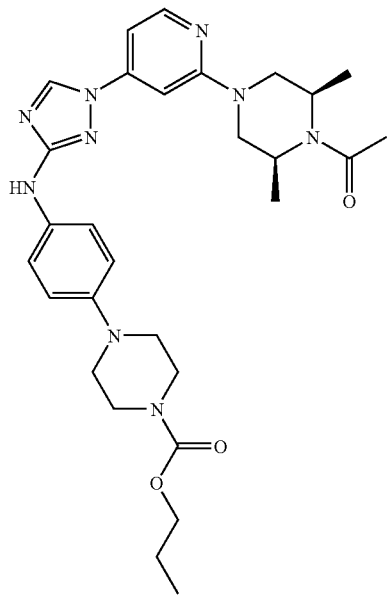
I-122
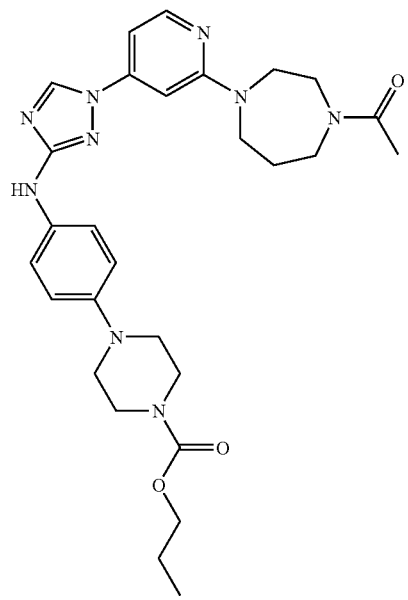
TABLE 1-continued
Examples of Compounds of Formula I:
I-123
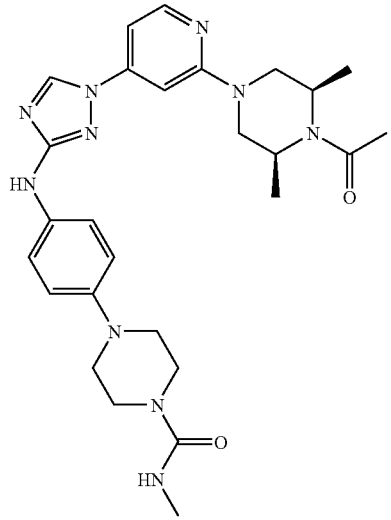
I-124
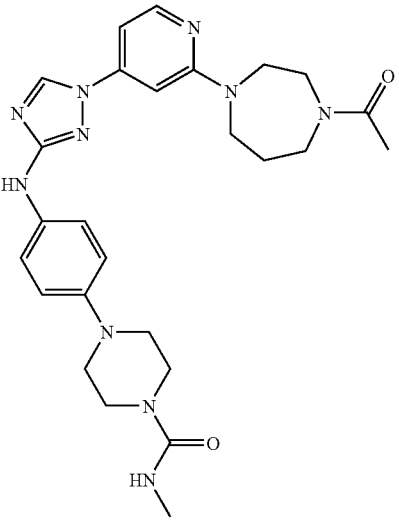
I-125
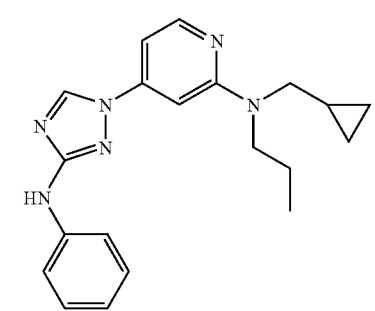

TABLE 1-continued
Examples of Compounds of Formula I:
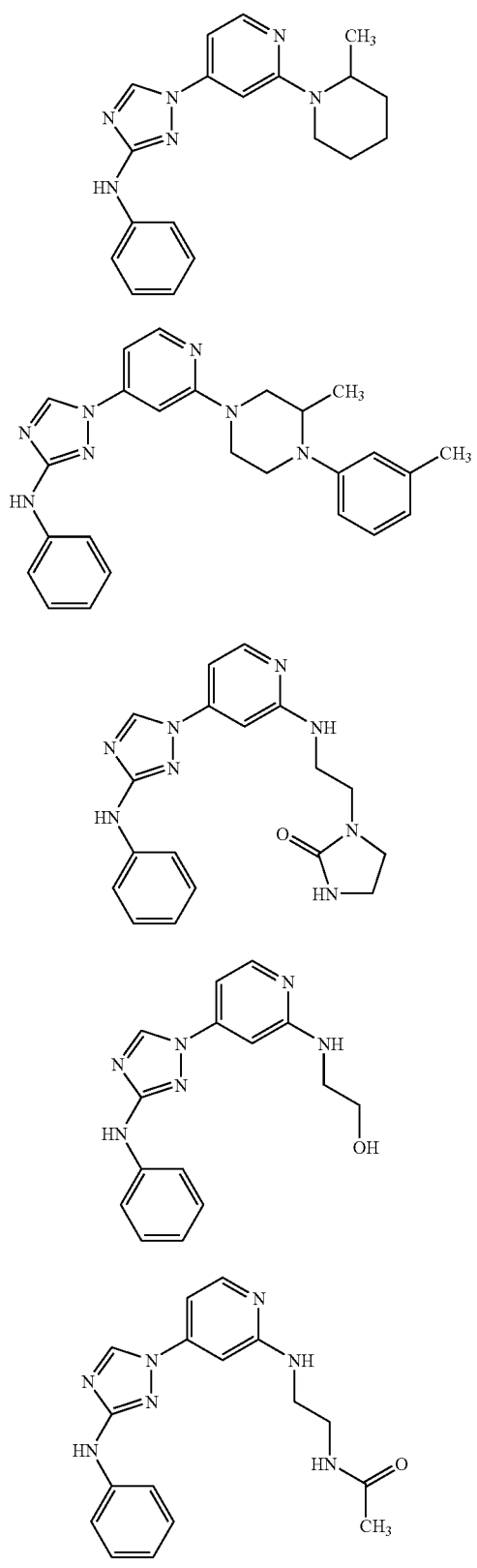
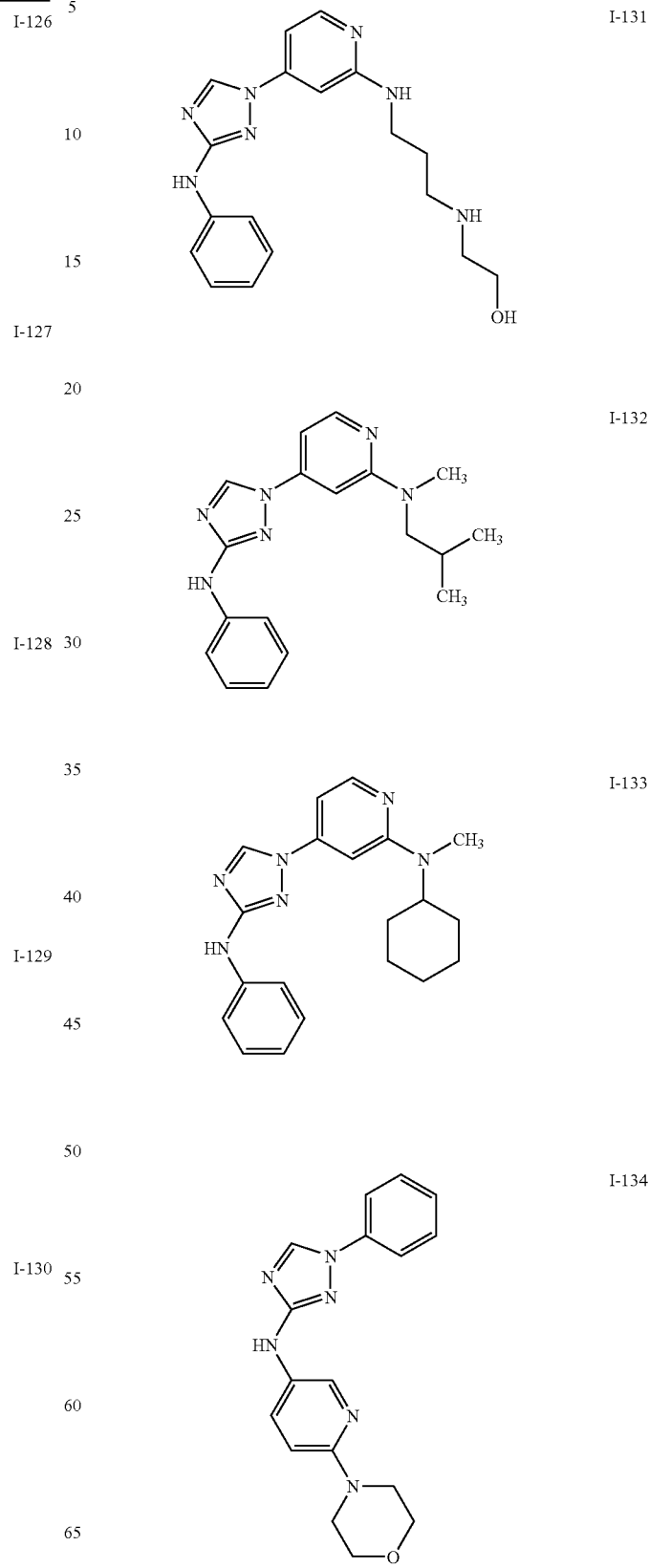

TABLE 1-continued
Examples of Compounds of Formula I:
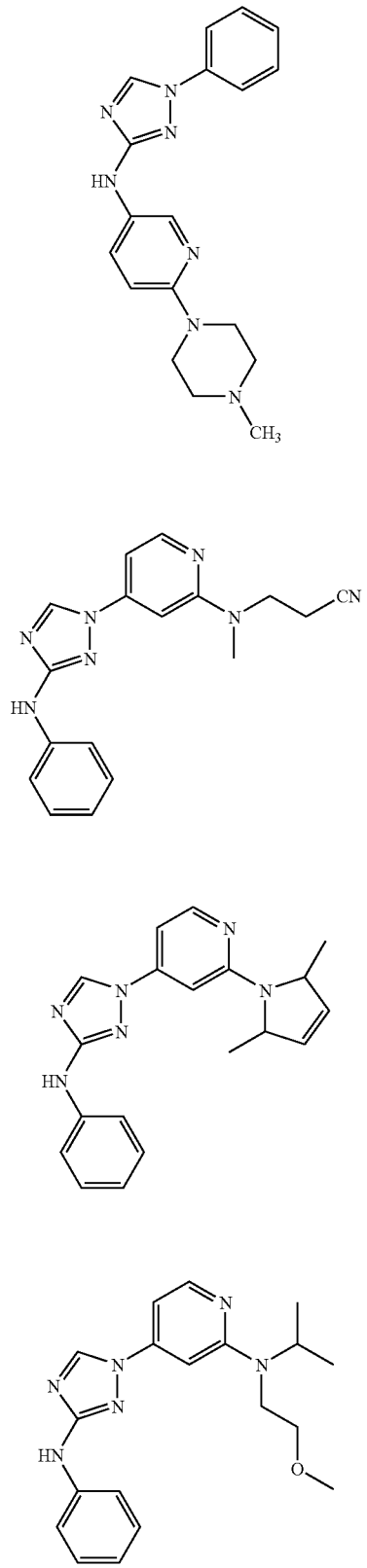
I-135
I-136
I-137
I-138
TABLE 1-continued
Examples of Compounds of Formula I:
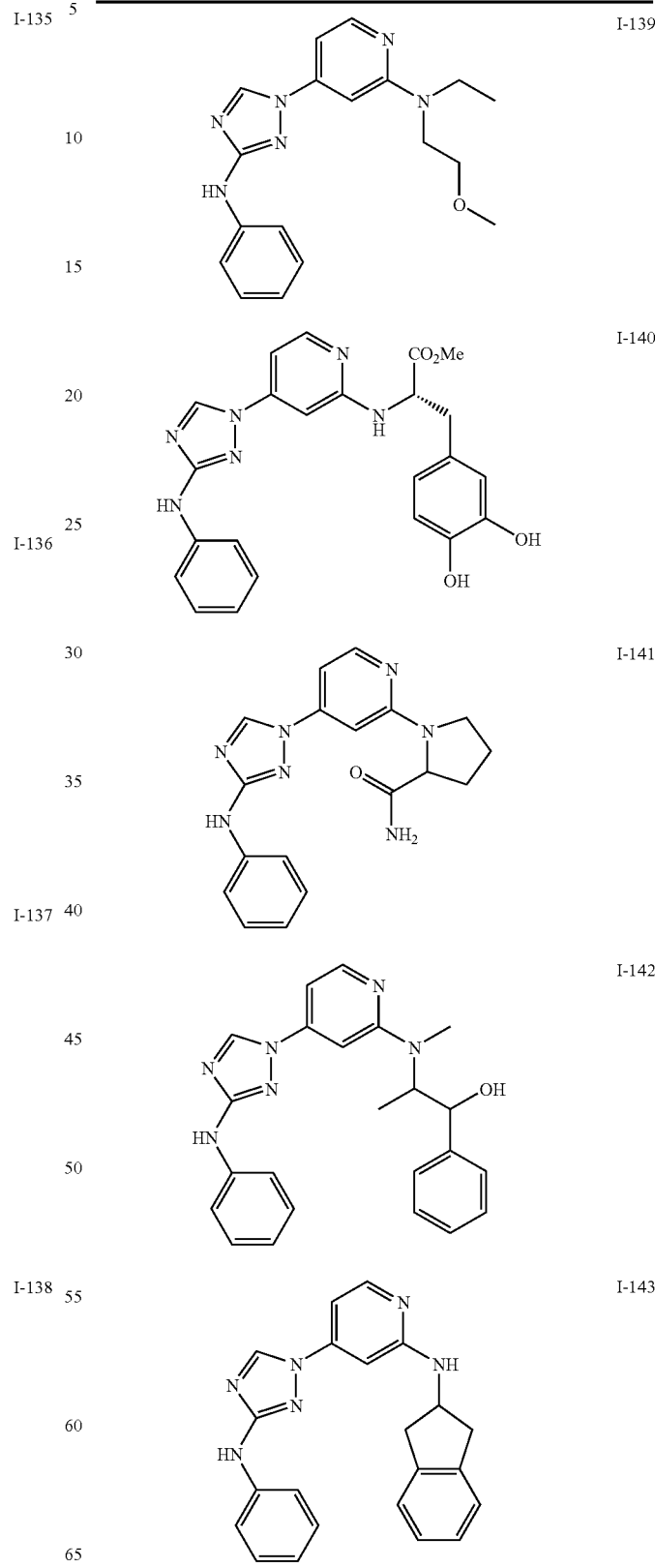
I-139
I-140
I-141
I-142
I-143

TABLE 1-continued
Examples of Compounds of Formula I:
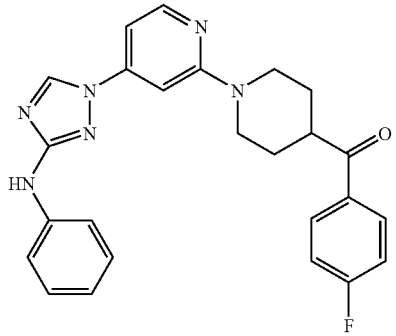
I-144
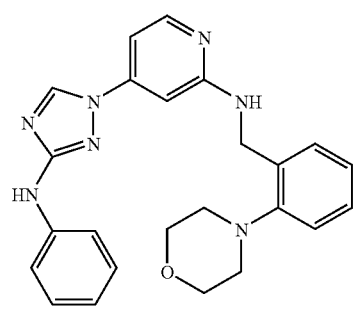
I-145
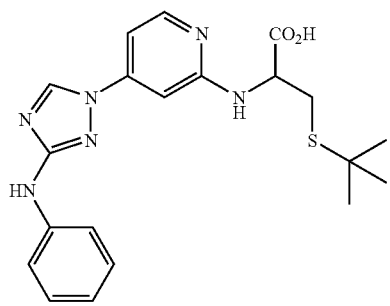
I-146
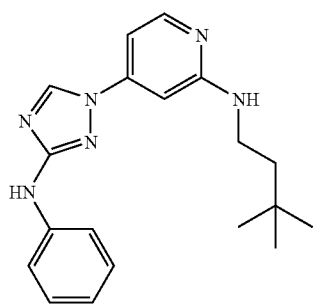
I-147
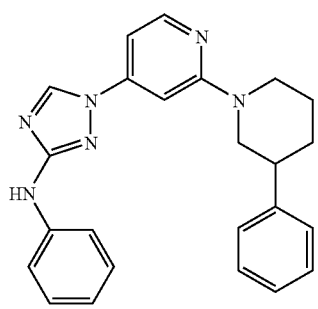
I-148
TABLE 1-continued
Examples of Compounds of Formula I:
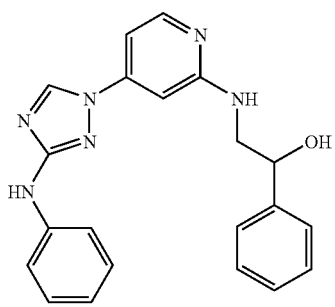
I-149
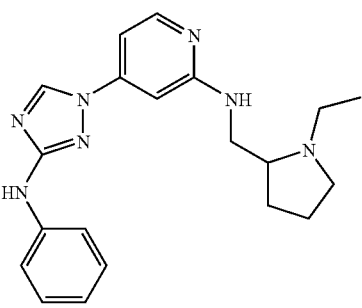
I-150
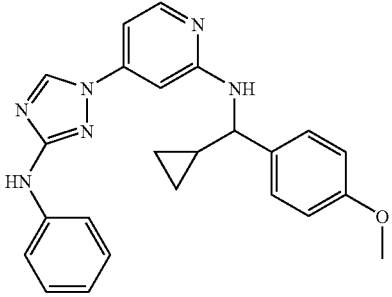
I-151
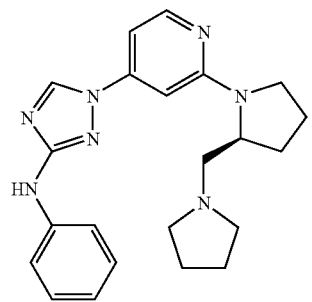
I-152
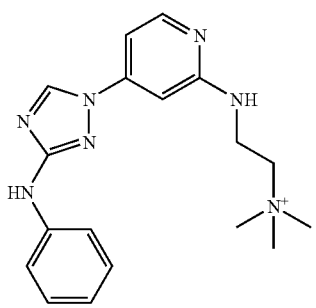
I-153

TABLE 1-continued

Examples of Compounds of Formula I:

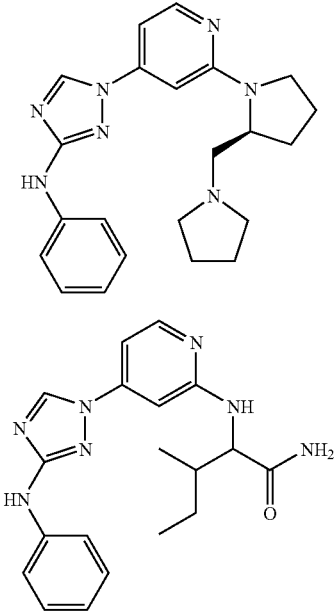

I-154

I-155

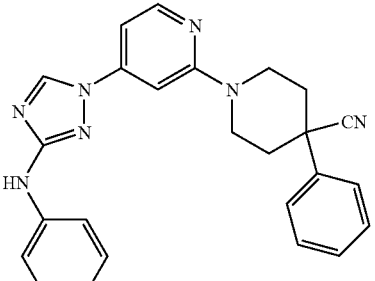

I-156

4. General Synthetic Methodology

The compounds of this invention may be prepared in general by methods known to those skilled in the art for analogous compounds, by methods as illustrated by the general scheme below, and by the preparative examples that follow. The processes for preparing the compounds of this invention are as described in the schemes and examples. In the Schemes, the variables are as defined in the compounds (e.g., formula I) herein or are readily recognized by referring to those compounds.

Scheme 1:

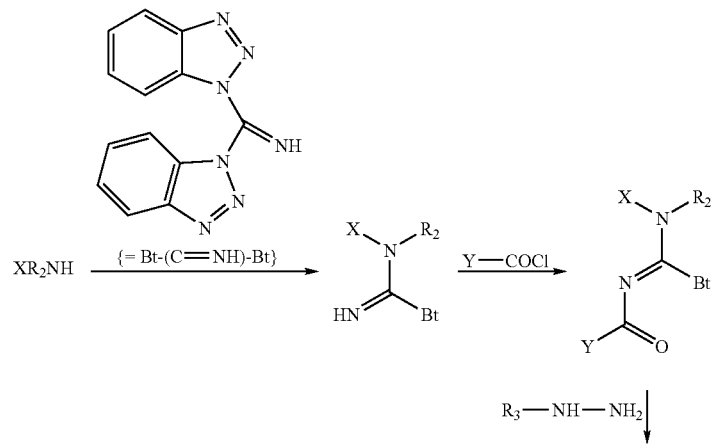

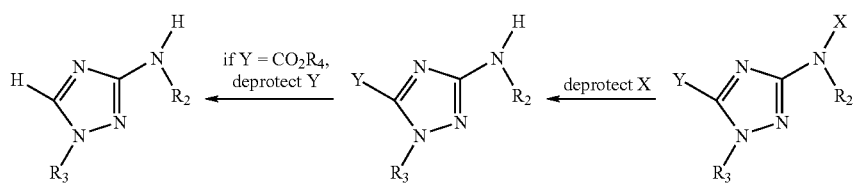

X = protecting group, e.g., allyl or benzyl
$R_2$ = aryl or heteroaryl
Y = H or $CO_2R_4$
$R_3$ = aryl or heteroaryl Scheme 2 below depicts the synthesis of certain exemplary compounds where $R^3$ is —$(L)_m Ar^2$.
Scheme 2:
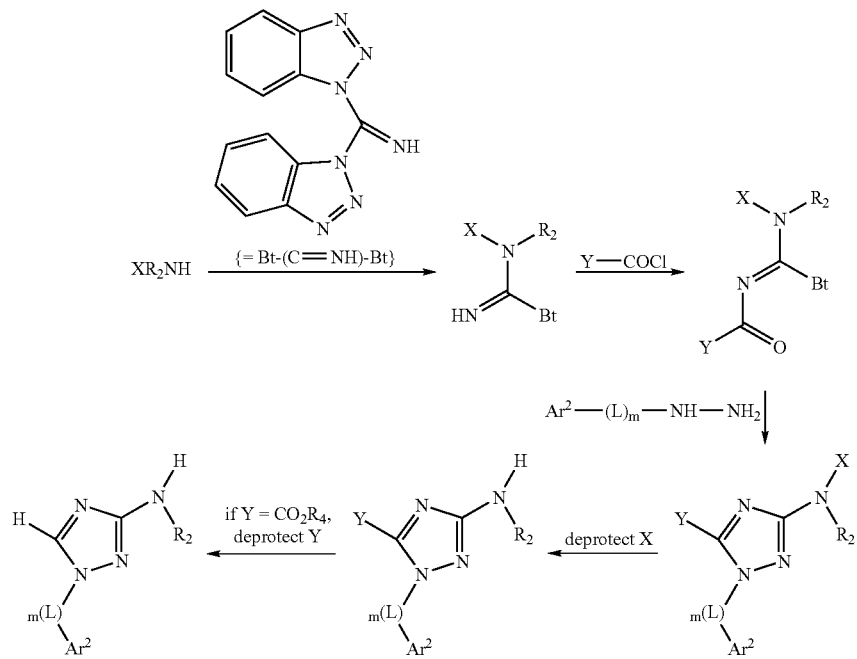
X = protecting group, e.g., allyl or benzyl
$R_2$ = aryl or heteroaryl
Y = H or $CO_2R_4$
Schemes 3 and 4 below depict the synthesis of certain exemplary compounds where $R^2$ is —$(T)_n Ar^1$.
Scheme 3:
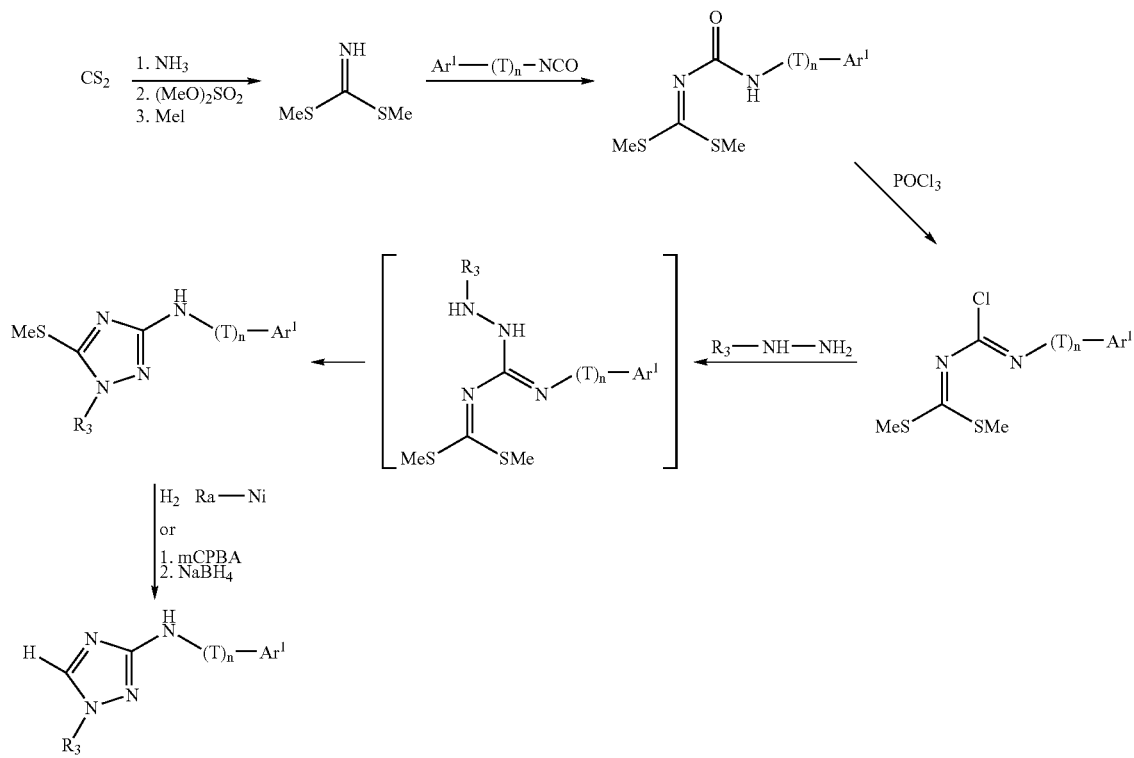

Scheme 4:

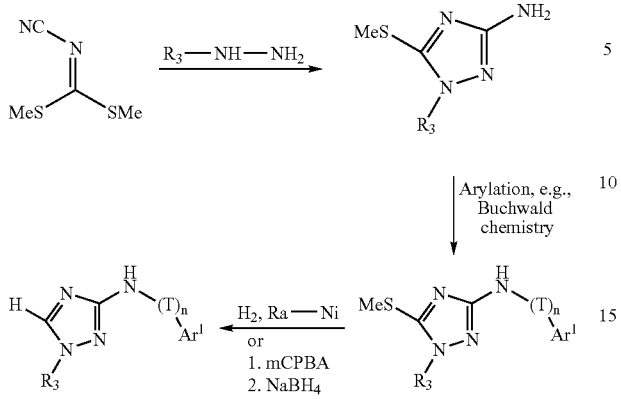

Scheme 5 depicts the synthesis of certain exemplary compounds where $R^3$ is $-(L)_mAr^2$.

Scheme 5:

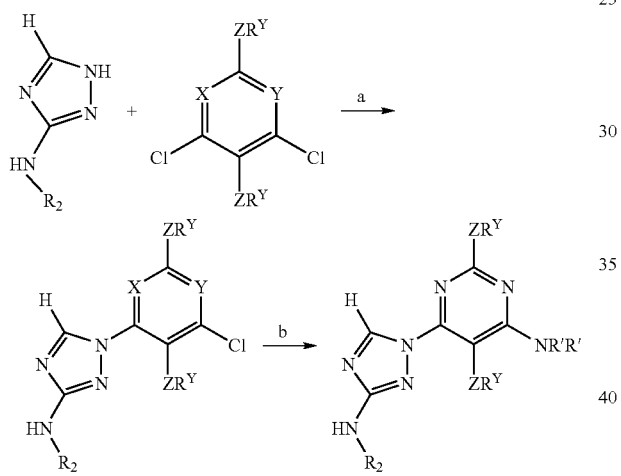

Conditions: a) DIEA, CH$_3$CN, reflux, overnight; b) microwave, 6 mins., NMP, 200° C.

Scheme 5 depicts the synthesis of compounds where $R^3$ is $-(L)_mAr^2$ and one of X and Y is N; both X and Y are N; or both X and Y are CH or a carbon atom substituted by a group including, e.g., carboxylate esters, amides, carbamates, ureas, or nitrites. The route of this scheme may also be employed to prepare compounds where $R^2$ is as defined in any of the embodiments herein. When $R^2$ is $-(T)_nAr^1$, $Ar^1$ may be a variety of groups, including, e.g., a phenyl substituted with up to 5 groups, or an optionally substituted 5- or 6-membered heteroaromatic ring. $ZR^Y$ may be any group or substituent defined herein, such as hydrogen, carboxylate esters, amides, acids, carbamates, ureas, or nitrites. Each R' is intended to depict any amine group of formula (I) including, e.g., acyclic or cyclic alkyl groups or groups where the R' groups form a ring. These R' groups are optionally substituted with, e.g., carboxylate esters, amides, carbamates, ureas, or nitrites. Each R' may also be an optionally substituted aromatic, heterocylic, or heteroaromatic group.

Although certain conditions are depicted in Scheme 5, skilled practitioners would realize that the depicted conditions could be varied or that other conditions may also be used to carry out the same transformations.

Scheme 6:

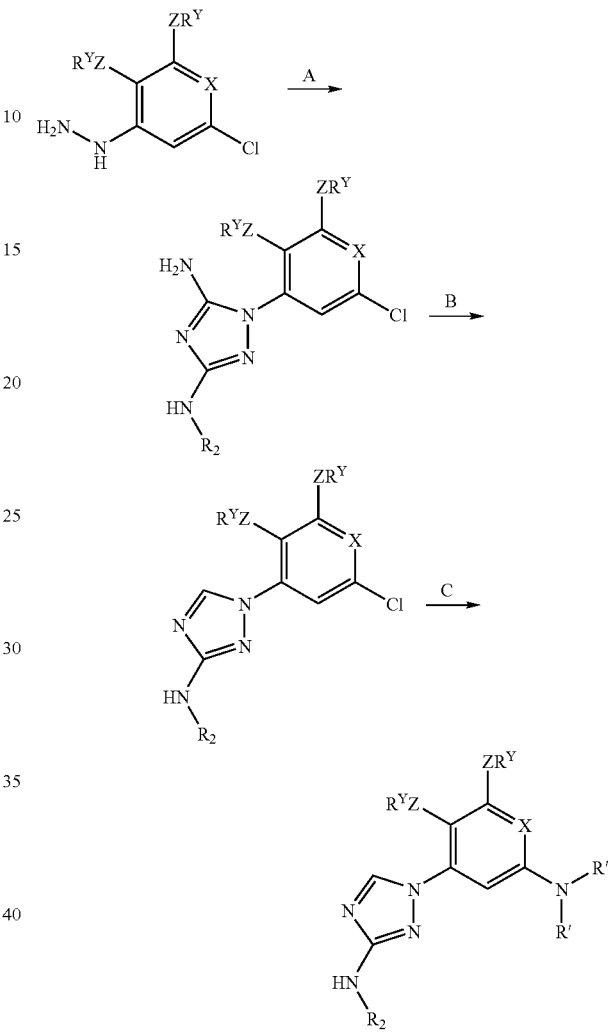

Conditions: A) N-cyano, N-R$^2$-phenylisourea, 220° C., μW; B) NO+BF4-, THF; C) R'R'NH, NMP, 250° C., μW or R'R'NH, Pd$_2$(dba)$_3$, dppp, KOtBu, toluene Scheme 6 depicts the synthesis of compounds of formula (I) where $R^3$ is $-(L)_mAr^2$ where $Ar^2$ optionally contains a heteroatom. This route is particularly useful for the synthesis of compounds wherein $Ar^2$ is a 6-membered, non-pyrimidine ring. In such compounds, X is a nitrogen atom or a carbon atom, where the carbon is optionally substituted with, e.g., CO$_2$R (acid or ester form), CN, alkyl, or CONR$_2$. The $Ar^2$ is optionally fused to a 5- or 6-membered carbocyclic or heterocyclic saturated, unsaturated, or aromatic ring (wherein each ring is optionally substituted). Such compounds are those wherein R$_1$ and R$_2$ form a ring. Alternatively, R$_1$ and R$_2$ are each independently a substituent such as, e.g., CO$_2$R (acid or ester form), CN, alkyl, alkoxy, or halo (particularly Cl or F). Compounds of formula (I) where $R^2$ is a variety of groups may also be prepared by this route ($-(T)_nAr^1$ is depicted here as $R_3$). For example, compounds of formula (I) wherein $Ar^1$ is an aromatic (e.g., optionally substituted with up to three groups) or a heteroaromatic ring (e.g., optionally substituted with up to two substituents) could be prepared by this route.

The chemistry depicted can be used with compounds having substituents on the Ar¹ ring. For example, an aromatic ring may be optionally substituted with up to three groups and a heteroaromatic ring may be optionally substituted with up to two substituents.

All such compounds could be prepared. Although certain conditions are depicted in Scheme 6, skilled practitioners would realize that the depicted conditions could be varied or that other conditions may also be used to carry out the same transformations For example, the cyclization can also be done thermally (i.e., heating outside the microwave, see e.g., WO 2004/046120). Such modification would be well-known to skilled practitioners. The deamination step B may be sensitive to substitutions on the aniline ring. Alternative routes may be needed for, e.g., amino-substituted compounds. For example, in the case of an amine-substituted compound is desired, an ester instead of an amine may be carried through the synthesis. A late stage Curtius reaction would provide the amine substituted compound. For substitutions on the pyridyl ring, Buchwald conditions may be employed.

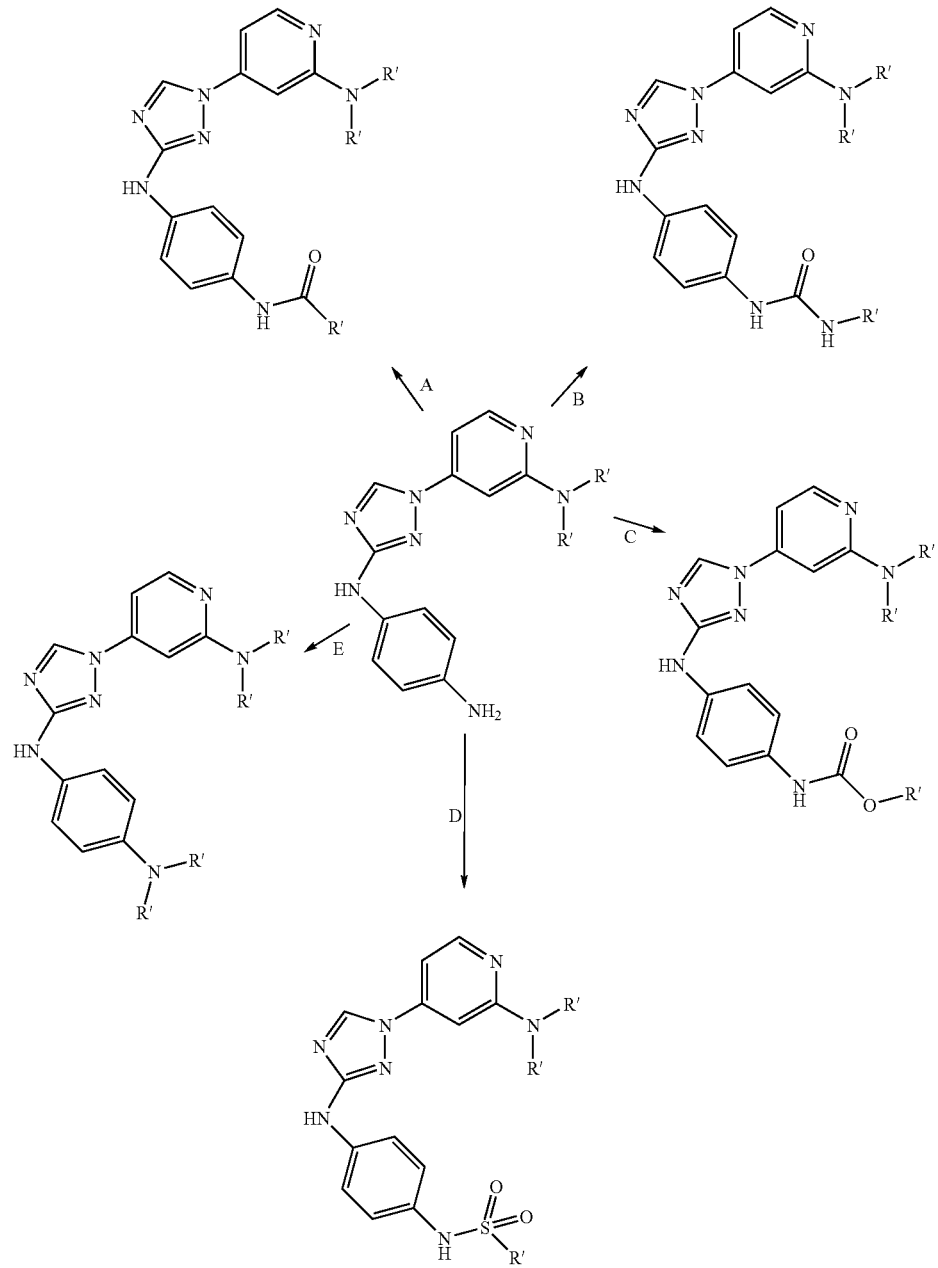

Scheme 7 depicts the synthesis of certain exemplary compounds where Ar¹ and Ar² is substituted General conditions: solvent, base, appropriate coupling agent, e.g.: A. DMF, DIEA, RCOCl; B. DMF, IEA, isocyanate; C. DMF, DIEA, chloroformate D. DMF, DIEA, ISO2R; E. iPrOH,alkyl halide, heat.

Scheme 7 depicts a route to compounds of this invention wherein an Ar¹ is substituted with an amine derivative, specifically where R² is (T)ₙAr¹, and Ar¹ is substituted with an amine derivative. In Scheme 7, the amine group is reacted under standard coupling conditions to provide an amine derivative. It should be understood that the depicted synthesis could be modified to also provide other amine derivatives. Furthermore, coupling conditions other than those depicted could be used. Such methods are well-known to skilled practitioners (see, e.g., Greene or Greene & Wutz, Protective Groups in Organic Synthesis; WO 01/81330). It should be understood that the conditions should typically be chosen to be compatible with (i.e., unreactive to) the remaining substituents (e.g., the —NR¹R²).

Scheme 8: Triazole deamination route.

X is as exemplified by the compounds herein and is optionally substituted with $ZR^Y$ (e.g., X is N, CH, $CCO_2R$, CCN, CR', $CCON(R')_2$.

Each $ZR^Y$ (together with the atoms of the X-containing ring) can form a 5- or 6-membered carbo- or heterocyclic ring (including aromatic, unsaturated, or saturated). Alternatively, each $ZR^Y$ is as defined herein (e.g., $CO_2H$, CN, $CO_2R'$, OR', Cl, F, or R').

R² is as defined herein, e.g., an aromatic (in certain embodiments, up to triply substituted) ring or a 5- or 6-membered heteroaromatic ring (in certain embodiments, up to doubly substituted).

Each R' is as defined herein.

Scheme 9: Amination of chloropyridines

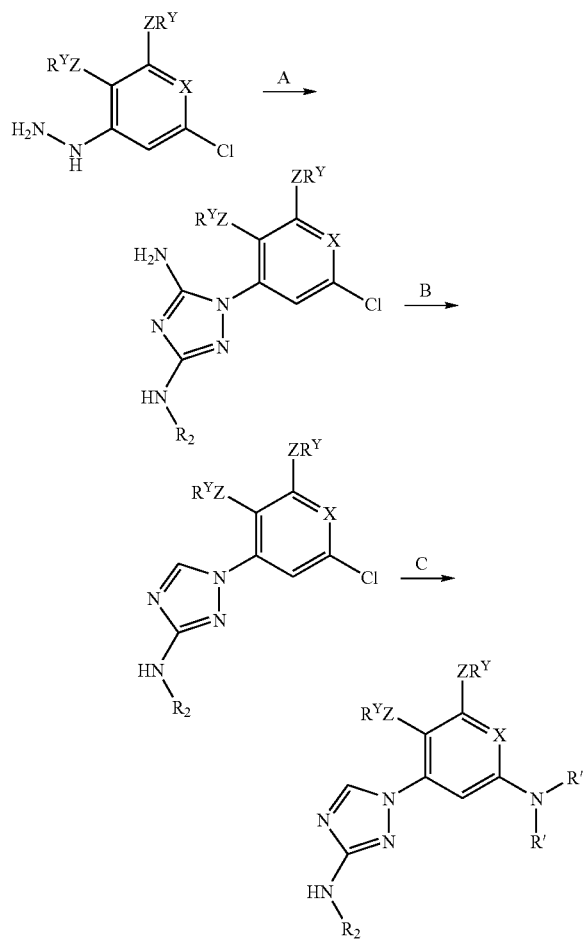

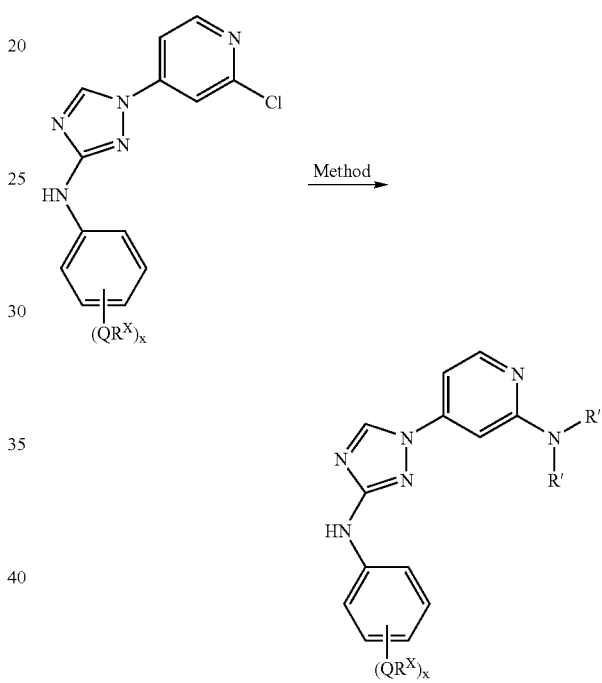

Conditions: A) N-cyano, N-R²-phenylisourea, 220° C., μ W; B) NO + BF4-, THF; C) method i: R'R'NH, NMP, 250° C., μW; or method ii: R'R'NH, Pd₂(dba)3, SIPr-HCl, NaOtBu, dioxane, or method iii: R'R'NH, neat, 120-140° C. (thermal), or method iv: R'R'NH, nBuOH, BMIM-OTf (ionoc liquid), 200-230° C., μW or method v: R'R'NH, nBuOH, 120-140 °C. (thermal).

Certain compounds of this invention can be prepared by amination of a pyridylchloride. Amination of the pyridylchloride can be achieved via a variety of methods. Examples of such methods include: i: R'R'NH, NMP, 250° C., μW; Method ii: R'R'NH, Pd₂(dba)₃, SIPr—HCl, NaOtBu, dioxane; Method iii: R'R'NH, neat, 120-140° C. (thermal); Method iv: R'R'NH, nBuOH, BMIM-OTf (ionic liquid), 200-230° C., μW; Method v: R'R'NH, nBuOH, 120-140° C. (thermal).

Scheme 10: Alternative route to certain exemplary compounds of this invention.

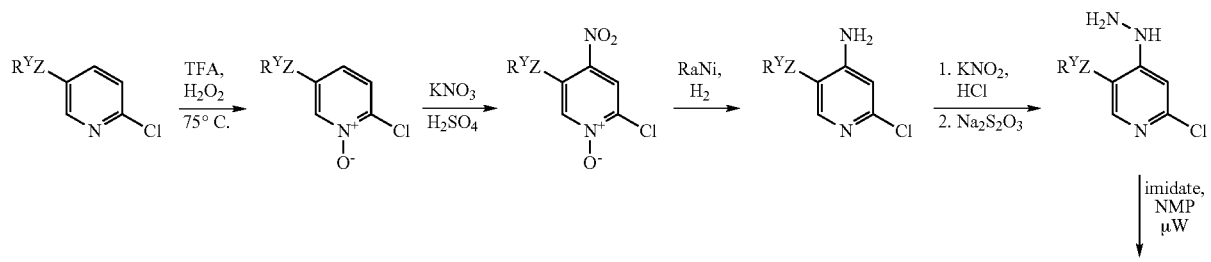

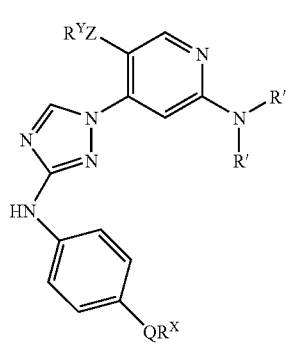

-continued

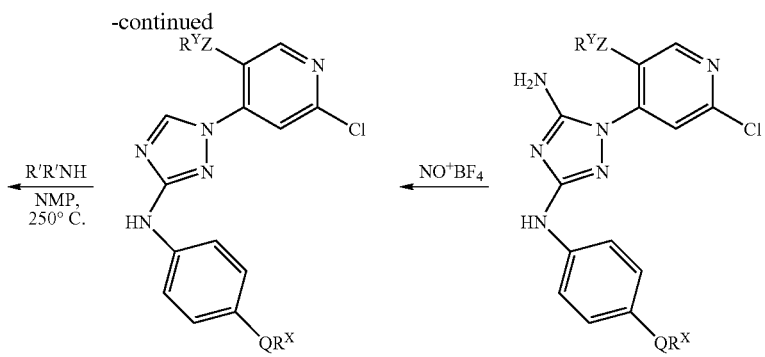

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to, allergic disorders, proliferative disorders, autoimmune disorders, conditions associated with organ transplant, inflammatory disorders, immunologically mediated disorders, viral diseases, or destructive bone disorders (such as bone resorption disorders). Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a protein kinase, particularly PDK-1, FMS, c-KIT, GSK-3, CDK-2, SRC, JAK-1, JAK-2, JAK-3, TYK-2, FLT-3, KDR, PDGFR, ROCK SYK, AUR-1, or AUR-2 kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of allergic disorders, proliferative disorders, autoimmune disorders, conditions associated with organ transplant, inflammatory disorders, immunologically mediated disorders, viral diseases, or destructive bone disorders (such as bone resorption disorders) is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of the disease, disorder, or condition of interest. The compounds and compositions, according to the method of the present invention, may be administered using any amount and any route of administration effective for treating or lessening the severity of the disease, disorder, or condition of interest. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases (including tyrosine and serine/threonine kinases). In one embodiment, the compounds and compositions of the invention are inhibitors of one or more of PDK-1, FMS, c-KIT, GSK-3, CDK-2, SRC, JAK-1, JAK-2, JAK-3, TYK-2, FLT-3, KDR, PDGFR, ROCK, SYK, AUR-1, or AUR-2 kinases. In certain preferred embodiments, these compounds are effective as inhibitors of JAK-1, JAK-2, JAK-3, TYK-2, FLT-3, c-KIT, CDK-2, KDR, PDK-1, or AUR-2 protein kinases. In certain more preferred embodiments, these compounds are effective as inhibitors of JAK or PDK-1 protein kinases. Thus, without wishing to be bound by any particular theory, the compounds and compositions are particularly useful for treating or lessening the severity of a disease, condition, or disorder where activation of one or more of the protein kinases, including PDK-1, FMS, c-KIT, GSK-3, CDK-2, SRC, JAK-1, JAK-2, JAK-3, TYK-2, FLT-3, KDR, PDGFR, ROCK, SYK, AUR-1, or AUR-2 kinases is implicated in the disease, condition, or disorder. When activation of the PDK-1, FMS, c-KIT, GSK-3, CDK-2, SRC, JAK-1, JAK-2, JAK-3, TYK-2, FLT-3, KDR, PDGFR, ROCK, SYK, AUR-1, or AUR-2 kinases is implicated in a particular disease, condition, or disorder, the disease, condition, or disorder may also be referred to as "PDK-1, FMS, c-KIT, GSK-3, CDK-2, SRC, JAK-1, JAK-2, JAK-3, TYK-2, FLT-3, KDR, PDGFR, ROCK or SYK-mediated disease" or disease symptom. Accordingly, in another aspect, the present invention provides a method for treating or lessening the severity of a disease, condition, or disorder where activation or one or more protein kinase, including the PDK-1, FMS, c-KIT, GSK-3, CDK-2, SRC, JAK-1, JAK-2, JAK-3, TYK-2, FLT-3, KDR, PDGFR, ROCK, SYK, AUR-1, or AUR-2 kinases is implicated in the disease state.

The activity of a compound utilized in this invention as an inhibitor of a protein kinase, may be assayed in vitro, in vivo or in a cell line. In vitro assays include assays that determine inhibition of either the phosphorylation activity or ATPase activity of, e.g., activated PDK-1, FMS, c-KIT, GSK-3, CDK-2, SRC, JAK-1, JAK-2, JAK-3, TYK-2, FLT-3, KDR, PDGFR, ROCK, SYK, AUR-1, or AUR-2. Alternate in vitro assays quantitate the ability of the inhibitor to bind to the protein kinase. Inhibitor binding may be measured by radiolabelling the inhibitor prior to binding, isolating the inhibitor/enzyme, complex and determining the amount of radiolabel bound. Alternatively, inhibitor binding may be determined by running a competition experiment where new inhibitors are incubated with, e.g., PDK-1, FMS, c-KIT, GSK-3, CDK-2, SRC, JAK-1, JAK-2, JAK-3, TYK-2, FLT-3, KDR, PDGFR, ROCK, SYK, AUR-1, or AUR-2 bound to known radioligands.

The term "measurably inhibit", as used herein means a measurable change in a kinase activity between a sample comprising a composition and a kinase and an equivalent sample comprising the kinase in the absence of the composition.

The term "FLT-3-mediated disease", as used herein means any disease or other deleterious condition in which a FLT-3 family kinase is known to play a role. Such conditions include, without limitation, hematopoietic disorders, in particular, acute-myelogenous leukemia (AML), acute-promyelocytic leukemia (APL), and acute lymphocytic leukemia (ALL).

The term "FMS-mediated disease", as used herein means any disease or other deleterious condition in which a FMS family kinase is known to play a role. Such conditions include, without limitation, cancer (including, but not limited to, ovarian, endometrial, and breast cancer), inflammatory disorders, and hypertension.

The term "c-KIT-mediated disease", as used herein means any disease or other deleterious condition in which a c-KIT family kinase is known to play a role. Such conditions include, without limitation, AML, chronic myelogenous leukemia (CML), mastocytosis, anaplastic large-cell lymphoma, ALL, gastrointestinal stromal tumor (GIST), T-cell lymphoma, adenoid cystic carcinoma, angiosarcoma, endometrial carcinoma, small cell lung carcinoma, prostate cancer, ovarian cancer, breast carcinoma, thyroid carcinoma, malignant melanoma and colon carcinoma.

The terms "CDK-2-mediated disease" or "CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P. *Current Medicinal Chemistry*, 2000, 7, 1213-1245; Mani, S., Wang, C., Wu, K., Francis, R. and Pestell, R. *Exp. Opin. Invest. Drugs* 2000, 9, 1849; Fry, D. W. and Garrett, M. D. *Current Opinion in Oncologic, Endocrine & Metabolic Investigational Drugs* 2000, 2, 40-59.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases, cardiovascular diseases, allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia, stroke, and baldness.

The term "JAK-mediated disease", as used herein means any disease or other deleterious condition in which a JAK family kinase, in particular JAK-3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. PDK1-mediated diseases or conditions include, but are not limited to, proliferative disorders, and cancer. Preferably, said cancer is selected from pancreatic, prostate, or ovarian cancer.

The terms "SRC-mediated disease" or "SRC-mediated condition", as used herein mean any disease or other deleterious condition in which SRC is known to play a role. The terms "SRC-mediated disease" or "SRC-mediated condition" also mean those diseases or conditions that are alleviated by treatment with a SRC inhibitor. Such conditions include, without limitation, hypercalcemia, osteoporosis, osteoarthritis, cancer, symptomatic treatment of bone metastasis, and Paget's disease. SRC protein kinase and its implication in various diseases has been described [Soriano, *Cell,* 1992, 69, 551; Soriano et al., *Cell* 1991, 64, 693; Takayanagi, *J. Clin. Invest.* 1999, 104, 137; Boschelli, *Drugs of the Future* 2000, 25 (7), 717; Talamonti, *J. Clin. Invest.* 1993, 91, 53; Lutz, *Biochem. Biophys. Res.* 1998, 243, 503; Rosen, *J. Biol. Chem.,* 1986, 261, 13754; Bolen, *Proc. Natl. Acad. Sci. USA* 1987, 84, 2251; Masaki, *Hepatology* 1998, 27, 1257; Biscardi, *Adv. Cancer Res.* 1999, 76, 61; Lynch, *Leukemia* 1993, 7, 1416; Wiener, *Clin. Cancer Res.* 1999, 5, 2164; Staley, *Cell Growth Diff,* 1997, 8, 269].

The term "SYK-mediated disease" or "SYK-mediated condition", as used herein, means any disease or other deleterious condition in which SYK protein kinase is known to play a role. Such conditions include, without limitation, allergic disorders, especially asthma.

The term "AUR-mediated disease" or "AUR-mediated condition", as used herein, means any disease or other deleterious condition in which AUR protein kinase is known to play a role. Such conditions include, without limitation, allergic disorders, especially asthma.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting a protein kinase (e.g., PDK-1, FMS, c-KIT, GSK-3, CDK-2, SRC, JAK-1, JAK-2, JAK-3, TYK-2, FLT-3, KDR, PDGFR, ROCK, SYK, AUR-2, or AUR-3 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of kinase activity, including PDK-1, FMS, c-KIT, GSK-3, CDK-2, SRC, JAK-1, JAK-2, JAK-3, TYK-2, FLT-3, KDR, PDGFR, ROCK, SYK, AUR-1, or AUR-2 kinase activity, in a biological sample is useful for a variety of purposes that are known to one of skill in the art. Examples of such purposes include, but are not limited to, blood transfusion, organ-transplantation, biological specimen storage, and biological assays.

EXAMPLES

Compounds of general formula I were prepared according to the general procedures described in the Schemes and Examples herein.

Tables 2 and 3 below depicts exemplary MS and $^1$H NMR data for certain compounds of the invention:

TABLE 2

| Compound No. | Mpos | Rt | $^1$H NMR |
|---|---|---|---|
| I-42 | 327 | 3.3 | MeOH-d4: 8.8 (s, 1H), 7.8 (d, 2H), 7.5 (d, 2H), 7.4 (t, 1H) 7.0 (s, 2H), 3.9 (s, 6H), 3.7 (s, 3H). |
| I-43 | 338.2 | 3.1 | DMSO-d6: 12.03 (s, 1H), 8.74 (s, 1H), 8.34-8.31 (t, 1H), 7.52 (m, 2H), 7.48 (m, 2H), 7.41-7.38 (m, 1H), 7.14 (s, 1H), 7.13 (s, 1H), 3.94-3.91 (m, 1H), 3.78-3.74 (m, 1H), 3.27-3.24 (m, 2H), 1.82-1.78 (m, 3H), 1.57-1.54 (m, 1H) |
| I-44 | 295.1 | 3.5 | DMSO-d6: 9.15 (m, 1H), 9.0 (m, 1H), 7.80 (d, 2H), 7.52 (t, 2H), 7.32 (t, 1H), 7.27 (d, 1H), 7.02 (d, 1H), 6.75 (d, 1H), 4.2 (m, 4H) |
| I-45 | 281.1 | 3.9 | DMSO-d6: 9.39 (m, 1H), 9.05 (m, 1H), 7.82 (d, 2H), 7.55 (t, 2H), 7.33 (m, 2H), 7.15 (m, 2H), 6.42 (d, 1H), 4.02 (m, 2H), 1.3 (m, 3H) |
| I-46 | 295.1 | | Methanol-d4: 8.75 (s, 1H), 7.79 (d, 2H), 7.53 (m, 4H), 7.37 (t, 1H), 6.9 (d, 1H), 4.5 (m, 1H), 1.32 (d, 6H) |
| I-47 | 281.1 | 3.8 | Methanol-d4: 8.75 (s, 1H), 7.79 (d, 2H), 7.53 (m, 4H), 7.37 (t, 1H), 6.89 (d, 1H), 4.20 (q, 2H), 1.39 (t, 3H) |

TABLE 3

| Compound No. | Mpos | RT | $^1$H NMR |
|---|---|---|---|
| I-43 | 352.1 | 3.28 | DMSO-d6: 9.5 (s, 1H), 9.3 (s, 1H), 8.05 (s, 4H), 7.05 (s, 2H), 3.8 (s, 6H), 3.6 (s, 3H). |
| I-49 | 321 | 1.17 | 8.95 (1H, s), 8.12 (1H, d, 5.6 Hz), 7.58 (2H, dd, 8.7, 1.1 Hz), 7.28 (2H, dd, 8.7, 7.5 Hz), 7.16 (1H, d, 1.5 Hz), 7.05 (1H, dd, 5.6, 1.7 Hz), 6.92-6.88 (1H, m), 3.62-3.60 (4H, m), 1.71-1.64 (6H, m). |
| I-50 | 335 | 1.34 | 8.86 (1H, s), 7.96 (1H, d, 5.6 Hz), 7.60 (2H, dd, 8.8 Hz, 1.0 Hz), 7.27 (2H, dd, 8.8 Hz, 7.5 Hz), 6.95-6.88 (3H, m), 3.73-3.65 (1H, m), 2.04-2.00 (2H, m), 1.81-1.77 (3H, m), 1.69-1.65 (1H, m), 1.49-1.39 (2H, m), 1.31-1.21 (2H, m). |
| I-51 | 311 | 1.5 | 8.39 (1H, s), 8.11 (1H, d, 5.6 Hz), 7.53 (2H, t, 8.1 Hz), 7.34 (2H, t, 8.0 Hz), 6.98 (1H, t, 7.3 Hz), 6.86 (1H, s), 6.83 (1H, dd, 5.6, 1.5 Hz), 6.77 (1H, s), 3.90-3.84 (2H, m), 3.82-3.76 (2H, m), 3.16 (3H, s). |
| I-52 | 349 | 1.73 | 8.37 (1H, s), 8.20 (1H, d, 5.4 Hz), 7.54 (2H, dd, 8.9, 1.1 Hz), 7.33 (2H, dd, 8.6, 7.6 Hz), 6.99-6.95 (1H, m), 6.84 (1H, s), 6.80 (1H, d, 1.7 Hz), 6.73 (1H, dd, 5.6, 1.7 Hz), 3.68-3.66 (4H, m), 1.86-1.80 (4H, m), 1.62-1.57 (4H, m), 1.55-1.51 (2H, m). |
| I-53 | 352 | 1.43 | 8.39 (1H, s), 8.18 (1H, d, 5.6 Hz), 7.53 (2H, dd, 8.6, 1.0 Hz), 7.33 (2H, t, 8.0 Hz), 6.99-6.95 (1H, m), 6.89 (1H, d, 1.5 Hz), 6.77 (2H, dd, 5.6, 1.7 Hz), 3.62 (2H, t, 7.2 Hz), 3.12 (3H, s), 2.31 (2H, t, 7.0 Hz), 2.23 (6H, s), 1.79 (2H, quin, 7.1 Hz). |
| I-54 | 325 | 1.52 | 8.38 (1H, s), 8.09 (1H, d, 5.6 Hz), 7.53 (2H, d, 8.3 Hz), 7.34 (2H, t, 7.8 Hz), 6.98 (1H, t, 7.4 Hz), 6.89 (1H, d, 1.5 Hz), 6.79 (1H, dd, 5.9, 1.7 Hz), 6.77 (1H, br s), 3.87-3.85 (2H, m), 3.75-3.73 (2H, m), 3.53 (2H, q, 7.1 Hz), 1.27 (3H, t, 7.1 Hz). |
| I-55 | 357 | 1.3 | 9.53 (1H, s), 9.23 (1H, s), 8.17 (1H, d, 5.6 Hz), 7.59 (2H, dd, 8.6 Hz, 0.9 Hz), 7.34-7.21 (7H, m), 7.07 (1H, dd, 5.6, 1.7 Hz), 7.00 (1H, d, 1.5 Hz), 6.85 (1H, t, 7.3 Hz), 4.85 (2H, s), 3.12 (3H, s). |
| I-56 | 321 | 1.29 | 8.37 (1H, s), 8.19 (1H, d, 5.6 Hz), 7.53 (2H, dd, 8.6, 1.0 Hz), 7.33 (2H, dd, 8.6, 7.6 Hz), 6.99-6.95 (1H, m), 6.75-6.74 (2H, m), 6.67 (1H, d, 1.7 Hz), 3.66-3.59 (1H, m), 2.15-2.00 (3H, m), 1.79-1.73 (1H, m), 1.26 (3H, d, 6.1 Hz). |
| I-57 | 358 | 0.94 | 8.56 (1H, d, 1.5 Hz), 8.51 (1H, dd, 4.8, 1.6 Hz), 8.38 (1H, s), 8.22 (1H, dd, 5.6, 0.5 Hz), 7.56-7.62 (1H, m), 7.51 (2H, dd, 8.7, 1.1 Hz), 7.33 (2H, dd, 8.4, 7.5 Hz), 7.23 (1H, dd, 7.8, 4.6 Hz), 6.95-7.00 (1H, m), 6.80-6.89 (3H, m), 4.92 (2H, s), 3.13 (3H, s). |
| I-58 | 339 | 1.11 | 9.13 (1H, s), 7.97 (1H, d, 6.9 Hz), 7.61-7.59 (2H, m), 7.45 (1H, s), 7.39 (1H, dd, 7.1, 2.0 Hz), 7.31-7.27 (2H, m), 6.96-6.92 (1H, m), 3.88 (2H, t, 4.7 Hz), 3.79 (2H, t, 4.8 Hz), 3.65-3.61 (2H, m), 1.84-1.75 (2H, m), 1.07 (3H, t, 7.3 Hz). |
| I-59 | 325 | 1.08 | 9.14 (1H, s), 7.96 (1H, d, 7.3 Hz), 7.60-7.58 (2H, m), 7.51 (1H, d, 1.7 Hz), 7.43 (1H, dd, 7.1, 2.0 Hz), 7.29 (2H, dd, 8.7, 7.5 Hz), 6.96-6.92 (1H, m), 3.87 (2H, t, 4.9 Hz), 3.72 (2H, t, 5.1 Hz), 3.39 (3H, s), 3.31 (3H, s). |
| I-60 | 352 | 0.95 | 8.88 (1H, s), 8.01 (1H, d, 5.6 Hz), 7.60 (2H, dd, 8.7, 1.1 Hz), 7.27 (2H, dd, 8.7, 7.5 Hz), 6.99 (1H, dd, 5.9, 1.7 Hz), 6.97 (1H, d, 1.7 Hz), 6.92-6.88 (1H, m), 3.48-3.44 (2H, m), 2.73 (2H, m), 2.65 (4H, q, 7.2 Hz), 1.09 (6H, t, 7.2 Hz). |

TABLE 3-continued

| Compound No. | Mpos | RT | $^1$H NMR |
|---|---|---|---|
| I-61 | 406 | 1 | 9.07 (1H, s), 8.04 (1H, d, 6.9 Hz), 7.62 (2H, dd, 8.8, 1.0 Hz), 7.38-7.34 (2H, m), 7.29 (2H, dd, 8.6, 7.3 Hz), 6.96-6.92 (1H, m), 4.44-4.36 (1H, m), 2.90 (3H, s), 2.37 (2H, dd, 14.2, 3.7 Hz), 1.89 (2H, t, 13.0 Hz), 1.62 (6H, s), 1.53 (6H, s). |
| I-62 | 337 | 1.36 | 9.55 (1H, s), 9.23 (1H, s), 8.14 (1H, d, 5.6 Hz), 7.63-7.61 (2H, m), 7.25 (2H, dd, 8.4, 7.5 Hz), 7.01 (1H, dd, 5.6, 1.7 Hz), 6.93 (1H, d, 1.5 Hz), 6.87-6.83 (1H, m), 3.58-3.54 (2H, m), 3.04 (3H, s), 1.64-1.54 (1H, m), 1.47-1.41 (2H, m), 0.95 (6H, d, 6.7 Hz). |
| I-63 | 453 | 1.24 | 10.85 (1H, s), 9.54 (1H, s), 9.29 (1H, s), 8.23 (1H, d, 5.5 Hz), 7.62 (2H, dd, 8.7, 0.9 Hz), 7.29-7.25 (3H, m), 7.16-7.11 (2H, m), 6.93-6.93 (3H, m), 6.87-6.83 (1H, m), 4.60 (2H, d, 13.5 Hz), 4.52-4.44 (1H, m), 3.04 (2H, t, 12.6 Hz), 2.39-2.28 (2H, m), 1.78 (2H, d, 12.1 Hz). |
| I-64 | 420 | 1.1 | 9.13 (1H, s), 8.06 (1H, d, 6.6 Hz), 7.58 (2H, dd, 8.6, 1.2 Hz), 7.48 (1H, d, 1.7 Hz), 7.45 (1H, dd, 6.6, 2.0 Hz), 7.30 (2H, dd, 8.6, 7.4 Hz), 6.96-6.92 (1H, m), 4.77 (1H, dd, 7.6, 6.1 Hz), 3.98-3.71 (10H, m), 2.19-2.12 (2H, m), 2.00-1.93 (2H, m). |
| I-65 | 351.1 | 2.04 | 1H NMR (500 MHz, CDCl3) d 8.31 (1H, s), 8.10 (1H, d), 7.45 (2H, d), 7.28 (2H, t), 6.91 (2H, m), 6.89 (1H, s), 6.71 (1H, d), 3.79 (2H, m), 3.50 (3H, m), 3.35 (1H, m), 1.84 (2H, m), 1.67 (1H, m), 1.52 (1H, m), 1.38 (1H, m) ppm. |
| I-66 | 378.1 | 1.96 | 1H NMR (500 MHz, CDCl3) d 8.31 (1H, s), 8.10 (1H, t), 7.45 (2H, d), 7.25 (2H, t), 6.90 (1H, t), 6.81 (1H, s), 6.79 (1H, d), 6.72 (1H, d), 3.88 (1H, t), 3.73 (2H, m), 3.61 (2H, m), 3.43 (1H, m), 3.37 (1H, m), 2.01-1.90 (5H, m) ppm. |
| I-67 | 392.1 | 2.08 | 1H NMR (500 MHz, MeOD) d 9.25 (1H, m), 8.0 (1H, d), 7.60 (2H, d), 7.50 (2H, t), 7.32 (2H, t), 6.98 (1H, t), 3.92 (4H, m), 3.75-3.50 (4H, m), 2.40 (2H, m), 1.10 (5H, m) ppm. |
| I-68 | 406.1 | 2.32 | 1H NMR (500 MHz, CDCl3) d 8.30 (1H, d), 8.12 (1H, t), 7.43 (2H, d), 7.24 (2H, t), 6.92 (2H, t), 6.84 (1H, d), 6.80 (1H, s), 6.72 (1H, d), 3.90 (1H, m), 3.76 (3H, m), 3.61 (2H, m), 3.45-3.33 (2H, m), 2.21 (2H, m), 1.52 (2H, m), 0.84 (3H, m) ppm |
| I-69 | 406.1 | 2.28 | 1H NMR (500 MHz, CDCl3) d 8.34 (1H, d), 8.11 (1H, t), 7.44 (2H, d), 7.24 (2H, t), 6.91 (2H, t), 6.76 (2H, m), 6.69 (1H, m), 3.89 (1H, m), 3.72 (3H, m), 3.61 (2H, m), 3.41 (2H, m), 2.69 (1H, m), 1.91 (2H, m), 1.01 (3H, d), 0.95 (3H, d) ppm |
| I-70 | 420.1 | 2.48 | 1H NMR (500 MHz, CDCl3) d 8.31 (1H, d), 8.11 (1H, t), 7.44 (2H, d), 7.28 (2H, t), 7.0 (1H, d), 6.90 (1H, t), 6.79 (1H, d), 6.74 (1H, d), 3.89 (1H, m), 3.72 (3H, m), 3.61 (2H, m), 3.41 (2H, m), 2.12 (2H, m), 1.95 (3H, m), 0.89 (6H, d) ppm |
| I-71 | 408 | 2 | 1H NMR (500 MHz, CDCl3) d 8.31 (1H, d), 8.11 (1H, t), 7.44 (2H, d), 7.29 (2H, t), 76.90 (1H, t), 6.80 (2H, m), 6.74 (1H, t), 4.05 (2H, s), 3.89 (1H, m), 3.72 (3H, m), 3.61 (2H, m), 3.41 (2H, m), 3.30 (3H, s), 1.95 (2H, m) ppm |
| I-72 | 403 | 2.04 | 1H NMR (500 MHz, MeOD-d4) d 8.94 (1H, m), 8.12 (1H, dd), 7.58 (2H, d), 7.27 (2H, t), 7.09 (2H, d), 6.90 (1H, t), 3.99 (1H, t), 3.90-3.77 (5H, m), 3.69 (1H, t), 3.60-3.40 (3H, m), 2.0 (2H, m) ppm. |
| I-73 | 335.00, 335.00 | 2.27, 1.21 | 1H NMR (500 MHz, CDCl3) d 8.30 (1H, s), 8.10 (1H, d), 7.50 (2H, m), 7.30 (3H, m), 6.90 (1H, t), 6.70 (1H, s), 6.65 (1H, d), 3.60 (4H, m), 1.70-1.50 (8H, m) ppm, 8.93 (1H, s), 8.08 (1H, d, 6.1 Hz), 7.58 (2H, dd, 8.8, 1.0 Hz), 7.27 (2H, dd, 8.6, 7.3 Hz), 7.00-6.97 (2H, m), 6.92-6.88 (1H, m), 3.70-3.67 (4H, m), 1.90-1.79 (4H, m), 1.61-1.56 (4H, m). |
| I-74 | 392 | 2.32 | 1H NMR (500 MHz, CDCl3) d 8.35 (1H, s), 8.15 (1H, d), 7.48 (2H, d), 7.30 (2H, t), 6.92 (3H, m), 6.79 (1H, d), 3.30 (2H, m), 3.10 (2H, m), 2.10 (3H, s), 1.95 (2H, m), 1.30 (6H, d) ppm |
| I-75 | 464.1 | 2.68 | 1H NMR (500 MHz, CDCl3) d 8.44 (1H, s), 8.22 (1H, d), 8.05 (2H, d), 7.61 (3H, m), 7.27 (1H, s), 7.02 (1H, s), 6.86 (1H, d), 4.40 (2H, q), 3.50 (2H, q), 3.40 (2H, m), 3.20 (2H, m), 2.20 (3H, s), 1.40 (6H, m), 1.20 (3H, t) ppm. |
| I-76 | 450.1 | 2.28 | 1H NMR (500 MHz, CDCl3) d 8.35 (1H, d), 8.12 (1H, t), 7.99 (2H, d), 7.50 (2H, d), 7.34 (1H, m), 6.80 (1H, d), 6.72 (1H, d), 4.30 (2H, q), 3.90 (1H, m), 3.73 (3H, m), 3.61 (2H, m), 3.41 (1H, m), 3.35 (2H, m), 2.05 (2H, m), 1.95 (3H, s), 1.30 (3H, t) ppm. |
| I-77 | 478.1 | 1.92 | 1H NMR (500 MHz, CDCl3) d 8.31 (1H, s), 8.13 (1H, d), 7.40 (2H, d), 7.30 (2H, t), 6.95 (1H, s), 6.82 (1H, d), 6.70 (1H, s), 6.18 (1H, s), 4.15 (2H, m), 3.10 (2H, m), 2.99 (6H, s), 2.90 (2H, m), 2.10 (3H, s), 1.35 (6H, d) ppm. |
| I-78 | 465.3 | 2.06 | 1H NMR (500 MHz, CDCl3) d 8.30 (1H, s), 8.12 (1, d), 7.41 (2H, d), 7.29 (2H, m), 6.93 (1H, s), 6.75 (2H, m), 6.51 (1H, s), 4.15 (2H, m), 3.70 (3H, s), 3.30 (2H, m), 3.10 (2H, m), 2.05 (3H, s), 1.29 (6H, d) ppm. |

TABLE 3-continued

| Compound No. | Mpos | RT | $^1$H NMR |
|---|---|---|---|
| I-79 | 503.3 | 2.42 | 1H NMR (500 MHz, DMSO-d6) d 9.60 (1H, s), 9.28 (1H, s), 8.20 (1H, d), 7.65 (2H, d), 7.55 (2H, d), 7.25 (1H, s), 7.12 (1H, d), 4.05 (2H, m), 3.18 (2H, m), 3.05 (2H, m), 2.05 (3H, s), 1.2 (6H, m) ppm. |
| I-80 | 517.2 | 2.4 | 1H NMR (500 MHz, MeOD-d4) d 8.95 (1H, s), 8.18 (1H, d), 7.69 (1H, m), 7.50 (5H, m), 7.25 (1H, s), 7.15 (2H, m), 4.30 (2H, m), 3.30 (2H, m), 3.15 (2H, m), 2.20 (3H, m), 1.35 (6H, m) ppm. |
| I-81 | 501.3 | 2.2 | 1H NMR (500 MHz, MeOD-d4) d 8.95 (1H, s), 8.18 (1H, d), 7.72 (1H, m), 7.61 (4H, m), 7.25 (2H, m), 7.15 (1H, m), 6.61 (1H, s), 4.30 (2H, m), 3.30 (2H, m), 3.15 (2H, m), 2.20 (3H, s), 1.35 (6H, m) ppm. |
| I-82 | 407.3 | 0.54 | 1H NMR (500 MHz, CDCl3) d 8.39 (1H, s), 8.10 (1H, d), 7.22 (2H, d), 7.15 (2H, d), 6.95 (1H, s), 6.92 (2H, m), 6.75 (1H, m), 6.65 (2H, d), 4.15 (2H, m), 3.08 (2H, m), 2.99 (2H, m), 2.10 (3H, s), 1.30 (6H, m) ppm. |
| I-83 | 379.3 | 2.8 | DMSO-d6: 9.60 (s, 1H); 9.10 (s, 1H); 8.40 (d, 1H); 7.60 (d, 2h); 7.28 (d, 2H); 6.82 (dd, 1H); 6.78 (m, 1H); 4.00-3.55 (m, 5H); 3.45 (m, 2H); 2.00-1.75 (m, 5H); |
| I-84 | 351.3 | 1.8 | DMSO-d6: 9.60 (s, 1H); 9.42 (bs, 1H); 9.15 (s, 1H); 8.80 (bs, 1H); 8.45 (s, 1H); 7.66 (d, 2H); 7.28 (dd, 2H); 7.12 (s, 1H); 6.86 (dd, 1H); 4.65 (m, 2H); 3.40 (m, 2H); 3.00 (m, 2H); 1.25 (m, 6H) |
| I-85 | 477.3 | 1.78 | 1H NMR (500 MHz, DMSO-d6) d 9.26 (1H, s), 9.21 (1H, s), 8.20 (1H, d), 7.52 (2H, d), 7.21 (1H, s), 7.12 (1H, d), 6.90 (2H, d), 4.30 (2H, m), 4.05 (2H, m), 3.73 (4H, m), 3.09 (2H, m), 2.99 (4H, m), 2.51 (3H, s), 1.2 (6H, m) ppm. |
| I-86 | 393.3 | 3 | DMSO-d6: 9.56 (s, 1H); 9.12 (s, 1H); 8.42 (s, 1H); 7.60 (d, 2H); 7.26 (dd, 2H); 6.98 (s, 1h); 6.86 (dd, 2h); 4.60-4.10 (m, 4H); 3.18 (m, 2H); 2.02 (s, 3h); 1.18 (m, 6H) |
| I-87 | 479.3 | 2.3 | DMSO-d6: 9.42 (s, 1H); 9.30 (bs, 1H); 9.28 (s, 1H); 8.15 (d, 1H); 7.50 (d, 2h); 7.31 (d, 2H); 7.25 (s, 1H); 7.15 (d, 1H); 4.25 (m, 4H); 4.10 (q, 2H); 3.18 (m, 2H); 2.02 (s, 3H); 1.20 (t, 3H); 1.18 (m, 6H) |
| I-88 | 493.3 | 2.5 | DMSO-d6: 9.42 (s, 1H); 9.30 (bs, 1H); 9.28 (s, 1H); 8.15 (d, 1H); 7.50 (d, 2h); 7.31 (d, 2H); 7.25 (s, 1H); 7.15 (d, 1H); 4.25 (m, 4H); 4.00 (q, 2H); 3.18 (m, 2H); 2.02 (s, 3h); 1.60 (m, 2H); 1.18 (m, 6H); 0.85 (t, 3H) |
| I-89 | 493.3 | 2.5 | DMSO-d6: 9.38 (s, 1H); 9.28 (s, 1H); 9.22 (bs, 1H); 8.15 (d, 1H); 7.50 (d, 2h); 7.31 (d, 2H); 7.25 (s, 1H); 7.15 (d, 1H); 4.86 (m, 1H); 4.25 (m, 4H); 3.18 (m, 2H); 2.02 (s, 3H); 1.20 (d, 6H); 1.18 (m, 6H); |
| I-90 | 507.3 | 2.7 | DMSO-d6: 9.42 (s, 1H); 9.32 (bs, 1H); 9.228 (s, 1H); 8.15 (d, 1H); 7.50 (d, 2h); 7.31 (d, 2H); 7.25 (s, 1H); 7.15 (d, 1H); 4.25 (m, 4H); 3.80 (m, 2H); 3.18 (m, 2H); 2.02 (s, 3H); 1.88 (m, 1H); 1.18 (m, 6H); 0.86 (d, 6H) |
| I-91 | 521.3 | 2.9 | DMSO-d6: 9.42 (s, 1H); 9.32 (bs, 1H); 9.228 (s, 1H); 8.15 (d, 1H); 7.50 (d, 2h); 7.31 (d, 2H); 7.25 (s, 1H); 7.15 (d, 1H); 4.24 (m, 4H); 3.75 (s, 2H); 3.18 (m, 2H); 2.02 (s, 3H); 1.18 (m, 6H); 0.86 (s, 9H) |
| I-92 | 630.4 | 2.98 | 1H NMR (500 MHz, CDCl3) d 8.28 (1H, s), 8.11 (1H, d), 7.60 (2H, d), 7.32 (2H, d), 7.25 (2H, d), 6.90 (1H, s), 6.80 (2H, d), 6.75 (1H, m), 6.55 (1H, s), 4.25 (2H, m), 3.10 (10H, m), 2.35 (3H, s), 2.10 (3H, s), 1.28 (6H, m) ppm. |
| I-93 | 363 | 3.6 | 500 MHz DMSO-d6: 10.6 (s ex, H), 9.6 (s ex, 1H), 9.25 (s, 1H), 8.55 (s, 1H), 8.4 (d, 1H); 7.63 (d, 2H). 7.58 (d, 1H), 7.3 (t, 2H), 6.85 (t, 1H), 1.85 (d, 2H), 1.76 (d, 2H), 1.66 (d, 1H), 1.4 (dt, 2H), 1.25 (m, 4H) |
| I-94 | 363 | 3.7 | 500 MHz DMSO-d6: 10.6 (s ex, 1H), 9.6 (s, ex, 1H), 9.25, (s, 1H), 8.57 (s, 1H), 8.35 (d, 1H), 7.65 (d, 2H), 7.59 (d, 1H), 7.25 (t, 2H), 6.85 (t, 1H), 2.4 (d, 2H), 2.24 (quin, H), 1.75 (m, 2H), 1.6 (M, 2H), 1.54 (M, 2H), 1.18 (m, 2H) |
| I-95 | 385 | 3.7 | 500 MHz DMSO-d6: 10.7 (s ex, 1H), 9.6 (s ex, 1H) 9.23, (s, 1H), 8.54 (s, 1H), 8.4 (d, 1H); 7.62 (d, 2H), 7.56 (d, 1H), 7.25 (m, 6H), 7.15 (t, 1H), 2.95 (t, 2H), 2.75 (t, 2H) |
| I-96 | 371 | 3.5 | 500 MHz DMSO-d6: 10.9 (s ex, 1H), 9.57 (s ex, 1H), 9.2, (s.1H), 8.5 (d, 1H), 8.38 (d, 1H), 7.6 (d, 2H), 7.3 (m, 4H), 7.25, (m, 4H), 6.85 (t, 1H), 3.75 (s, 2H) |
| I-97 | 576.4 | 2.58 | 1H NMR (500 MHz, MeOD-d4) d 8.95 (1H, s), 8.15 (1H, d), 7.50 (2H, d), 7.20 (1H, s), 7.10 (1H, d), 6.95 (2H, m), 4.31 (3H, m), 3.55 (4H, m), 3.15 (2H, m), 3.05 (3H, m), 2.18 (3H, s), 1.45 (9H, s), 1.35 (6H, m) ppm. |
| I-98 | 478.4 | 1.95 | DMSO-d6: 9.32 (s, 1H); 9.28 (s, 1H); 8.18 (d, 1H); 8.12 (s, 1H); 7.48 (d, 2H); 7.28 (m, 3H); 7.12 (m, 1H); 5.92 (m, 1H); 4.50-4.00 (m, 4H); 3.10 (m, 4H); 2.02 (s, 3H); 1.20 (m, 6H); 1.02 (t, 3H) |

TABLE 3-continued

| Compound No. | Mpos | RT | ¹H NMR |
|---|---|---|---|
| I-99 | 492.4 | 2.12 | DMSO-d6: 9.32 (s, 1H); 9.28 (s, 1H); 8.18 (d, 1H); 8.12 (s, 1H); 7.48 (d, 2H); 7.28 (m, 3H); 7.12 (m, 1H); 5.92 (m, 1H); 4.50-4.00 (m, 4H); 3.10 (m, 4H); 2.02 (s, 3H); 1.40 (m, 2H); 1.20 (m, 6H); 1.02 (t, 3H) |
| I-100 | 492.4 | 2.11 | DMSO-d6: 9.32 (s, 1H); 9.28 (s, 1H); 8.18 (d, 1H); 8.12 (s, 1H); 7.48 (d, 2H); 7.28 (m, 3H); 7.12 (m, 1H); 5.92 (m, 1H); 4.50-4.00 (m, 4H); 3.75 (m, 1H); 3.10 (m, 4H); 2.02 (s, 3H); 1.20 (m, 6H); 1.08 (d, 6H) |
| I-101 | 506.4 | 2.35 | DMSO-d6: 9.32 (s, 1H); 9.28 (s, 1H); 8.18 (d, 1H); 8.12 (s, 1H); 7.48 (d, 2H); 7.28 (m, 3H); 7.12 (m, 1H); 5.92 (m, 1H); 4.50-4.00 (m, 4H); 3.10 (m, 4H); 2.02 (s, 3H); 1.22 (s, 9H); 1.20 (m, 6H) |
| I-102 | 351 | 3.5 | 500 MHz DMSO-d6: 10.5 (s ex, 1H), 9.58 (s ex, 1H), 9.21 (s, 1H), 8.6 (d, 1H), 8.35 (d, 1H), 7.62 (d, 2H), 7.58 (d, 1H), 7.27 (t, 2H), 6.87 (t, 1H), 2.3 (s, 2H), 1.0 (s, 9H) |
| I-103 | 337 | 3.43 | (400 MHz, MeOH-d4): 1.60-1.80 (1H, m), 1.90-2.00 (1H, m), 2.05-2.20 (2H, m), 2.95-3.10 (2H, m), 3.3-3.4 (1H, m), 3.6-3.7 (1H, m), 4.3-4.4 (1H, m), 6.90-7.00 (2H, m), 7.25-7.35 (2H, t), 7.65-7.70 (2H, d), 8.45 (1H, s), 9.05 (1H, s) |
| I-104 | 415.51 | 2.84 | 1H NMR (DMSO): 1.60 (2H, m), 1.85 (1H, m), 1.99 (1H, m), 3.18 (3H, m), 3.93 (1H, m), 4.43 (1H, m), 7.16 (2H, br s), 7.19 (1H, d, J = 5.5), 7.26 (1H, s), 7.74 (4H, s), 7.97 (3H, m), 8.24 (1H, d, J = 5.5), 9.34 (1H, s), 10.10 (1H, s) |
| I-105 | 323.1 | 2.4 | DMSO-d6: 11.05 (s, 1H), 9.28 (s, 1H), 7.95 (d, 1H), 7.85 (d, 2H), 7.58 (t, 2H), 7.43 (t, 1H), 7.10 (bs, 1H), 3.80 (m, 4H), 3.53 (m, 4H) |
| I-106 | 322.1 | 3.2 | DMSO-d6: 9.25 (bs, 1H), 9.03 (s, 1H), 7.82 (d, 2H), 7.56 (m, 4H), 7.35 (t, 1H), 7.04 (m, 2H), 3.79 (m, 4H), 3.12 (m, 4H) |
| I-107 | 366.26 | 1.43 | Methanol-d4: 8.92 (s, 1H), 7.83 (d, 2H), 7.74 (d, 1H), 7.55 (m, 3H), 7.43 (t, 1H), 6.89 (s, 1H), 3.9 (m, 4H), 3.78 (t, 2H), 3.38 (m, 2H), 3.29 (m, 4H) |
| I-125 | 349 | 1.32 | 9.13 (1H, s), 7.97 (1H, d, 6.9 Hz), 7.62-7.60 (2H, m), 7.43 (1H, d, 1.7 Hz), 7.38 (1H, dd, 7.0, 1.8 Hz), 7.29 (2H, dd, 8.7, 7.6 Hz), 6.96-6.92 (1H, m), 3.66-3.62 (2H, m), 3.57 (2H, d, 6.6 Hz), 1.84-1.74 (2H, m), 1.21-1.14 (1H, m), 1.06 (3H, t, 7.5 Hz), 0.71-0.67 (2H, m), 0.49-0.45 (2H, m). |
| I-126 | 335 | 1.24 | 8.94 (1H, s), 8.12 (1H, d, 5.6 Hz), 7.58 (2H, dd, 8.7, 1.1 Hz), 7.28 (2H, dd, 8.6, 7.6 Hz), 7.12 (1H, d, 1.5 Hz), 7.03 (1H, dd, 5.6, 1.7 Hz), 6.92-6.88 (1H, m), 4.73-4.67 (1H, m), 4.14-4.06 (1H, m), 3.07-3.00 (1H, m), 1.84-1.75 (2H, m), 1.72-1.65 (2H, m), 1.28-1.11 (5H, m). |
| I-127 | 426 | 1.28 | 9.55 (1H, s), 9.29 (1H, s), 8.21 (1H, d, 5.4 Hz), 7.60-7.65 (2H, m), 7.28 (2H, dd, 8.4, 7.5 Hz), 7.22 (1H, d, 1.5 Hz), 7.08-7.13 (2H, m), 6.86 (1H, t, 7.3 Hz), 6.73-6.78 (2H, m), 6.59 (1H, d, 7.3 Hz), 4.23 (1H, d, 12.5 Hz), 4.13 (1H, d, 12.5 Hz), 4.06 (1H, d, 12.7 Hz), 3.40-3.43 (1H, m), 3.19-3.26 (1H, m), 3.07-3.15 (1H, m), 2.26 (3H, s), 0.97 (3H, d, 6.4 Hz). |
| I-128 | 365 | 1 | 9.53 (1H, s), 9.13 (1H, s), 8.04 (1H, d, 5.9 Hz), 7.62 (2H, d, 7.8 Hz), 7.27 (2H, t, 7.8 Hz), 6.98 (1H, dd, 5.7, 1.6 Hz), 6.94-6.83 (3H, m), 6.29 (1H, s), 3.44-3.37 (4H, m), 3.25-3.17 (4H, m). |
| I-129 | 313 | 1.08 | 9.00 (1H, s), 8.46 (1H, d, 5.6 Hz), 7.73 (1H, d, 2.0 Hz), 7.62-7.52 (3H, m), 7.33-7.24 (2H, m), 6.93-6.89 (1H, m), 3.35 (2H, t, 6.7 Hz), 3.00 (2H, t, 6.7 Hz). |
| I-130 | 338 | 0.98 | 8.88 (1H, s), 8.01 (1H, d, 6.6 Hz), 7.60 (2H, dd, 8.8, 1.0 Hz), 7.29-7.25 (2H, m), 7.01-6.99 (2H, m), 6.92-6.88 (1H, m), 3.47 (2H, t, 6.6 Hz), 3.39 (2H, t, 6.4 Hz), 1.94 (3H, s). |
| I-131 | 354 | 0.91 | 8.87 (1H, s), 8.04-7.96 (1H, m), 7.60 (2H, d, 7.8 Hz), 7.27 (3H, t, 7.9 Hz), 7.00-6.95 (2H, m), 6.90 (1H, t, 7.3 Hz), 3.67 (2H, t, 5.5 Hz), 3.41 (2H, t, 6.7 Hz), 2.79-2.71 (4H, m), 1.91-1.80 (2H, m). |
| I-132 | 323 | 1.25 | 9.54 (1H, s), 9.24 (1H, s), 8.13 (1H, d, 5.5 Hz), 7.62 (2H, dd, 8.6, 1.0 Hz) 7.26 (2H, dd, 8.5, 7.4 Hz), 7.01 (1H, dd, 5.6, 1.7 Hz), 6.93 (1H, d, 1.5 Hz), 6.88-6.83 (1H, m), 3.39 (2H, d, 7.4 Hz), 3.07 (3H, s), 2.09-2.02 (1H, m) 0.89 (6H, d, 6.7 Hz). |
| I-133 | 349 | 1.38 | 9.68 (1H, s), 9.37 (1H, s), 8.14 (1H, d, 6.4 Hz), 7.63 (2H, d, 7.8 Hz), 7.28 (2H, dd, 8.3, 7.3 Hz), 7.24-7.11 (2H, m), 6.88 (1H, t, 7.2 Hz), 4.36-4.14 (1H, m), 2.98 (3H, s), 1.91-1.74 (2H, m), 1.74-1.50 (5H, m), 1.49-1.33 (2H, m), 1.22-1.08 (1H, m). |
| I-134 | 323.27 | 1.91 | DMSO-d6: 9.55 (s, 1H), 9.09 (s, 1H), 8.55 (d, 1H), 7.99 (d, 1H), 7.84 (d, 2H), 7.55 (t, 2H), 7.37 (t, 1H), 7.18 (d, 1H), 3.74 (m, 4H), 3.45 (m, 4H) |
| I-135 | 336.2 | 2.82 | DMSO-d6: 9.88 (s, 1H), 9.32 (s, 1H), 9.07 (s, 1H), 8.55 (d, 1H), 7.94 (d, 1H), 7.84 (d, 2H), 7.55 (t, 2H), 7.35 (t, 1H), 7.02 (d, 1H), 4.25 (m, 2H), 3.5 (m, 2H), 3.1 (m, 4H), 2.85 (s, 3H) |

Aminotriazole Pyrimidines (Refer Also to Scheme 5)

Example 1

1) [1-(6-Chloro-pyrimidin-4yl)-1H-[1,2,4]triazol-3-yl]-phenyl-amine

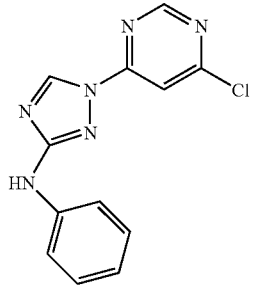

To a suspension of 4,6-dichloro-pyrimidine (292 mg, 1.96 mmol) in 5 ml anhydrous acetonitrile was added phenyl-(1H-[1,2,4]triazol-3-yl)-amine together with diisopropylamine (0.4 ml, 4.0 mmol). The mixture was heated at reflux in a sealed tube overnight. The reaction was cooled to room temperature and the solid was collected by filtration. The solid was washed with cold ether and dried under vacuum. Analytical data: LC/MS showed M+1=273.1, and M−1+271.2, retention time is 3.5 min. NMR in DMSO-d6: 9.78 (s, 1H); 9.28 (s, 1H); 8.90 (s, 1H); 7.90 (s, 1H); 7.65 (d, 2H); 7.28 (dd, 2H); 6.90 (dd, 1H).

2) 1-{4-[6(3-phenylamino-[1,2,4]trazol-1-yl]-[1,4]diazepam-1-yl}-ethanone

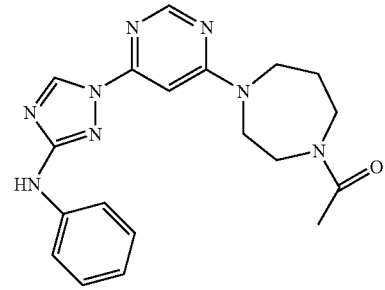

2(I-83)

To a solution of 1 ([1-(6-Chloro-pyrimidin-4yl)-1H-[1,2,4]triazol-3-yl]-phenyl-amine, (27 mg, 0.1 mmol) was added N-acetyl-homopeparazine (150 mg, 1.05 mmol). The reaction was heated in a microwave at 200° C. over 6 min. The reaction was cooled to room temperature and was diluted with ethyl acetate. The mixture was washed with water several times and the organic layer was concentrated, dissolved in DMSO. The material was purified by P-HPLC to give 25 mg of desired product as TFA salt.

Compounds I-84 and I-86 were made in a similar way.

Example 2

Scheme 11 (Scheme i and Compound I-94)

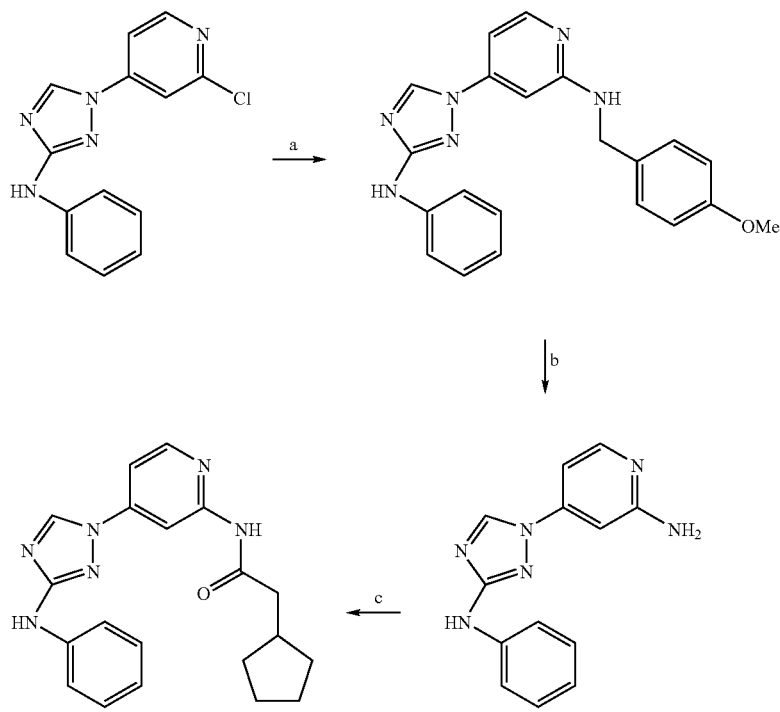

a) p-MeO-benzylamine/NMP (μW) b) TFA/HOAc glacial c) i NMP/DIPEA/RCOCl ii NaOH aqueous

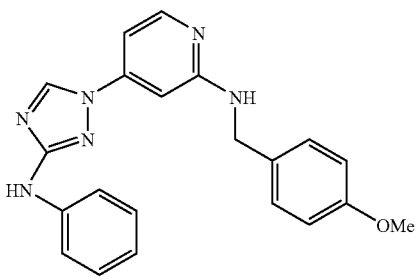

(4-Methoxy-benzyl)-[4-(3-phenylamino-[1,2,4]triazol-1-yl)-pyridin-2-yl]-amine. [1 g, 3.68 mMol] of [1-(2-Chloro-pyridin-4-yl)-1H-[1,2,4]triazol-3-yl]-phenyl-amine was dissolved in 14 mL of NMP with [2.4 mL, 2.52 g, 18.4 mMol] of p-methoxybenzylamine and heated 250 C for 15 min (MW, 150 W). The solvent was removed in vacuo (Kugel-Rohr style) and the residue was treated with MTBE. The ether was decanted away from the dark residue and was replaced with fresh MTBE and mass broken up with vigorous stirring. The ether was again decanted away and replaced with methanol and vigorously stirred for 1 hour. The tan solid was isolated via suction filtration and washed sequentially with methanol and MTBE. The resulting powder was boiled in hot acetonitrile for several minutes, allowed to cool, isolated via suction filtration, and washed with more acetonitrile and finally MTBE. Yield: 0.5 g (38.5%). $^1$H NMR 500 MHz (DMSO-d6) $\partial$ 3.7 (s, 3H), 4.45 (d, 2H), 6.85 (m, 3H), 6.93 (s, 1H), 6.98 (d, 1H), 0.3 (m, 5H), 7.64 (d, 2H), 8.05 (d, 1H), 9.1 (s, 1H), 9.5 (s ex, H). LC/MS [M+H+]=373.

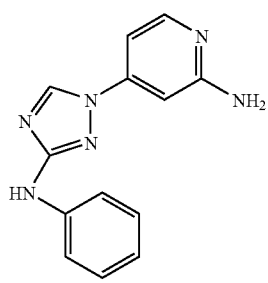

4-(3-Phenylamino-[1,2,4]triazol-1-yl)-pyridin-2-ylamine. [1.5 g, 4.03 mMol] of (4-Methoxy-benzyl)-[4-(3-phenylamino-[1,2,4]triazol-1-yl)-pyridin-2-yl]-amine was dissolved in 25 mL of TFA and stirred at 40 C in a sealed tube for 16 hrs. Then, 10 mL of glacial acetic acid was added and the mixture was stirred at 40 C for an additional 24 hr. The solvent was removed under reduced pressure and the residue triturated with MTBE, The crude material was treated with water and neutralized with 11.4N ammonium hydroxide to pH 9. The resulting solid was isolated via suction filtration and washed with water. This crude product was treated with 0.25N HCl and particulates removed via suction filtration. The filtrates were neutralized with conc. ammonium hydroxide to a pH of 10 and the mixture was extracted with chloroform twice. The organics were combined and washed with water and brine, dried (Na2SO4), and concentrated under reduced pressure. Tan powder collected; 300 mg (33%). $^1$H NMR 500 MHz (DMSO-d6) $\partial$ 6.22 (s ex, 2H), 6.88 (m, 2H), 7.09d, 1H), 7.26 (t, 2H), 7.67 (d, 2H), 7.97 (d, 1H), 9.14 (s, 1H), 9.52 (s ex, 1H). LC/MS [M+H+] 253.

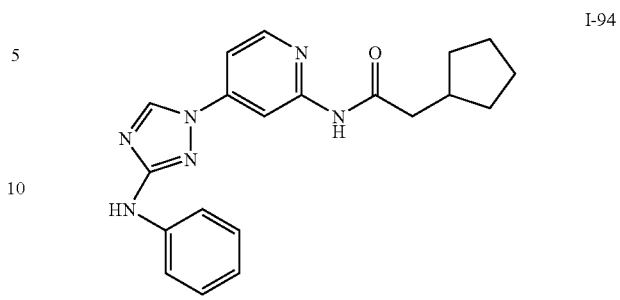

I-94

2-Cyclopentyl-N-[4-(3-phenylamino-[1,2,4]triazol-1-yl)-pyridin-2-yl]-acetamide. 4-(3-Phenylamino-[1,2,4]triazol-1-yl)-pyridin-2-ylamine (50 mg, 0.20 mMol) was dissolved in 2.5 mL of NMP with (50 µL, 67.4 mg, 0.52 mMol) of Hunig's base and (30 µL, 32 mg, 0.2 mMol) of cyclopentylmethyl carbonyl chloride. The reaction was stirred at ambient temperature for 18 hr. LC shows starting material, mono acylated material, and a majority of the bis acylated imide. Another aliquot of the acylating agent was added and the reaction was stirred until all starting material was consumed. Five drops of 2.0N sodium hydroxide was then added and the reaction was stirred for ten hours at ambient temperature, until all of the imide was hydrolyzed. The reaction mixture was acidified with TFA and the crude material was purified via HPLC, C18 silica with a gradient of acetonitrile/water/0.1% TFA as the eluent. Yield ~13 mg of a pale yellow powder as the TFA salt; (18%). $^1$H NMR 500 MHz (DMSO-d6) $\partial$ 1.29m, 2H), 1.5 (m, 2H), 1.77 (m, 2H), 2.25 (m, 1H), 2.4 (d, 2H), 6.88 (t, 1H), 7.28 (t, 2H), 7.53 (d, 1H), 7.63 (d, 2H), 8.35 (d, 1H), 8.55 (d, 1H), 9.2 (s, 1H), 9.57 (s, 1H), 10.6 (s ex, 1H). LC/MS [M+H+] 363

Example 3

Compound I-103

Scheme 12.

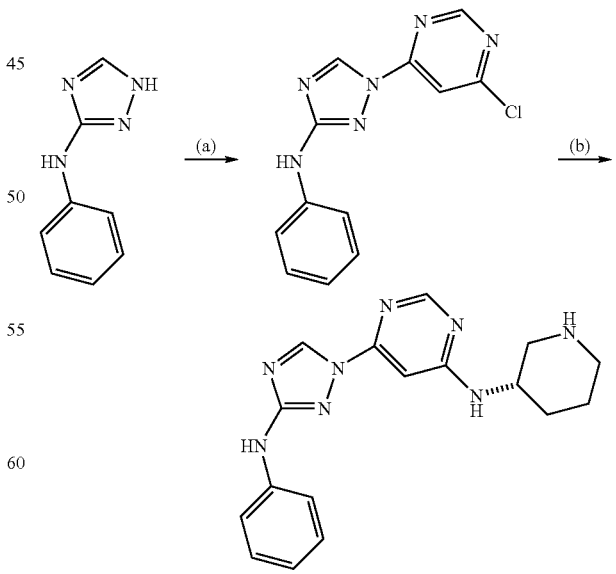

Reagents: (a) Et$_3$N, 4,6 dichloropyrimidine, MeCN, 75° C.; (b) i) (S)-3-amino-Boc-piperidine, DIPEA, dioxane ii) TFA/DCM

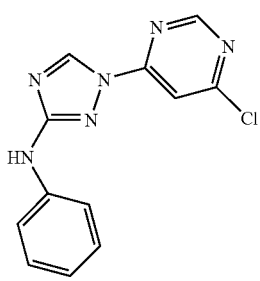

[1-(6-Chloro-pyrimidin-4-yl)-1H-[1,2,4]triazol-3-yl]-phenyl-amine: A suspension of phenylaminotriazole (3.12 mmol), 4,6-dichloropyrimidine (4.1 mmol, 1.3 equivalents) and triethylamine (4.7 mmol, 1.5 equivalents) in acetonitrile (20 ml) was stirred at reflux for eighteen hours. The reaction mixture was partitioned between ethyl acetate and brine. A white precipitate formed and was removed by filtration to afford the title compound which was used without purification in the next step. LC-MS: [MH+] 274.

I-103

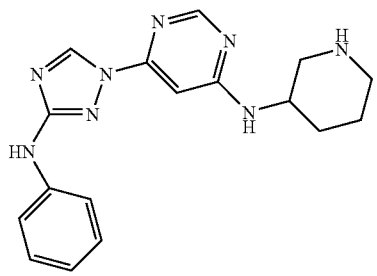

[6-(3-Phenylamino-[1,2,4]triazol-1-yl)-pyrimidin-4-yl]-piperidin-3-yl-amine: To a suspension of [1-(6-Chloro-pyrimidin-4-yl)-1H-[1,2,4]triazol-3-yl]-phenyl-amine (0.25 mmol) in dioxane (5 ml), was added some (S)-3-amino-N-boc-piperidine (1 mmol, 4 equivalents) and DIPEA (1 mmol, 4 equivalents). The reaction mixture was stirred at 80° C. for two hours then 100° C. for eighteen hours. The reaction mixture was diluted with ethyl acetate (50 ml). The organic layer was washed with 10% citric acid, saturated sodium bicarbonate and brine. The organic layer was dried over magnesium sulfate. Filtrated and the organic layer was concentrated in vacuo to afford a pale yellow solid.

The residue was taken up in trifluoroacetic acid/dichloromethane (2 ml/2 ml). The solution was stirred for two hours at room temperature. Purification was carried out by preparative HPLC to afford a white solid as the bis trifluoroacetic acid salt (3.5 mg). (400 MHz, MeOH-d4): 1.60-1.80 (1H, m), 1.90-2.00 (1H, m), 2.05-2.20 (2H, m), 2.95-3.10 (2H, m), 3.3-3.4 (1H, m), 3.6-3.7 (1H, m), 4.3-4.4 (1H, m), 6.90-7.00 (2H, m), 7.25-7.35 (2H, t), 7.65-7.70 (2H, d), 8.45 (1H, s), 9.05 (1H, s); LC_MS: [MH+] 337

Scheme 13 depicts the route used in Examples 4-7 (see also Scheme 6 above).

Scheme 13

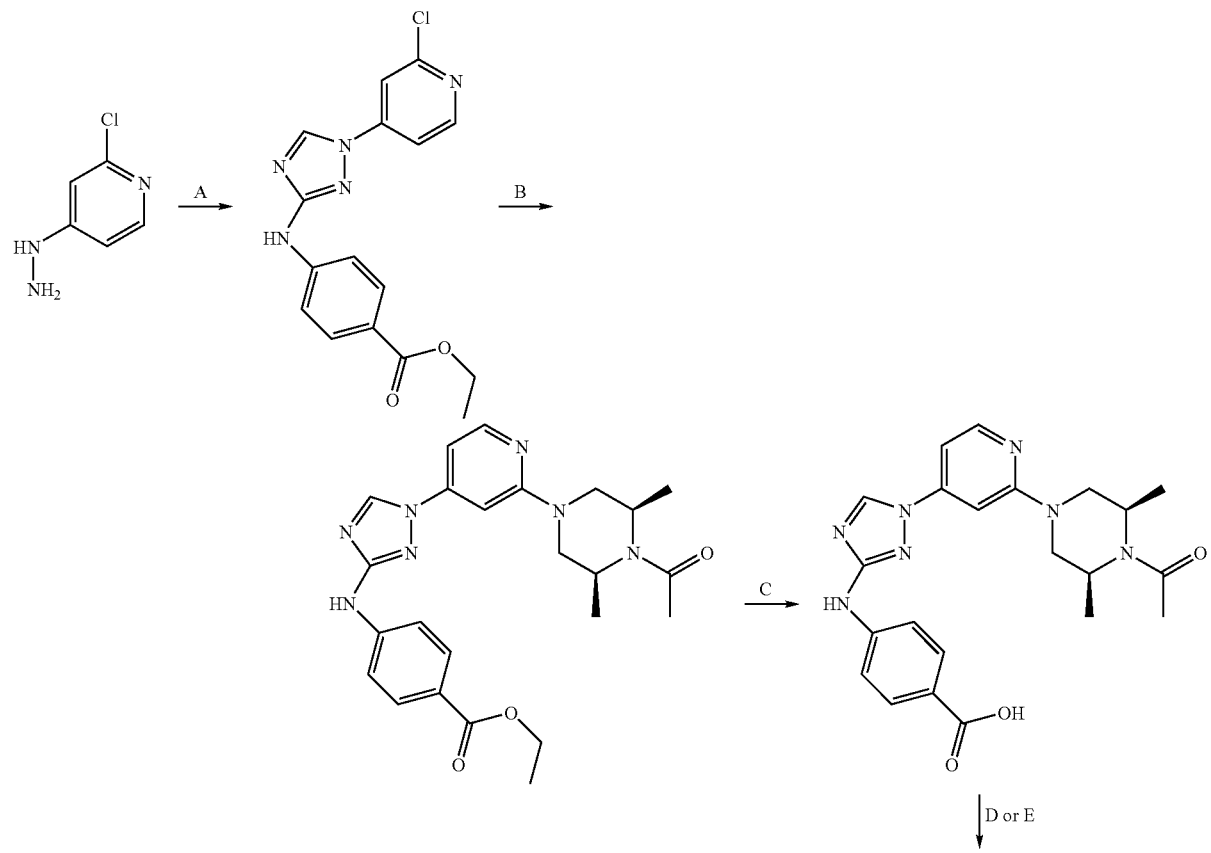

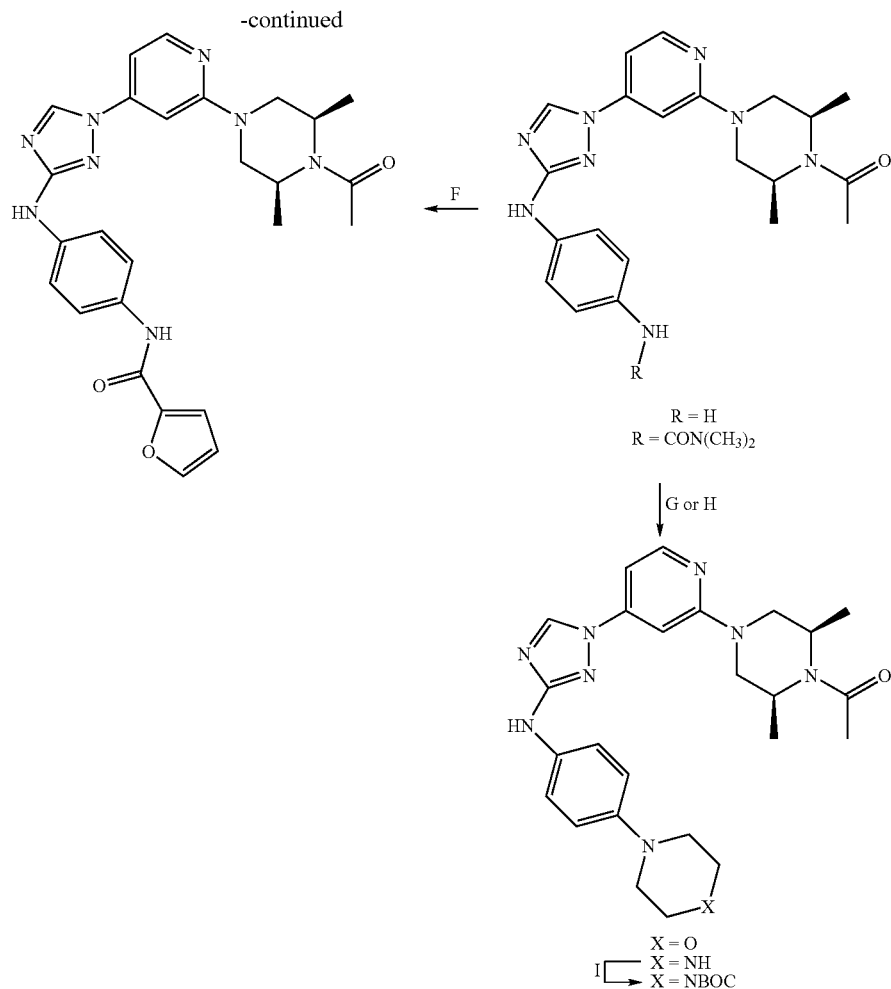

R = H
R = CON(CH₃)₂

G or H

X = O
X = NH
X = NBOC

Example 4

Compound I-77

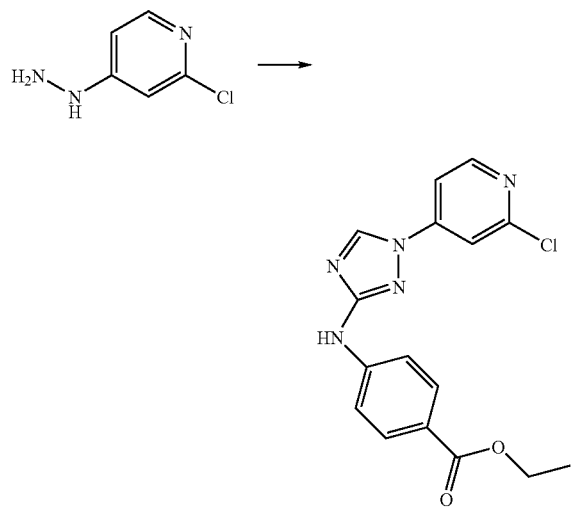

4-[1-(2-Chloro-pyridin-4-yl)-1H-[1,2,4]triazol-3-ylamino]-benzoic acid ethyl ester. To a solution of 1.4 g of (2-Chloro-pyridin-4-yl)-hydrazine (9.79 mMol, 1.51 equiv) in 30 mL of NMP was added sequentially 2.0 g of N-cyano-N'-(4-ethoxycarbonylphenyl)-O-phenylisourea (6.45 mMol, 1.00 equiv) and 10 mL of Hunig's base. The resulting solution was warmed to 220° C. via microwave irradiation for 6 min. The reaction mixture was poured into 100 mL of water and the resulting solid was filtered, yielding 3.0 g of a wet solid, which was dissolved in 40 mL of THF. To the stirred reaction mixture was added 1.50 g of nitrosonium tetrafluoroborate (12.9 mMol, 2.0 equiv). Rapid bubbling was observed and stirring was continued for 1 hr. 4-[1-(2-Chloro-pyridin-4-yl)-1H-[1,2,4]triazol-3-ylamino]-benzoic acid ethyl ester was filtered out of the reaction mixture, yielding 2.0 g (5.83 mMol, 90.4% yield) as a yellow solid. $^1$H NMR (500 MHz, DMSO-d$_6$) δ 10.20 (1H, s), 9.40 (1H, s), 8.52 (1H, d), 8.02 (1 h, s), 7.91 (3H, m), 7.74 (2H, d), 7.15 (1H, br s), 4.27 (2H, q), 1.31 (3H, t) ppm. LC/MS: 3.64 min/344.01 (M+1).

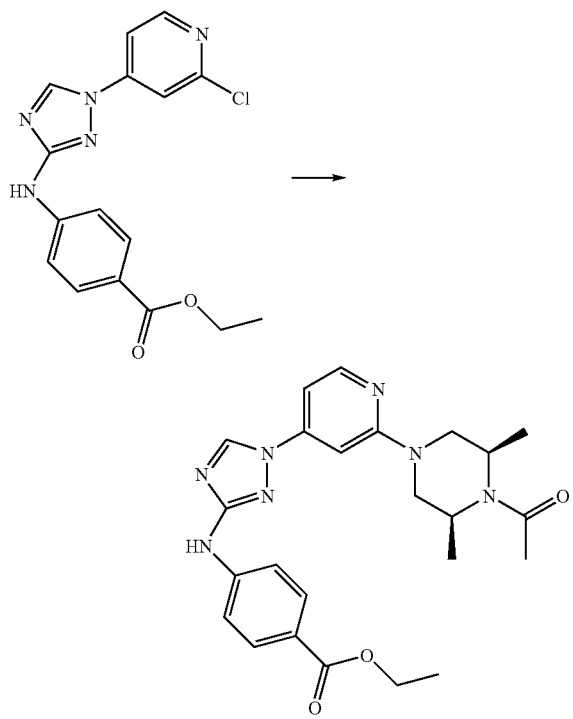

4-{1-[2-(4-Acetyl-3,5-dimethyl-piperazin-1-yl)-pyridin-4-yl]-1H-[1,2,4]triazol-3-ylamino}-benzoic acid ethyl ester. To a solution of 500 mg of 4-[1-(2-Chloro-pyridin-4-yl)-1H-[1,2,4]triazol-3-ylamino]-benzoic acid ethyl ester (1.45 mMol, 1 equiv) in 10 mL of NMP was added 400 mg of cis-3,5 dimethyl piperazine (3.50 mMol, 2.41 equiv). The stirred solution was heated to 250° C. via microwave irradiation for 15 min. The crude product was precipitated by pouring into 100 mL of water and isolated by filtration. The crude product was then redissolved in 10 mL of CH$_2$Cl$_2$ and 2 mL of DMF. To the stirred solution was added sequentially 1 mL of Hunig's base and 500 μL of acetic anhydride. After 3 hr at 25° C., the reaction mixture was concentrated to a dark oil and purified by flash chromatography (10:1 CH$_2$Cl$_2$:MeOH), yielding 300 mg of 4-{1-[2-(4-Acetyl-3,5-dimethyl-piperazin-1-yl)-pyridin-4-yl]-1H-[1,2,4]triazol-3-ylamino}-benzoic acid ethyl ester (0.647 mMol, 44% yield) as a white solid. $^1$H NMR (500 MHz, CDCl$_3$) ∂ 8.44 (1H, s), 8.22 (1H, d), 8.05 (2H, d), 7.61 (3H, m), 7.27 (1H, s), 7.02 (1H, s), 6.86 (1H, d), 4.40 (2H, q), 3.50 (2H, q), 3.40 (2H, m), 3.20 (2H, m), 2.20 (3H, s), 1.40 (6H, m), 1.20 (3H, t) ppm. LC/MS: 2.68 min/464 (M+1).

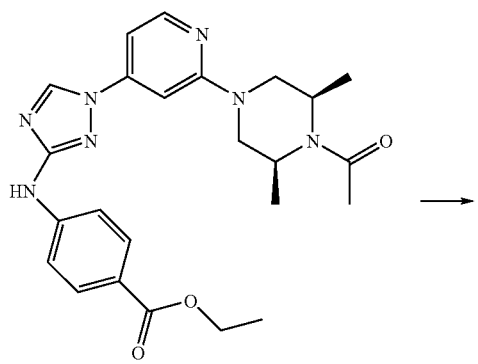

-continued

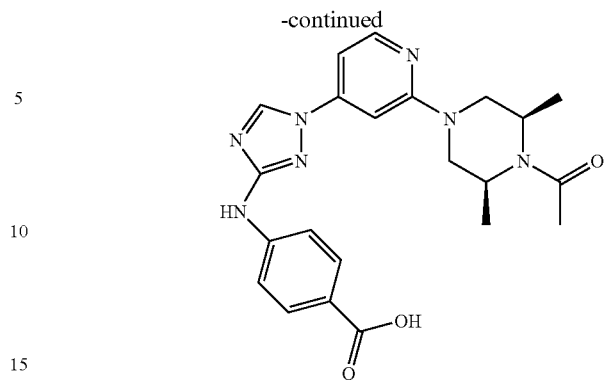

4-{1-[2-(4-Acetyl-3,5-dimethyl-piperazin-1-yl)-pyridin-4-yl]-1H-[1,2,4]triazol-3-ylamino}-benzoic acid. To a solution of 16 g of 4-{1-[2-(4-Acetyl-3,5-dimethyl-piperazin-1-yl)-pyridin-4-yl]-1H-[1,2,4]triazol-3-ylamino}-benzoic acid ethyl ester (34.5 mMol, 1.00 equiv) in 200 mL of 1:1 MeOH:THF was added 5.75 g of lithium hydroxide (137 mMol, 4.00 equiv) in 100 mL of water. The solution was stirred at 60° C. for 12 hr and then the MeOH and THF were removed via rotary evaporation. The basic solution was neutralized by the addition of 68 mL of 2N HCl and the precipitate was isolated by filtration, yielding 12.5 g of 4-{1-[2-(4-Acetyl-3,5-dimethyl-piperazin-1-yl)-pyridin-4-yl]-1H-[1,2,4]triazol-3-ylamino}-benzoic acid (28.7 mMol 83.5% yield) as a yellow solid. $^1$H NMR (500 MHz, DMSO-d$_6$) ∂ 10.215 (1H, s), 9.48 (1H, s), 8.18 (1H, d), 7.91 (2 h, d), 7.71 (2H, d), 7.49 (1H, s), 7.35 (1H, d), 4.38 (2H, m), 3.31 (4H, m), 2.10 (3H, s), 1.22 (6H, m) ppm. LC/MS: 2.02 min/436.30 (M+1)

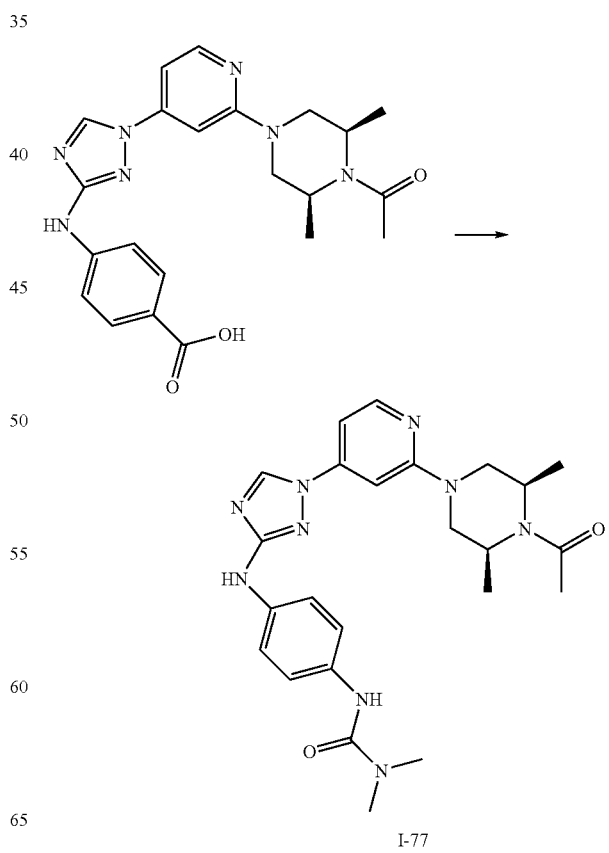

I-77

3-(4-{1-[2-(4-Acetyl-3,5-dimethyl-piperazin-1-yl)-pyridin-4-yl]-1H-[1,2,4]triazol-3-ylamino}-phenyl)-1,1-dimethyl-urea. To a solution of 50 mg of 4-{1-[2-(4-Acetyl-3,5-dimethyl-piperazin-1-yl)-pyridin-4-yl]-1H-[1,2,4]triazol-3-ylamino}-benzoic acid (0.11 mMol, 1.0 equiv) in 10 mL of CH2Cl2 and 5 mL of DMF was added 500 µL of Hunig's base followed by 50 mg of DPPA (0.18 mMol, 1.6 equiv). The reaction was stirred for 30 min at 25° C. and then diluted with 10 mL of MeOH and warmed to 80° C. for 12 hr. The reaction was concentrated and purified by flash chromatography (10:1 CH2Cl2:MeOH) to yield 7 mg of 3-(4-{1-[2-(4-Acetyl-3,5-dimethyl-piperazin-1-yl)-pyridin-4-yl]-1H-[1,2,4]triazol-3-ylamino}-phenyl)-1,1-dimethyl-urea (0.015 mMol, 13% yield). $^1$H NMR (500 MHz, CDCl$_3$) ∂ 8.31 (1H, s), 8.13 (1H, d), 7.40 (2H, d), 7.30 (2H, d), 6.95 (1H, s), 6.82 (1H, d), 6.70 (1H, s), 6.18 (1H, s), 4.15 (2H, m), 3.10 (2H, m), 2.99 (6H, s), 2.90 (2H, m), 2.10 (3H, s), 1.35 (6H, d) ppm. LC/MS: 1.92 min/478.1 (M+1)

Example 5

Compound I-81

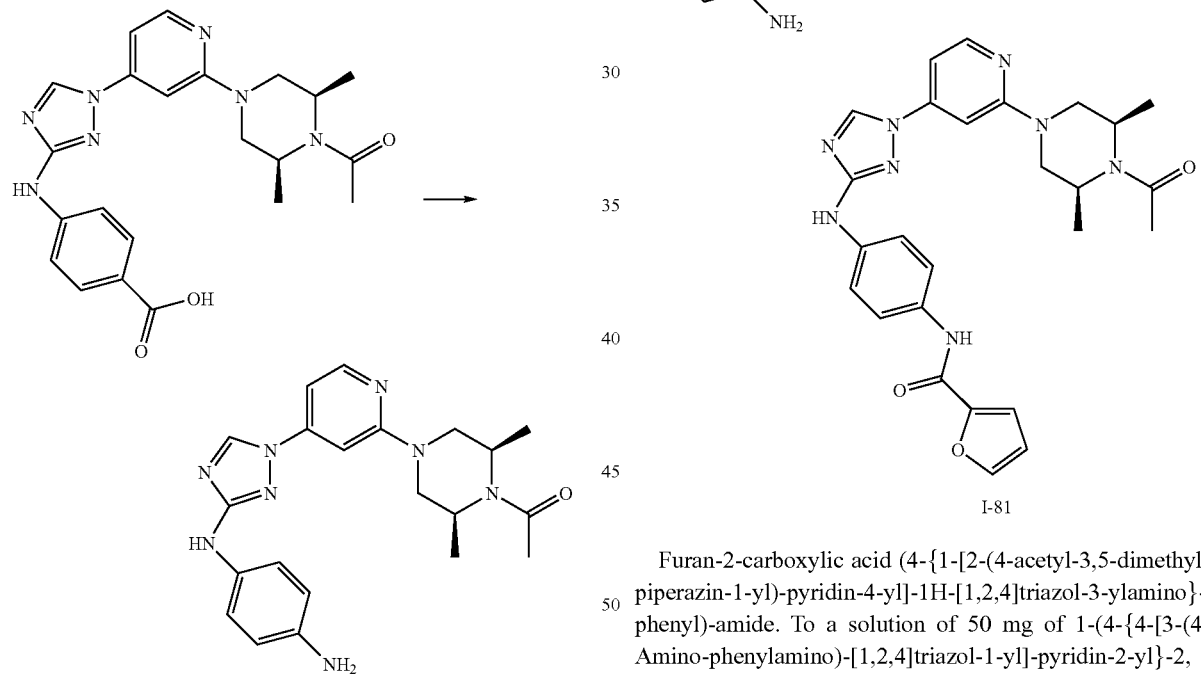

1-(4-{4-[3-(4-Amino-phenylamino)-[1,2,4]triazol-1-yl]-pyridin-2-yl}-2,6-dimethyl-piperazin-1-yl)-ethanone. To a solution of 8 g of 4-{1-[2-(4-Acetyl-3,5-dimethyl-piperazin-1-yl)-pyridin-4-yl]-1H-[1,2,4]triazol-3-ylamino}-benzoic acid (18.3 mMol, 1.00 equiv) in 150 mL of NMP was added 9 mL of Hunig's base followed by 6 g of DPPA (21.8 mMol, 1.19 equiv). The reaction was stirred for 30 min at 25° C. To the reaction mixture was then added 200 mL of TFA and the resulting solution was warmed to 90° C. for 12 hr. After cooling to 25° C., the reaction was quenched with 200 mL of concentrated ammonium hydroxide and concentrated. The resulting oil was triturated with CH$_2$Cl$_2$ and the solid was isolated by filtration. The solid was then dissolved in MeOH (100 mL) and concentrated to 50 mL. The resulting precipitate was isolated and treated with 50 mL of 1 N HCl and concentrated via rotary evaporation. The oil was triturated with ethanol and the resulting solid was removed by filtration. The ethanol solution was concentrated to give 2.5 g of 1-(4-{4-[3-(4-Amino-phenylamino)-[1,2,4]triazol-1-yl]-pyridin-2-yl}-2,6-dimethyl-piperazin-1-yl)-ethanone (6.15 mMol, 33.6% yield) as the HCl salt. $^1$H NMR (500 MHz, CDCl$_3$) ∂ 8.39 (1H, s), 8.10 (1H, d), 7.22 (2H, d), 7.15 (2H, d), 6.95 (1H, s), 6.92 (2H, m), 6.75 (1H, m), 6.65 (2H, d), 4.15 (2H, m), 3.08 (2H, m), 2.99 (2H, m), 2.10 (3H, s), 1.30 (6H, m) ppm. LC/MS: 0.54 min/407.3 (M+1)

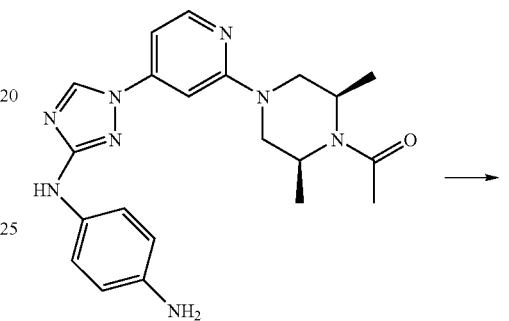

Furan-2-carboxylic acid (4-{1-[2-(4-acetyl-3,5-dimethyl-piperazin-1-yl)-pyridin-4-yl]-1H-[1,2,4]triazol-3-ylamino}-phenyl)-amide. To a solution of 50 mg of 1-(4-{4-[3-(4-Amino-phenylamino)-[1,2,4]triazol-1-yl]-pyridin-2-yl}-2,6-dimethyl-piperazin-1-yl)-ethanone (0.123 mMol. 1.00 equiv) in 2 mL of NMP was added 5 mL of CH$_2$Cl$_2$ and 500 µL of Hunig's base followed by 100 µL of 2-furanyl chloride (1.01 mMol, 8.13 equiv). The reaction mixture was stirred for 1 hr and concentrated. The resulting oil was purified via flash chromatography (EtOAc) to yield 1.4 mg of Furan-2-carboxylic acid (4-{1-[2-(4-acetyl-3,5-dimethyl-piperazin-1-yl)-pyridin-4-yl]-1H-[1,2,4]triazol-3-ylamino}-phenyl)-amide (0.0028 mMol, 2.3% yield). $^1$H NMR (500 MHz, MeOD-d$_4$) ∂ 8.95 (1H, s), 8.18 (1H, d), 7.72 (1H, m), 7.61 (4H, m), 7.25 (2H, m), 7.15 (1H, m), 6.61 (1H, s), 4.30 (2H, m), 3.30 (2H, m), 3.15 (2H, m), 2.20 (3H, s), 1.35 (6H, m) ppm. LC/MS: 2.2 min/501.3 (M+1).

Example 6

Compound I-85

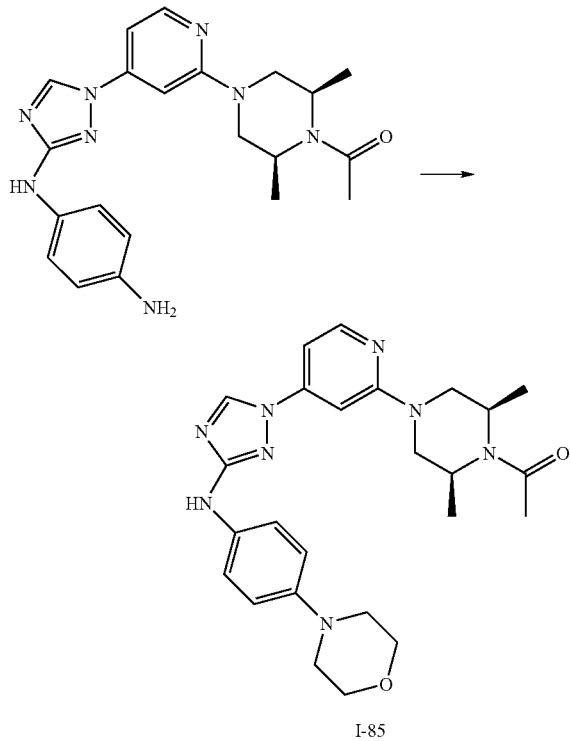

I-85

1-(2,6-Dimethyl-4-{4-[3-(4-morpholin-4-yl-phenylamino)-[1,2,4]triazol-1-yl]-pyridin-2-yl}-piperazin-1-yl)-ethanone. To a solution of 100 mg of 1-(4-{4-[3-(4-Amino-phenylamino)-[1,2,4]triazol-1-yl]-pyridin-2-yl}-2,6-dimethyl-piperazin-1-yl)-ethanone (0.246 mMol, 1.00 equiv) in 2 mL of DMF was added 100 µL of 2-chloroethyl ether, 50 mg of sodium iodide and 100 mg of K2CO3. After 3 hr at 110° C. the reaction was concentrated and purified by flash chromatography (EtOAc) to yield 70 mg of 1-(2,6-Dimethyl-4-{4-[3-(4-morpholin-4-yl-phenylamino)-[1,2,4]triazol-1-yl]-pyridin-2-yl}-piperazin-1-yl)-ethanone (0.147 mMol, 59.8% yield). $^1$H NMR (500 MHz, DMSO-$d_6$) ∂ 9.26 (1H, s), 9.21 (1H, s), 8.20 (1H, d), 7.52 (2H, d), 7.21 (1H, s), 7.12 (1H, d), 6.90 (2H, d), 4.30 (2H, m), 4.05 (2H, m), 3.73 (4H, m), 3.09 (2H, m), 2.99 (4H, m), 2.51 (3H, s), 1.2 (6H, m) ppm. LC/MS: 1.78 min/477.3 (M+1).

Example 7

Compound I-97

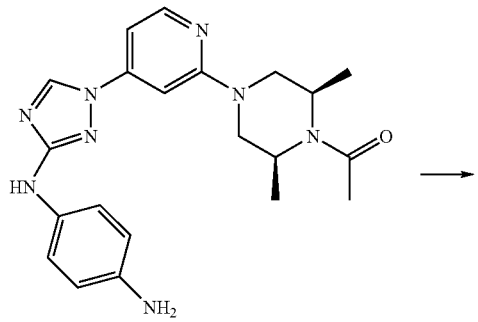

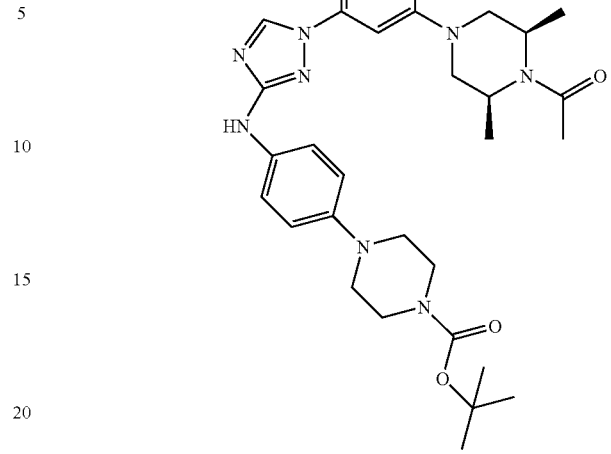

4-(4-{1-[2-(4-Acetyl-3,5-dimethyl-piperazin-1-yl)-pyridin-4-yl]-1H-[1,2,4]triazol-3-ylamino}-phenyl)-piperazine-1-carboxylic acid tert-butyl ester. To a solution of 20 mg of 1-(4-{4-[3-(4-Amino-phenylamino)-[1,2,4]triazol-1-yl]-pyridin-2-yl}-2,6-dimethyl-piperazin-1-yl)-ethanone (0.049 mMol, 1.0 equiv) in 5 mL of iPrOH, was added 15 mg of sodium iodide and 20 mg of the hydrochloride salt of bis(2-chloroethyl)amine (0.17 mMol, 3.5 equiv). The resulting suspension was heated to 150° C. via microwave irradiation for 20 min. The iPrOH was removed via rotary evaporation and the residue was redissolved in 5 mL of THF. To the stirred suspension was added 500 µL of Hunig's base and 200 mg of tert butyl pyrocarbonate. After stirring for 3 hr at 25° C., the reaction was concentrated and purified by silica gel chromatography to yield 2.5 mg of 4-(4-{1-[2-(4-Acetyl-3,5-dimethyl-piperazin-1-yl)-pyridin-4-yl]-1H-[1,2,4]triazol-3-ylamino}-phenyl)-piperazine-1-carboxylic acid tert-butyl ester (0.0052 mMol, 10.1% yield). $^1$H NMR (500 MHz, MeOD-$d_4$) ∂ 8.95 (1H, s), 8.15 (1H, d), 7.50 (2H, d), 7.20 (1H, s), 7.10 (1H, d), 6.95 (2H, m), 4.31 (3H, m), 3.55 (4H, m), 3.15 (2H, m), 3.05 (3H, m), 2.18 (3H, s), 1.45 (9H, s), 1.35 (6H, m) ppm. LC/MS: 2.58 min/576.4 (M+1).

Examples 8 & 9

General Syntheses of Aminotriazole Pyridines (Refer Also to Scheme 7)

Example 8

Compound I-98

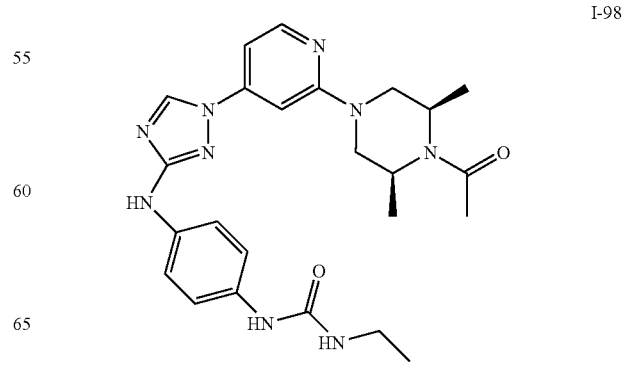

I-98

147

1) 1-(4-{1-[2-(4-Acetyl-3,5-dimethyl-piperazin-1-yl)-pyridin-4-yl]-1H-[1,2,4]triazol-3-ylamino}-phenyl)-3-ethyl-urea. To a solution of 1-(4-{4-[3-(4-Amino-phenylamino)-[1,2,4]triazol-1-yl]-pyridin-2-yl}-2,6-dimethyl-piperazin-1-yl)-ethanone (30 mg, 0.074 mmol) in DMF was added 2 drops of DIEA and Ethyl isocyanate (6.0 mg, 0.085 mmol). The reaction was stirred at 60° C. for 30 mins and the material was purified by P-HPLC.

I-99, I-100, and I-101 were prepared in a similar way.

Example 9

I-87

148

2) (4-{1-[2-(4-Acetyl-3,5-dimethyl-piperazin-1-yl)-pyridin-4-yl]-1H-[1,2,4]triazol-3-ylamino}-phenyl)-carbamic acid methyl ester. To a solution of 1-(4-{4-[3-(4-Amino-phenylamino)-[1,2,4]triazol-1-yl]-pyridin-2-yl}-2,6-dimethyl-piperazin-1-yl)-ethanone (30 mg, 0.74 mmol) in DMF was added 2 drops of DIEA and ethyl chloroformate (8.9 mg, 0.09 mmol). The reaction was stirred at room temperature for 60 mins and the material was purified by P-HPLC.

I-88, I-89, I-90, and I-91 were prepared in a similar way.

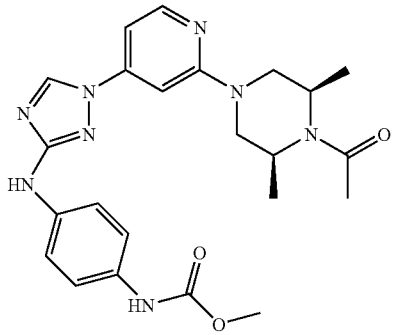

I-87

Scheme 14 depicts a route to Compound I-104.

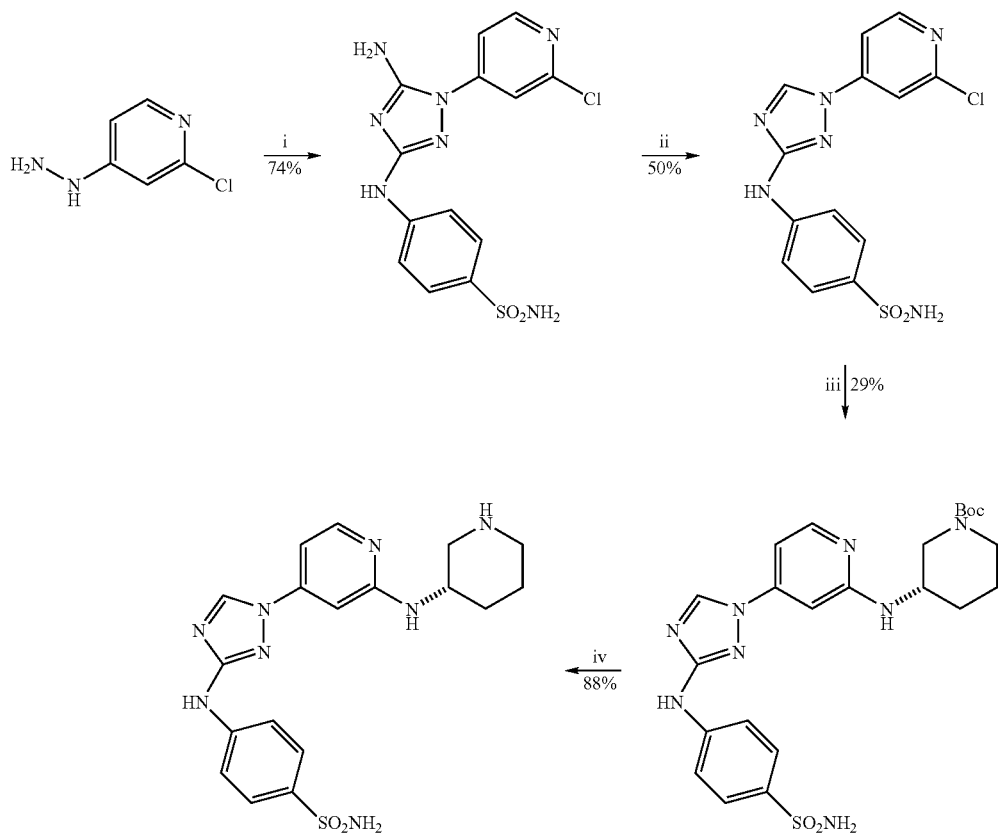

i. PhON(CN)NHPh-4-SO$_2$NH$_2$, DIPEA, NMP microwave; ii. (CH$_3$)$_2$CHCH$_2$CH$_2$ONO, THF, i-PrOH, rt; iii. (S)-3-amino-piperidine-1-carboxylic acid tert-butyl ester, DMAP, NMP, microwave iv. TFA, CH$_2$Cl$_2$

Example 10

Compound I-104

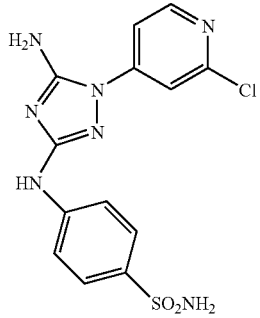

4-[5-Amino-1-(2-chloro-pyridin-4-yl)-1H-[1,2,4]triazol-3-ylamino]-benzenesulfonamide. A microwave reaction vessel was charged with 500 mg of (2-chloro-pyridin-4-yl)-hydrazine (3.48 mmol, 1.3 equiv) and 848 mg g of N-cyano-N'-(2-phenyl-isoureido)-benzenesulfonamide (2.68 mmol, 1 equiv) in a mixture of NMP (5 mL) and diisopropylethylamine (1.4 mL). The sealed vessel was warmed to 220° C. for 6 min via microwave irradiation. Upon cooling, the resulting solution was poured onto saturated aqueous sodium hydrogen carbonate (40 mL) and a yellow solid precipitated. The precipitate was collected by vacuum filtration and washed with water (3×10 mL). After azeotropic drying (3×50 mL of acetonitrile) the dark yellow solid was used without further purification (723.1 mg, 74%); $^1$H NMR (400 MHz, (CD$_3$)$_2$SO) δ 9.67 (1H, s), 8.45 (1H, d, J=6.3). 7.69 (6H, m), 7.12 (4H, br s); MS (ES$^+$) m/e 366.38, (ES$^-$) m/e 364.49

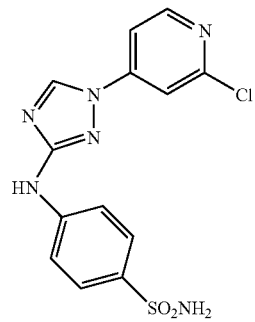

4-[1-(2-Chloro-pyridin-4-yl)-1H-[1,2,4]triazol-3-ylamino]-benzenesulfonamide. To a solution of 250 mg of 4-[5-amino-1-(2-chloro-pyridin-4-yl)-1H-[1,2,4]triazol-3-ylamino]-benzenesulfonamide (0.686 mmol, 1 equiv) in 40 mL of 1:1 THF:iPrOH, 160 mg of isoamyl nitrite (1.37 mmol, 2 equiv) was added. The dark yellow solution was stirred for 12 h at 25° C. and then heated under reflux for 6 h. The reaction mixture was cooled and concentrated in vacuo. The resulting yellow solid was triturated with methanol and filtered to give the title compound as a yellow solid (118.9 mg, 50%); $^1$H NMR (400 MHz, (CD$_3$)$_2$SO) δ 10.20 (1H, s), 9.42 (1H, s), 8.55 (1H, d, J=5.6), 8.07 (1H, m), 7.95 (1H, dd, J=5.6 and 1.8), 7.77 (4H, m) and 7.18 (2H, s); MS (ES$^+$) m/e 351.36, (ES$-$) m/e 349.48

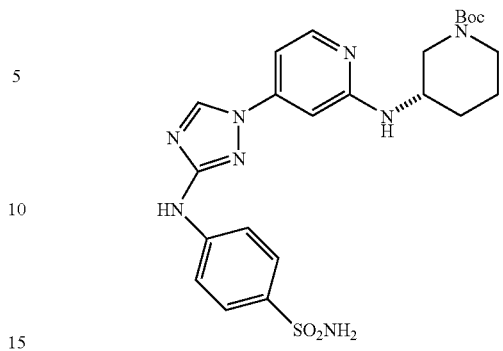

3-(S)-{4-[3-(4-Sulfamoyl-phenylamino)-[1,2,4]triazol-1-yl]-pyridin-2-ylamino}-piperidine-1-carboxylic acid tert-butyl ester. A microwave reaction vessel was charged with 50 mg of 4-[1-(2-Chloro-pyridin-4-yl)-1H-[1,2,4]triazol-3-ylamino]-benzenesulfonamide (0.14 mmol, 1 equiv), 110 mg (S)-3-amino-piperidine-1-carboxylic acid tert-butyl ester (0.57 mmol, 4 equiv) and 17.0 mg DMAP (0.014 mmol, 0.1 equiv) in NMP (1.5 mL). The resulting solution was warmed to 130° C. via microwave irradiation for 20 min and then heated at 180° C. for an additional 70 min via microwave irradiation. The reaction mixture was cooled and concentrated in vacuo and the residue purified by preparative HPLC. To a solution of 12.0 mg of this product, 3-(S)-{4-[3-(4-sulfamoyl-phenylamino)-[1,2,4]triazol-1-yl]-pyridin-2-ylamino}-piperidine (0.029 mmol, 1 equiv) in dichloromethane (5 mL), di-tert-butyl dicarbonate (9.5 mg, 0.043 mmol, 1.5 equiv) and 6 µL triethylamine (0.058 mmol, 2 equiv) were added and the resulting solution stirred at rt for 1 h. The reaction mixture was concentrated in vacuo and the residue purified by column chromatography on silica gel eluting with 50% EtOAc: petroleum ether moving to EtOAc (4.2 mg, 29%); MS (ES$^+$) m/e 515.55, (ES–) m/e 513.70

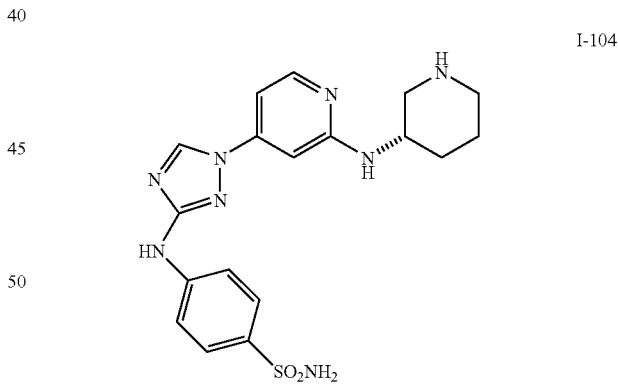

I-104

3-(S)-{4-[3-(4-Sulfamoyl-phenylamino)-[1,2,4]triazol-1-yl]-pyridin-2-ylamino}-piperidine, ditrifluoroacetic acid salt. To a solution of 4.6 mg 3-(S)-{4-[3-(4-sulfamoyl-phenylamino)-[1,2,4]triazol-1-yl]-pyridin-2-ylamino}-piperidine-1-carboxylic acid tert-butyl ester (0.008 mmol, 1 equiv) in dichloromethane (2 mL), TFA (0.5 mL) was added and the resulting solution stirred at rt for 1 h, The reaction mixture was concentrated in vacuo and the residue freeze dried from a mixture of acetonitrile (2 mL) and water (2 mL) to give the title compound as a white solid (4.2 mg, 88%); $^1$H NMR (400 MHz, (CD$_3$)$_2$SO) δ 1.60 (2H, m), 1.85 (1H, m), 1.99 (1H, m), 3.18 (3H, m), 3.93 (1H, m), 4.43 (1H, m), 7.16 (2H, br s), 7.19

(1H, d, J=5.5), 7.26 (1H, s), 7.74 (4H, s), 7.97 (3H, m), 8.24 (1H, d, J=5.5), 9.34 (1H, s), 10.10 (1H, s); MS (ES+) m/e 415.51, (ES−) m/e 413.66.

Example 11

Compound I-49; Scheme 9—NMP Method

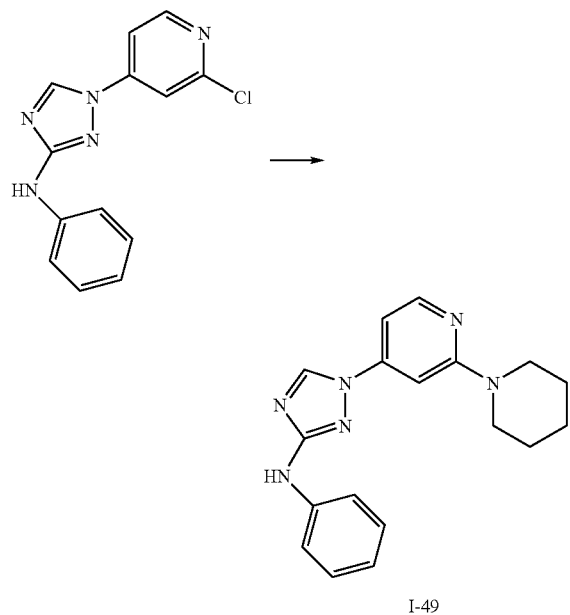

I-49

To a microwave reaction vial equipped with a stirrer bar was added 1-(2-chloro-pyridin-4-yl)-N3-phenyl-1H-[1,2,4]triazole-5-amine (50 mg, 0.17 mmol, 1 equiv), piperidine (37 μl, 0.35 mmol, 2.0 equiv), and NMP (1 ml). The reaction mixture was heated to 250° C./300 W for 45 minutes via microwave irradiation. The resulting yellow solution was concentrated in vacuo yielding a brown oil. Water was added and the resulting gum was sonicated for 15 minutes whereupon a fawn solid precipitated which was collected by filtration. This solid was washed with water until the filtrate was clear and dried in vacuo (40° C.) for 8 hours to yield phenyl-[1-(3,4,5,6-tetrahydro-2H-[1,2']bipyridinyl-4'-yl)-1H-[1,2,4]triazol-3-yl]-amine (38 mg, 69% yield).

Example 12

Compound I-125; Scheme 9—nBuOH Method

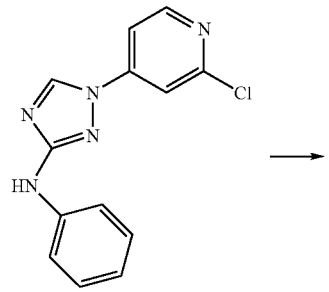

-continued

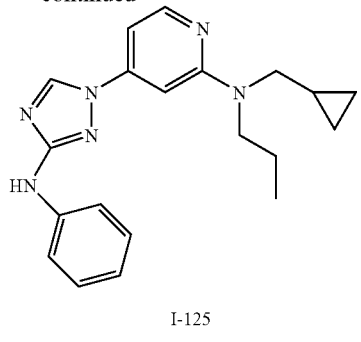

I-125

To a microwave reaction vial equipped with a stirrer bar was added 1-(2-chloro-pyridin-4-yl)-N3-phenyl-1H-[1,2,4]triazole-5-amine (50 mg, 0.17 mmol, 1 equiv), N-propylcyclopropanemethylamine (39 mg, 0.35 mmol, 2.0 equiv), nBuOH (1 ml) and 1 drop of an ionic liquid (BMIM-OTf). The reaction mixture was heated to 230° C./300 W for 20 minutes followed by 20 minutes cooling followed by 20 minutes at 230° C. via microwave irradiation. The resulting yellow solution was concentrated in vacuo yielding a yellow oil which was diluted with EtOAc (5 ml) and washed with water (2 ml) and then concentrated in vacuo. The crude product was purified by flash chromatography on silica gel eluting with EtOAc to yield cyclopropylmethyl-[4-(3-phenylamino-[1,2,4]triazol-1-yl)-pyridin-2-yl]-propyl-amine as a yellow solid (21 mg, 36% yield).

Example 13

Compound I-62; Scheme 9—nBuOH Thermal Method

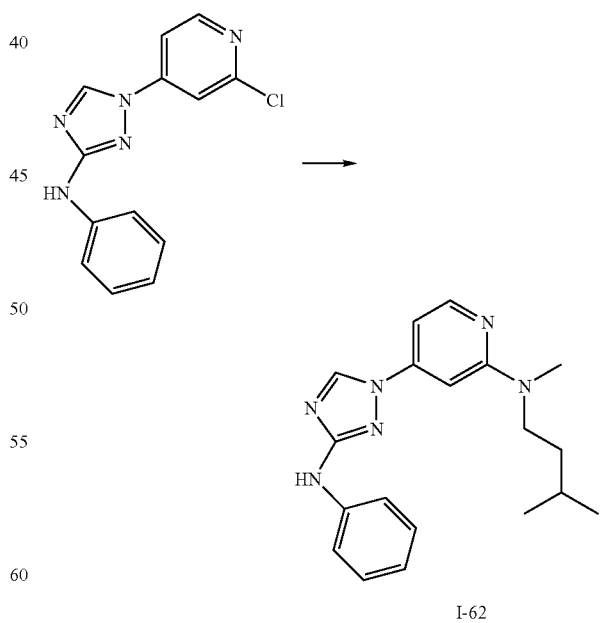

I-62

To a small, screw cap vial was added 1-(2-chloro-pyridin-4-yl)-N3-phenyl-1H-[1,2,4]triazole-5-amine (50 mg, 0.17 mmol, 1 equiv), methyl isoamylamine (70 mg, 0.67 mmol, 4.0 equiv) and nBuOH (2 ml). The reaction mixture was

153 heated to 120° C. for 48 hours and then allowed to cool to ambient temperature. Water was added to the reaction (10 ml) and a fawn solid precipitated which was collected by filtration. The solid was washed with water until the filtrate was clear and the resulting solid dried in vacuo to yield methyl-(3-methyl-butyl)-[4-(3-phenylamino-[1,2,4]triazol-1-yl)-pyridin-2-yl]-amine (27 mg, 50% yield).

Example 14

Compound I-59; Scheme 9—Neat Thermal Method

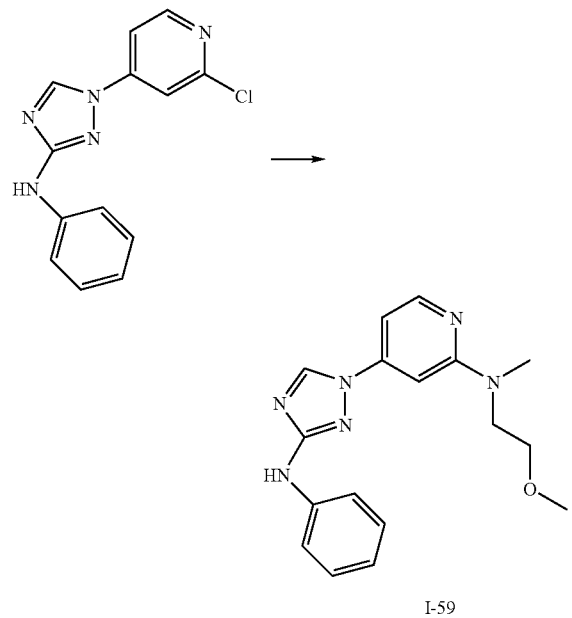

I-59

To a small, screw cap vial was added 1-(2-chloro-pyridin-4-yl)-N3-phenyl-1H-[1,2,4]triazole-5-amine (50 mg, 0.17 mmol, 1 equiv), N-(methoxyethyl)methylamine (0.7 ml, excess). The reaction was heated to 120° C. for 48 hours and allowed to cool to ambient temperature. Water was added to the reaction (10 ml) and a fawn solid precipitated which was collected by filtration. The solid was washed with water until the filtrate was clear and the resulting solid dried in vacuo to yield (2-methoxy-ethyl)-methyl-[4-(3-phenylamino-[1,2,4]triazol-1-yl)-pyridin-2-yl]-amine (32 mg, 58% yield).

Example 14

Compound I-126; Scheme 9—Buchwald Method

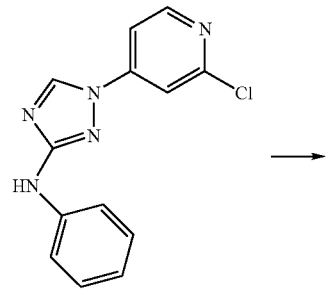

-continued

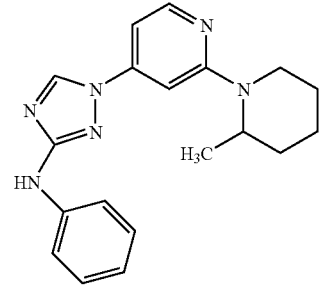

I-126

To a microwave reaction vial equipped with a stirrer bar was added 1-(2-chloro-pyridin-4-yl)-N3-phenyl-1H-[1,2,4]triazole-5-amine (50 mg, 0.17 mmol, 1 equiv), methyl piperidine (20 mg, 0.20 mmol, 1.1 equiv), NaO$^t$Bu (26 mg, 0.28 mmol, 1.5 equiv) 1,3-bis-(2,6-diisopropyl phenyl)imidazolium hydrochloride (1.6 mg, 0.0037 mmol, 2 mol %) and 1,4 dioxane (1 ml, degassed). Pd$_2$(dba)$_3$ (1.7 mg, 0.017 mmol, 1 mol %) was added under an N$_2$ environment and the vessel was heated to 160° C. for 45 minutes via microwave irradiation. The resulting yellow solution was concentrated in vacuo yielding a yellow oil which was diluted with EtOAc (5 ml) and washed with water (2 ml) and then concentrated in vacuo. The crude product was purified by column chromatography on silica gel eluting with EtOAc to yield [1-(2-methyl-3,4,5,6-tetrahydro-2H-[1,2']bipyridinyl-4'-yl)-1H-[1,2,4]triazol-3-yl]-phenyl-amine as a yellow solid (23 mg, 41% yield).

BIOLOGICAL DATA AND EXAMPLES

Example 1

Inhibition of FLT-3

Compounds were screened for their ability to inhibit FLT-3 activity using a radiometric filter-binding assay. This assay monitors the $^{33}$P incorporation into a substrate poly(Glu, Tyr) 4:1 (pE4Y). Reactions were carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 90 μM ATP and 0.5 mg/mL pE4Y (both from Sigma Chemicals, St Louis, Mo.). The final concentration of compounds is generally between 0.01 and 5 μM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM MgCl$_2$, 25 mM NaCl, 1 mg/ml pE4Y and 180 μM ATP (containing 0.3 μCi of [γ-$^{33}$P] ATP for each reaction). Solution 2 contains 100 mM HEPES (pH 7.5), 10 mM MgCl$_2$, 25 mM NaCl, 2 mM DTT, 0.02% BSA and 3 nM FLT-3. The assay was run on a 96 well plate by mixing 50 μL each of Solution1 and 2.5 mL of the test compounds. The reaction was initiated with Solution2. After incubation for 20 minutes at room temperature, the reaction was stopped with 50 μL of 20% TCA containing 0.4 mM of ATP. All of the reaction volume was then transferred to a filter plate and washed with 5% TCA by a Harvester9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an IC$_{50}$ or K$_i$.

In general, compounds of the invention, including compounds in Table 1, are effective for the inhibition of FLT-3. The following compounds were shown to have $IC_{50}$ or $K_i$ values less than 0.1 μM: I-42, I-43, I-44, I-45, I-46, and I-47. Compounds I-42, I-43, I-44, I-45, I-46, I-50, I-55, I-56, I-57, I-58, I-59, I-62, I-87, I-94, I-95, I-96, I-97, I-98, I-99, I-100, I-102, and I-105 were shown to have $K_i$ values of 1-30 nM. Compounds I-47, I-60, I-67, I-68, I-69, I-71, I-75, I-76, I-83, I-84, I-85, I-86, I-88, I-89, I-90, I-91, I-92, I-101, I-106, and I-107, I-134, and I-135 were shown to have $K_i$ values of 30-200 nM. Compounds I-63, I-64, and I-134 were shown to have a $K_i$ value of >200 nM. Compounds I-49, I-51, I-66, I-72, I-73, I-74, I-77, I-78, I-79, I-80, I-81, and I-82 were shown to have a $K_i$ value of <60 nM Example 2

Inhibition of c-KIT

Compounds are screened for their ability to inhibit c-KIT activity using a radiometric filter-binding assay. This assay monitors the $^{33}P$ incorporation into a substrate poly(Glu, Tyr) 4:1 (pE4Y). Reactions are carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 700 μM ATP and 0.5 mg/mL pE4Y (both from Sigma Chemicals, St Louis, Mo.). The final concentration of compounds is generally between 0.01 and 5 μM. Typically, a 12-point titration is conducted by preparing serial dilutions from 10 mM DMSO stock of test compound. Reactions were carried out at room temperature.

Two assay solutions are prepared. Solution 1 contains 100 mM HEPES (pH 7.5), 10 mM $MgCl_2$, 25 mM NaCl, 1 mg/ml pE4Y and 1.4 mM ATP (containing 0.5 μCi of $[\gamma\text{-}^{33}P]ATP$ for each reaction). Solution 2 contains 100 mM HEPES (pH 7.5), 10 mM $MgCl_2$, 25 mM NaCl, 2 mM DTT, 0.02% BSA and 25 nM c-KIT. The assay is run on a 96 well plate by mixing 33 μL of Solution1 and 1.65 μL of the test compounds. The reaction is initiated with 33 μL of Solution2. After incubation for 20 minutes at room temperature, the reaction was stopped with 50 μL of 10% TCA containing 0.2 mM of ATP. All of the reaction volume is then transferred to a filter plate and washed with 5% TCA by a Harvester9600 from TOMTEC (Hamden, Conn.). The amount of $^{33}P$ incorporation into pE4y is analyzed by a Packard TopCount Microplate Scintillation Counter (Meriden, Conn.). The data is fitted using Prism software to get an $IC_{50}$ or $K_i$.

Compounds of the present invention were found to inhibit c-KIT. Compounds I-44, I-45, I-46, I-47, I-55, I-56, I-58, I-75, I-80, and I-105 were shown to have $K_i$ values of <0.05 μM. Compounds I-66, I-72, I-73, I-74, I-77, I-78, I-79, I-81, I-82, I-85, I-87, I-88, I-89, I-90, I-91, I-92, I-97, I-98, I-99, I-100, and I-101 were shown to have K; values of 0.05-0.5 μM. Compound I-86 was shown to have a K; value of >0.5 μM.

Example 3

Inhibition of GSK-3

Compounds are screened for their ability to inhibit GSK-3β (AA 1-420) activity using a standard coupled enzyme system [Fox et al. *Protein Sci.* 1998, 7, 2249]. Reactions are carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay are 20 μM ATP (Sigma Chemicals, St Louis, Mo.) and 300 μM peptide (American Peptide, Sunnyvale, Calif.). Reactions are carried out at 30° C. and 20 nM GSK-3β. Final concentrations of the components of the coupled enzyme system are 2.5 mM phosphoenolpyruvate, 300 μM NADH, 30 μg/ml pyruvate kinase and 10 μg/ml lactate dehydrogenase.

An assay stock buffer solution is prepared containing all of the reagents listed above with the exception of ATP and the test compound of interest. The assay stock buffer solution (175 μl) is incubated in a 96 well plate with 5 μl of the test compound of interest at final concentrations spanning 0.002 μM to 30 μM at 30° C. for 10 min. Typically, a 12 point titration is conducted by preparing serial dilutions (from 10 mM compound stocks) with DMSO of the test compounds in daughter plates. The reaction is initiated by the addition of 20 μl of ATP (final concentration 20 μM). Rates of reaction are obtained using a Molecular Devices Spectramax plate reader (Sunnyvale, Calif.) over 10 min at 30° C. The $K_i$ values are determined from the rate data as a function of inhibitor concentration.

Compounds of the present invention were found to inhibit GSK-3. Compounds I-51, I-54, I-56, I-57, I-58, I-59, I-62, I-93, I-94, I-95, and I-96 were shown to have K; values of <0.5 μM. Compounds I-43, I-49, I-50, I-52, I-65, and I-73 were shown to have $K_i$ values of 0.5-1 μM. Compounds I-42, I-44, I-45, I-46, I-47, I-53, I-55, I-60, I-61, I-63, I-64, I-66, I-67, I-68, I-69, I-70, I-71, I-72, I-74, I-75, I-76, I-77, I-78, I-79, I-80, I-81, I-82, I-83, I-84, I-85, I-86, I-87, I-88, I-89, I-90, I-91, I-92, I-97, I-98, I-99, I-100, I-101, I-102, I-105, I-106, I-107, I-134, and I-135, were shown to have $K_i$ values of >1 μM.

Example 4

Inhibition of CDK-2

Compounds are screened for their ability to inhibit CDK-2/Cyclin A using a standard coupled enzyme assay [Fox et al. *Protein Sci.* 1998, 7, 2249]. Reactions were carried out in 100 mM HEPES (pH 7.5), 10 mM $MgCl_2$, 25 mM NaCl, 1 mM DTT and 1.5% DMSO. Final substrate concentrations in the assay are 100 μM ATP (Sigma chemicals) and 100 μM peptide (American Peptide, Sunnyvale, Calif.). Assays are carried out at 30° C. and 25 nM CDK-2/CyclinA. Final concentrations of the components of the coupled enzyme system are 2.5 mM phosphoenolpyruvate, 350 μM NADH, 30 μg/ml pyruvate kinase and 10 μg/ml lactate dehydrogenase.

An assay stock buffer solution is prepared containing all of the reagents listed above, with the exception of CDK-2/CyclinA, DTT and the test compound of interest. 56 μl of the test reaction is placed in a 384 well plate followed by addition of 1 μl of 2 mM DMSO stock containing the test compound (final compound concentration 30 μM). The plate is preincubated for ~10 minutes at 30° C. and the reaction initiated by addition of 10 μl of enzyme (final concentration 25 nM). Rates of reaction are obtained using a BioRad Ultramark plate reader (Hercules, Calif.) over a 5 minute read time at 30° C. $K_i$ values are determined according to standard methods.

Compounds of the present invention were found to inhibit CDK-2. Compounds I-49, I-50, I-51, I-52, I-54, I-55, I-56, I-57, I-58, I-59, I-62, I-65, I-72, I-73, I-74, I-78, I-79, I-80, I-82, I-85, I-87, I-88, I-96, I-97, I-98, I-99, and I-100 were shown to have $K_i$ values of <0.5 μM. Compounds I-43, I-61, I-66, I-75, I-81, I-89, I-90, I-91, I-92, I-93, I-95, I-101, and I-105 were shown to have $K_i$ values of 0.5-1 μM. Compounds I-42, I-44, I-45, I-46, I-47, I-53, I-60, I-63, I-64, I-67, I-68, I-69, I-70, I-71, I-76, I-77, I-83, I-84, I-86, I-94, I-102, I-106, I-107, I-134, and I-135 were shown to have $K_i$ values of >1 µM

Example 5

Inhibition of SRC

The compounds are evaluated as inhibitors of human Src kinase using either a radioactivity-based assay or spectrophotometric assay.

Src Inhibition Assay A: Radioactivity-Based Assay

The compounds are assayed as inhibitors of full-length recombinant human Src kinase (from Upstate Biotechnology, cat. no. 14-117) expressed and purified from baculo viral cells. Src kinase activity is monitored by following the incorporation of $^{33}$P from ATP into the tyrosine of a random poly Glu-Tyr polymer substrate of composition, Glu:Tyr=4:1 (Sigma, cat. no. P-0275). The following are the final concentrations of the assay components: 0.05 M HEPES (pH 7.6), 10 mM $MgCl_2$, 2 mM DTT, 0.25 mg/ml BSA, 10 µM ATP (1-2 µCi $^{33}$P-ATP per reaction), 5 mg/ml poly Glu-Tyr, and 1-2 units of recombinant human Src kinase. In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with $^{33}$P-ATP. After 20 min of reaction, the reactions are quenched with 150 µl of 10% trichloroacetic acid (TCA) containing 20 mM $Na_3PO_4$. The quenched samples are then transferred to a 96-well filter plate (Whatman, UNI-Filter GF/F Glass Fiber Filter, cat no. 7700-3310) installed on a filter plate vacuum manifold. Filter plates are washed four times with 10% TCA containing 20 mM $Na_3PO_4$ and then 4 times with methanol. 200 µl of scintillation fluid is then added to each well. The plates are sealed and the amount of radioactivity associated with the filters is quantified on a TopCount scintillation counter. The radioactivity incorporated is plotted as a function of the inhibitor concentration. The data is fitted to a competitive inhibition kinetics model to get the $K_i$ for the compound.

Src Inhibition Assay B: Spectrophotometric Assay

The ADP produced from ATP by the human recombinant Src kinase-catalyzed phosphorylation of poly Glu-Tyr substrate is quantified using a coupled enzyme assay [Fox et al. *Protein Sci.* 1998, 7, 2249]. In this assay one molecule of NADH is oxidised to NAD for every molecule of ADP produced in the kinase reaction. The disappearance of NADH is conveniently followed at 340 nm.

The following are the final concentrations of the assay components: 0.025 M HEPES (pH 7.6), 10 mM $MgCl_2$, 2 mM DTT, 0.25 mg/ml poly Glu-Tyr, and 25 nM of recombinant human Src kinase. Final concentrations of the components of the coupled enzyme system are 2.5 mM phosphoenolpyruvate, 200 µM NADH, 30 µg/ml pyruvate kinase and 10 µg/ml lactate dehydrogenase.

In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with 100 µM ATP. The absorbance change at 340 nm with time, the rate of the reaction, is monitored on a molecular devices plate reader. The data of rate as a function of the inhibitor concentration is fitted to competitive inhibition kinetics model to get the $K_i$ for the compound.

Compounds of the present invention were found to inhibit SRC. Compounds I-42, I-43, I-45, I-49, I-50, I-52, I-54, I-58, I-61, I-65, I-73, I-74, I-75, I-78, I-79, I-81, I-82, I-87, I-88, I-94, I-95, I-96, I-97, I-98, I-99, I-100, I-102, I-103, and I-105 were shown to have $K_i$ values of <0.5 µM in the uv-vis assay. Compounds I-44, I-55, I-56, I-57, I-62, I-72, I-77, I-80, I-85, I-89, I-90, I-91, I-92, I-93, and I-101 were shown to have $K_i$ values of 0.5-1 µM in the uv-vis assay. Compounds I-46, I-47, I-51, I-53, I-59, I-60, I-63, I-64, I-66, I-67, I-68, I-69, I-70, I-71, I-76, I-83, I-84, I-86, I-106, I-107, I-125, I-126, I-133, I-134, and I-135 were shown to have $K_i$ values of >1 µM in the uv-vis assay.

Example 6

Inhibition of SYK

Compounds are screened for their ability to inhibit SYK using a standard coupled enzyme assay [Fox et al. *Protein Sci.* 1998, 7, 2249]. Reactions are carried out in 100 mM HEPES (pH 7.5), 10 mM $MgCl_2$, 25 mM NaCl, 1 mM DTT and 1.5% DMSO. Final substrate concentrations in the assay were 200 mM ATP (Sigma Chemical Co.) and 4 µM poly Gly-Tyr peptide (Sigma Chemical Co.). Assays are carried out at 30° C. and 200 nM SYK. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution is prepared containing all of the reagents listed above, with the exception of SYK, DTT and the test compound of interest. 56 µl of the test reaction was placed in a 96 well plate followed by the addition of 1 µl of 2 mM DMSO stock containing the test compound (final compound concentration 30 mM). The plate is pre-incubated for ~10 minutes at 30° C. and the reaction initiated by the addition of 10 µl of enzyme (final concentration 25 nM). Rates of reaction are obtained using a BioRad Ultramark plate reader (Hercules, Calif.) over a 5 minute read time at 30° C., and $K_i$ values were determined according to standard methods.

Example 7

Inhibition of FMS

Compounds are screened for their ability to inhibit FMS activity using a radiometric filter-binding assay. This assay monitors the $^{33}$P incorporation into a substrate poly(Glu, Tyr) 4:1 (pE4Y). Reactions are carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay are 90 µM ATP and 0.5 mg/mL pE4Y (both from Sigma Chemicals, St Louis, Mo.). The final concentration of compounds is generally between 0.01 and 5 µM. Typically, a 12-point titration is conducted by preparing serial dilutions from 10 mM DMSO stock of test compound. Reactions were carried out at room temperature.

Two assay solutions are prepared. Solution 1 contains 100 mM HEPES (pH 7.5), 10 mM $MgCl_2$, 25 mM NaCl, 1 mg/ml pE4Y and 180 µM ATP (containing 0.3 µCi of [γ-$^{33}$P]ATP for each reaction). Solution 2 contains 100 mM HEPES (pH 7.5), 10 mM $MgCl_2$, 25 mM NaCl, 2 mM DTT, 0.02% BSA and 3 nM FMS. The assay is run on a 96 well plate by mixing 50 µL each of Solution 1 and 2.5 mL of the test compounds. The reaction is initiated with Solution 2. After incubation for 20 minutes at room temperature, the reaction is stopped with 50 µL of 20% TCA containing 0.4 mM of ATP. All of the reaction volume is then transferred to a filter plate and washed with 5% TCA by a Harvester9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an $IC_{50}$ or $K_i$.

Example 8

JAK3 Inhibition Assay

Compound inhibition of JAK was assayed by the method described by G. R. Brown, et al, *Bioorg. Med. Chem. Lett.* 2000, vol. 10, pp 575-579 in the following manner. Into Maxisorb plates, previously coated at 4° C. with Poly (Glu, Ala, Tyr) 6:3:1 then washed with phosphate buffered saline 0.05% and Tween-(PBST), was added 2 µM ATP, 5 mM $MgCl_2$, and a solution of compound in DMSO. The reaction was started with JAK enzyme and the plates incubated for 60 minutes at 30° C. The plates were then washed with PBST, 100 µL HRP-Conjugated 4G10 antibody was added, and the plate incubated for 90 minutes at 30° C. The plate was again washed with PBST, 100 µL TMB solution is added, and the plates were incubated for another 30 minutes at 30° C. Sulfuric acid (100 µL of 1M) was added to stop the reaction and the plate is read at 450 nm to obtain the optical densities for analysis to determine $K_i$ values.

Compounds of the present invention were found to inhibit JAK-3. Compound I-73, I-74, I-79, I-82, I-87, I-92, I-98, and I-100 were shown to have K; values of <0.01 µM. Compounds I-42, I-43, I-49, I-50, I-51, I-52, I-54, I-55, I-56, I-57, I-58, I-59, I-62, I-65, I-66, I-67, I-68, I-71, I-72, I-75, I-76, I-77, I-78, I-80, I-81, I-83, I-85, I-86, I-88, I-89, I-90, I-91, I-94, I-97, I-99, I-101, I-105, and I-106, were shown to have $K_i$ values of 0.01-1 µM. Compounds I-44, I-45, I-46, I-47, I-53, I-60, I-61, I-63, I-64, I-69, I-70, I-84, I-93, I-95, I-96, I-102, I-107, I-133, I-134, and I-135, were shown to have $K_i$ values of >1 µM.

Compounds of the present invention were also tested and found to inhibit JAK-2.

Example 9

PDK-Inhibition Assay

Compounds were screened for their ability to inhibit PDK-1 using a radioactive-phosphate incorporation assay (Pitt and Lee, J. Biomol. Screen., (1996) 1, 47). Assays were carried out in a mixture of 100 mM HEPES (pH 7.5), 10 mM $MgCl_2$, 25 mM NaCl, 2 mM DTT. Final substrate concentrations in the assay were 40 µM ATP (Sigma Chemicals) and 65 µM peptide (PDKtide, Upstate, Lake Placid, N.Y.). Assays were carried out at 30° C. and 25 nM PDK-1 in the presence of ~27.5 nCi/µL of [γ-$^{32}$P]ATP (Amersham Pharmacia Biotech, Amersham, UK). An assay stock buffer solution was prepared containing all of the reagents listed above, with the exception of ATP, and the test compound of interest. 15 µl of the stock solution was placed in a 96 well plate followed by addition of 1 µl of 0.5 mM DMSO stock containing the test compound (final compound concentration 25 µM, final DMSO concentration 0.5%). The plate was preincubated for about 10 minutes at 30° C. and the reaction initiated by addition of 4 µl ATP (final concentration 40 µM).

The reaction was stopped after 10 minutes by the addition of 100 µL 100 mM phosphoric acid, 0.01% Tween-20. A phosphocellulose 96 well plate (Millipore, Cat no. MAPH-NOB50) was pretreated with 100 µL 100 mM phosphoric acid, 0.01% Tween-20 prior to the addition of the reaction mixture (100 µL). The spots were left to soak for at least 5 minutes, prior to wash steps (4×200 µL 100 mM phosphoric acid, 0.01% Tween-20). After drying, 20 µL Optiphase 'SuperMix' liquid scintillation cocktail (Perkin Elmer) was added to the well prior to scintillation counting (1450 Microbeta Liquid Scintillation Counter, Wallac).

Compounds showing greater than 50% inhibition versus standard wells containing the assay mixture and DMSO without test compound were titrated to determine $IC_{50}$ values.

Compounds of the invention were tested and were found to inhibit PDK-1. Compounds I-74, I-103, and I-104 were shown to have a $K_i$ value of <1 µM. Compounds I-42, I-65, I-83, I-84, and I-134 were shown to have a $K_i$ value of 1-10 µM.

Example 10

Inhibition of AUR-2

Compounds are screened in the following manner for their ability to inhibit Aurora-2 using a standard coupled enzyme assay (Fox et al (1998) *Protein Sci* 7, 2249). To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 µM peptide (LR-RASLG, American Peptide, Sunnyvale, Calif.) is added a DMSO solution of a compound of the present invention to a final concentration of 30 µM. The resulting mixture is incubated at 30° C. for 10 min. The reaction was initiated by the addition of 10 µL of Aurora-2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The $K_i$ values are determined from the rate data as a function of inhibitor concentration.

Compounds of the invention were tested and were found to inhibit AUR-2. Compounds I-73, I-74, I-75, I-77, I-78, I-79, I-82, I-85, I-86, I-87, I-88, and I-89 were shown to have $K_i$ values of <0.1 µM. Compounds I-42, I-43, I-65, I-66, I-67, I-71, I-72, I-83, I-103, and I-105 were shown to have $K_i$ values of 0.1-1 µM. Compounds I-45 and I-46 were shown to have $K_i$ values of >1 µM.

Example 11

Inhibition of KDR

Compounds were screened for their ability to inhibit KDR using a standard coupled enzyme assay (Fox et al., Protein Sci., (1998) 7, 2249). Assays were carried out in a mixture of 200 mM HEPES 7.5, 10 mM MgCl2, 25 mM NaCl, 1 mM DTT and 1.5% DMSO. Final substrate concentrations in the assay were 300 µM ATP (Sigma Chemicals) and 10 µM poly E4Y (Sigma). Assays were carried out at 37° C. and 30 nM KDR. Final concentrations of the components of the coupled enzyme system were 2.5 mM phosphoenolpyruvate, 200 µM NADH, 30 µg/ML pyruvate kinase and 10 µg/ml lactate dehydrogenase.

An assay stock buffer solution was prepared containing all of the reagents listed above, with the exception of ATP and the test compound of interest. 177 µl of the stock solution was placed in a 96 well plate followed by addition of 3 µl of 2 mM DMSO stock containing the test compound (final compound concentration 30 µM). The plate was preincubated for about 10 minutes at 37° C. and the reaction initiated by addition of 20 µl of ATP (final concentration 300 µM). Rates of reaction were obtained using a Molecular Devices plate reader (Sunnyvale, Calif.) over a 5 minute read time at 37° C. Compounds showing greater than 50% inhibition versus standard wells containing the assay mixture and DMSO without test compound were titrated to determine $IC_{50}$ values determined.

Compounds of the present invention were found to inhibit KDR. Compounds I-49, I-51, I-52, I-54, I-56, I-57, I-58, I-59, I-62, I-73, I-74, I-75, I-78, I-79, I-81, I-82, I-87, I-92, I-97, I-98, I-99, and I-100 were shown to have $K_i$ values of <0.1 µM. Compounds I-50, I-53, I-55, I-61, I-65, I-66, I-67, I-71, I-72, I-76, I-77, I-80, I-83, I-85, I-86, I-88, I-89, I-90, I-91, I-93, I-94, I-95, I-96, I-101, I-102, I-105, I-106, and I-134 were shown to have $K_i$ values of 0.1-1 µM. Compounds I-60, I-63, I-64, I-68, I-69, I-70, I-84, and 1-107, were shown to have $K_i$ values of >1 µM While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

The invention claimed is:
1. A compound having the formula:

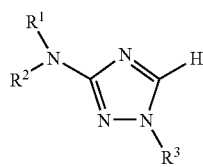

II or a pharmaceutically acceptable salt thereof, wherein
$R^1$ is hydrogen or $C_{1-6}$ alkyl;
$R^2$ is $Ar^1$ or $Cy^1$, wherein $Ar^1$ is a group selected from phenyl, pyridyl, pyrimidinyl, pyrazinyl, furanyl, thienyl pyrrolyl, pyrazolyl, triazolyl, imidazolyl, oxazolyl, isoxazolyl, oxadiazolyl, thiazolyl, isothiazolyl, or thiadiazolyl and $Cy^1$ is selected from cyclopropyl, cyclopentyl, cyclohexyl, piperidinyl, piperazinyl, morpholinyl, pyrrolidinyl, pyrazolinyl, tetrahydropyranyl, or tetrahydrofuranyl; wherein each of $Ar^1$ and $Cy^1$ is optionally substituted with 0-5 independent occurrences of Q—$R^X$; wherein each independent occurrence of Q is a bond or is a $C_{1-6}$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each independent occurrence of $R^X$ is independently selected from R', halogen, $NO_2$, CN, OR', SR', N(R')$_2$, NR'C(O)R', NR'C(O)N (R')$_2$, $NR'CO_2R'$, C(O)R', $CO_2R'$, OC(O)R', C(O)N (R')$_2$, OC(O)N(R')$_2$, SOR', $SO_2R'$, $SO_2N(R')_2$, $NR'SO_2R'$, $NR'SO_2N(R')_2$, C(O)C(O)R', or C(O)$CH_2$C (O)R';
wherein $R^3$ is $Ar^2$, wherein $Ar^2$ is an optionally substituted aryl group selected from pyridinyl or pyrimidinyl, optionally substituted with up to five substituents selected from Z-$R^Y$; wherein Z is a bond or is a $C_{1-6}$ alkylidene chain wherein up to two non-adjacent methylene units of Z are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^Y$ is independently selected from R', halogen, $NO_2$, CN, OR', SR', N(R')$_2$, NR'C(O)R', NR'C(O)N(R')$_2$, $NR'CO_2R'$, C(O)R', $CO_2R'$, OC(O)R', C(O)N(R')$_2$, OC(O)N(R')$_2$, SOR', $SO_2R'$, $SO_2N(R')_2$, $NR'SO_2R'$, $NR'SO_2N(R')_2$, C(O)C(O)R', or C(O)$CH_2$C(O)R';
each occurrence of R is independently selected from hydrogen or an optionally substituted $C_{1-6}$ aliphatic group; and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together, or two occurrences of R' taken together, form a 5-8 membered cycloalkyl, heterocyclyl, aryl, or heteroaryl ring having 0-3 heteroatoms independently selected from nitrogen, oxygen, or sulfur;
each of the optional substituents of said aryl or heteroaryl ring is selected from halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph) optionally substituted with R°; —CH=CH(Ph) optionally substituted with R°; —NO$_2$; —CN; —N(R°)$_2$; —NR°C(O)R°; —NR°C (S)R°; —NR°C(O)N(R°)$_2$; —NR°C(S)N(R°)$_2$; —NR°CO$_2$R°; —NR°NR°C(O)R°; —NR°NR°C(O)N (R°)$_2$; —NR°NR°CO$_2$R°; —C(O)C(O)R°; —C(O) CH$_2$C(O)R°; —CO$_2$R°; —C(O)R°; —C(S)R°; —C(O) N(R°)$_2$; —C(S)N(R°)$_2$; —C=(NH)—N(R°)$_2$, —OC (O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$ NHC(O)R°; wherein each independent occurrence of R° is selected from hydrogen, an optionally substituted $C_{1-6}$ aliphatic, an unsubstituted 5-6 membered heteroaryl or heterocyclic ring, phenyl, —O(phenyl), or —CH$_2$(phenyl), wherein optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$ aliphatic), NO$_2$, CN, CO$_2$H, CO$_2$(C$_{1-4}$aliphatic), O(haloC$_{1-4}$aliphatic), or haloC$_{1-4}$aliphatic, or two independent occurrences of R°, on the same substituent or different substituents, taken together with the atom(s) to which each R° group is bound, form a 3-12 membered saturated, partially unsaturated, or fully unsaturated monocyclic or bicyclic ring having 0-4 heteroatoms independently selected from nitrogen, oxygen, or sulfur;
each of the optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$ SO$_2$R$^+$; wherein R$^+$ is hydrogen, an optionally substituted $C_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur, wherein optional substituents on the aliphatic group or the phenyl ring of R⁺ are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(halo C₁₋₄ aliphatic), or halo(C₁₋₄ aliphatic), wherein each of the foregoing C₁₋₄ aliphatic groups of R⁺ is unsubstituted;

each of the optional substituents on said alkylidene chain, aliphatic, cycloalkyl, or heterocyclyl is selected from the list of optional substituents of optional substituents for aryl and heteroaryl rings and further comprise =O, =S, =NNHR*, =NN(R*)₂, =NNHC(O)R*, =NNHCO₂(alkyl), =NNHSO₂(alkyl), or =NR*, where each R* is independently selected from hydrogen or a C₁₋₆ aliphatic group; and provided that when R³ is 4,6-dimethoxy 2-pyrimidinyl, and R¹ is hydrogen, then R² is not o-S(O)Me phenyl.

2. The compound of claim 1, wherein R¹ is hydrogen and R² is optionally substituted phenyl.

3. The compound of claim 1, wherein R¹ is hydrogen and R² is optionally substituted cyclohexyl, tetrahydrofuranyl, or cyclopropyl.

4. The compound of claim 1, wherein each occurrence of QR$^X$ or ZR$^Y$ is independently halogen, CN, NO₂, or an optionally substituted group selected from C₁₋₄ alkyl, aryl, aralkyl, —N(R')₂, —CH₂N(R')₂, —OR', —CH₂OR', —SR', —CH₂SR', —COOR', —NRCOR', —CON(R')₂, or —SO₂N(R')₂.

5. The compound of claim 1, wherein R² is phenyl, cyclohexyl, tetrahydrofuranyl, or cyclopropyl, optionally substituted with 0-3 occurrences of QR$^X$.

6. A compound selected from one of the following compounds:

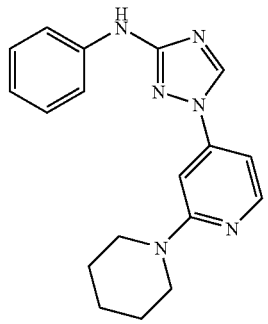
I-49

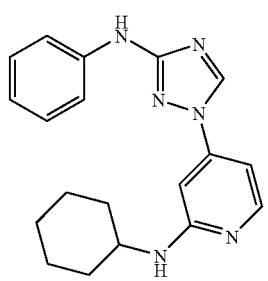
I-50

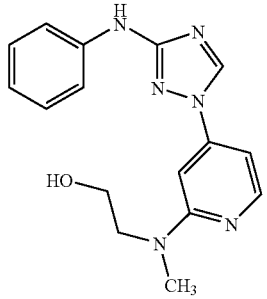
I-51

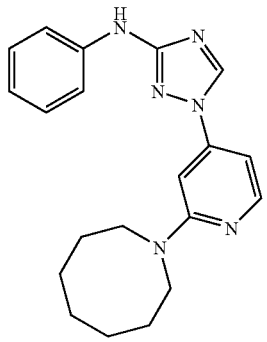
I-52

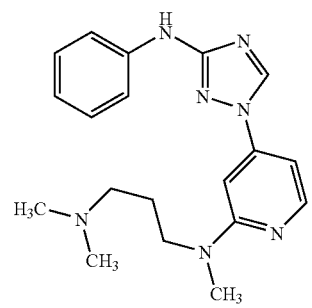
I-53

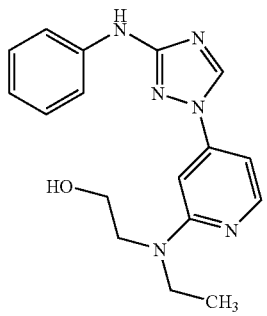
I-54

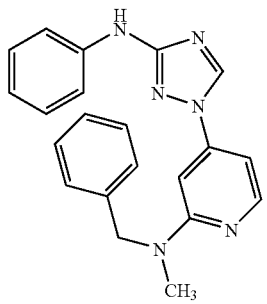
I-55

-continued
I-56
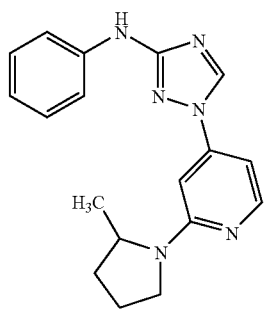
I-57
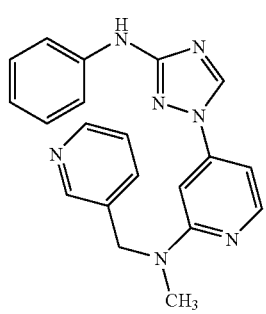
I-58
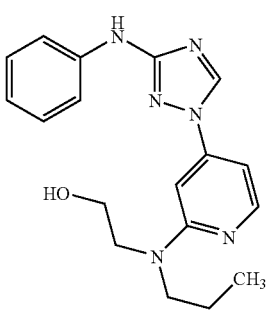
I-59
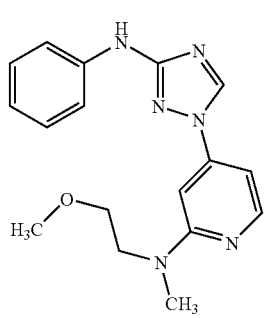
I-60
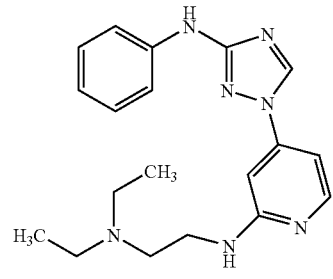
-continued
I-61
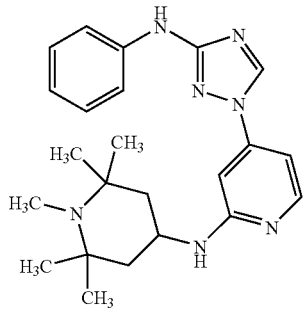
I-62
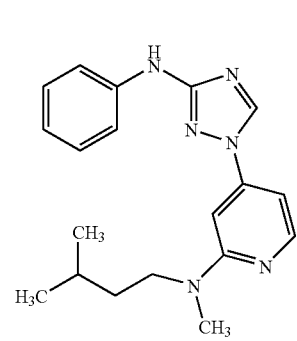
I-63
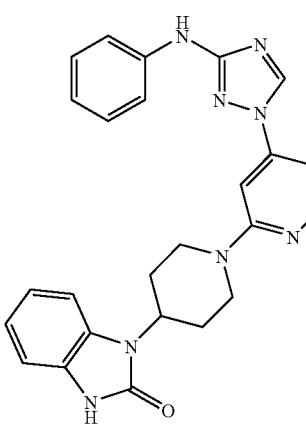
I-64
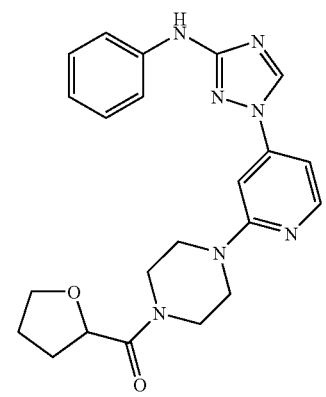

-continued
I-65
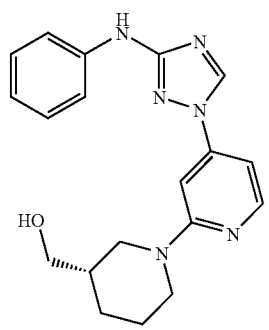
I-66
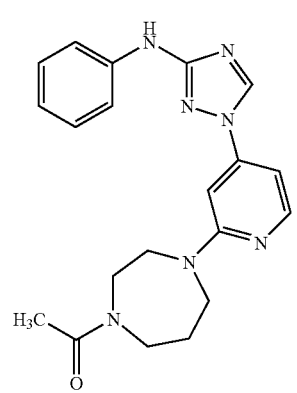
I-67
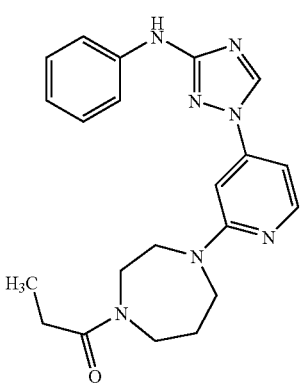
I-68
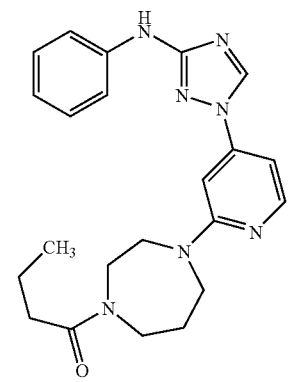
-continued
I-69
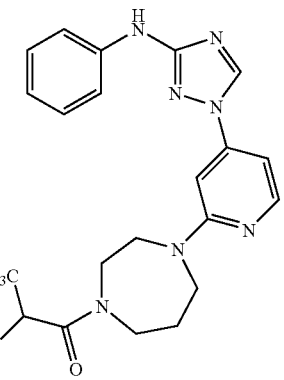
I-70
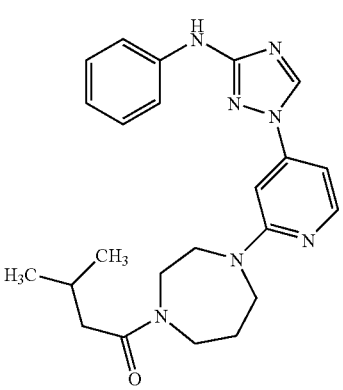
I-71
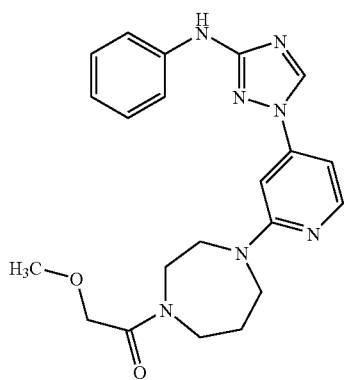
I-72
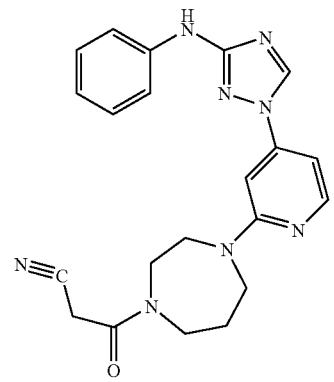

-continued
I-73
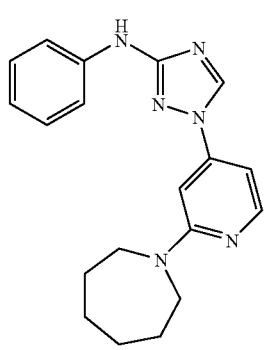
I-74
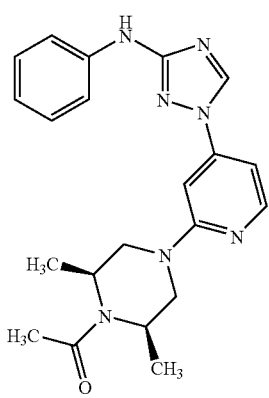
I-75
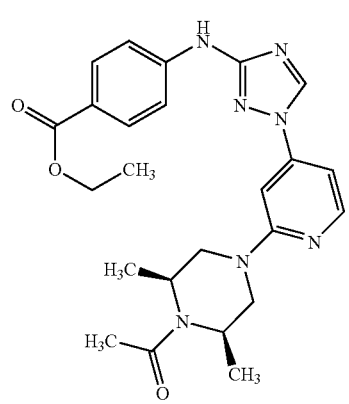
I-76
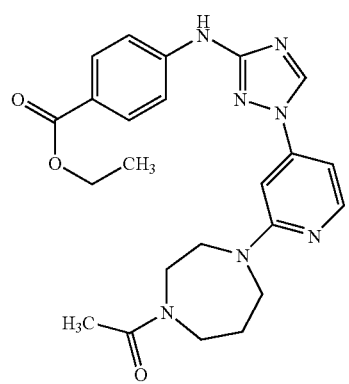
-continued
I-77
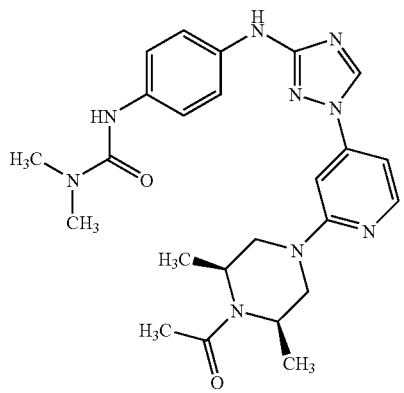
I-78
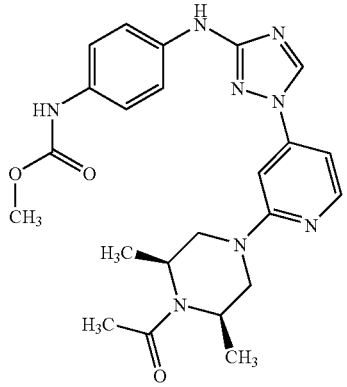
I-79
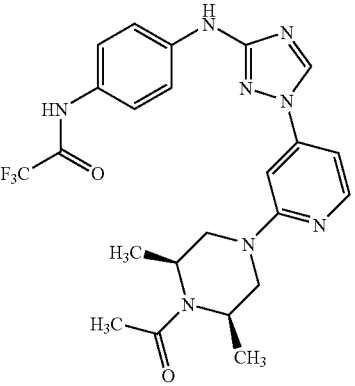
I-80
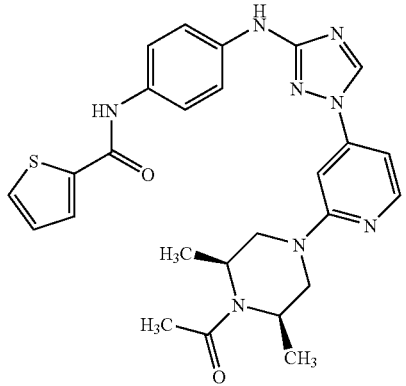

I-81
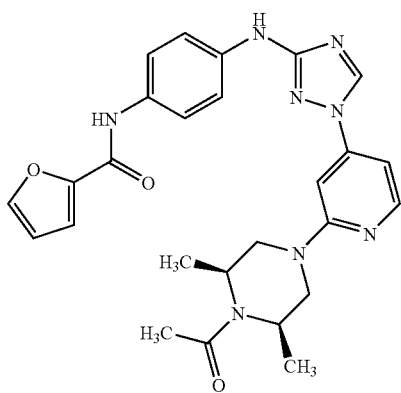
I-82
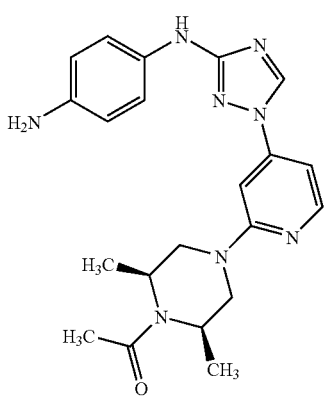
I-83
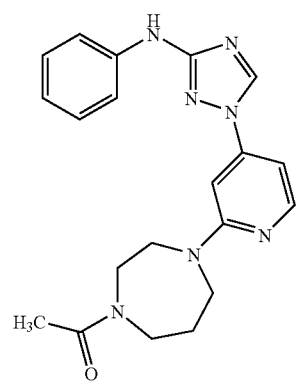
I-84
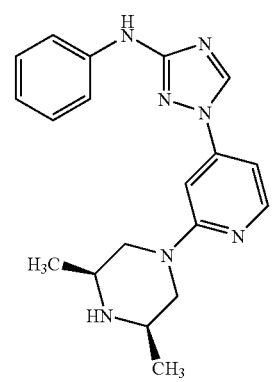
I-85
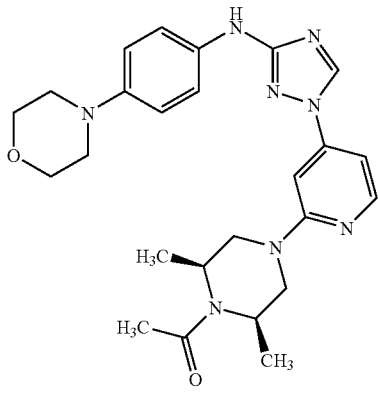
I-86
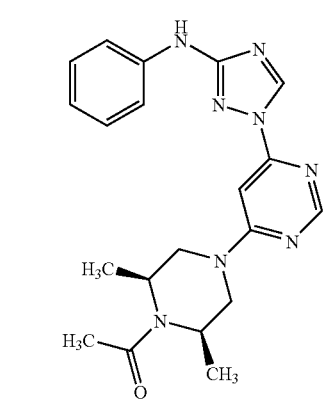
I-87
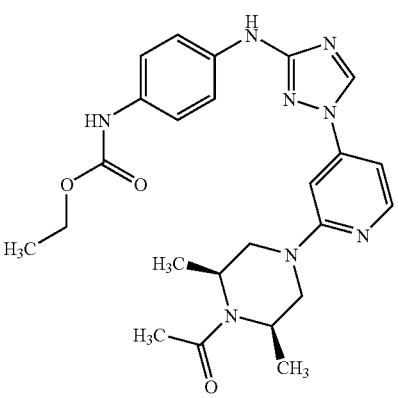
I-88
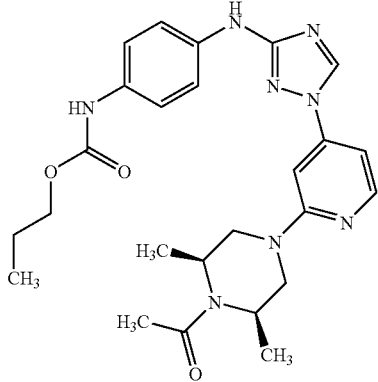

I-89
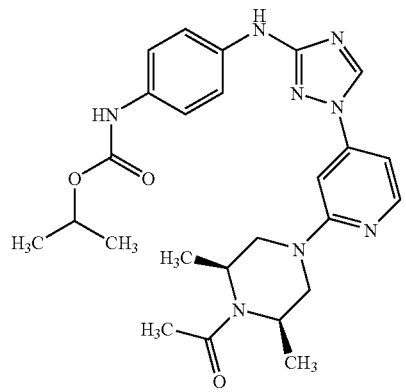
I-90
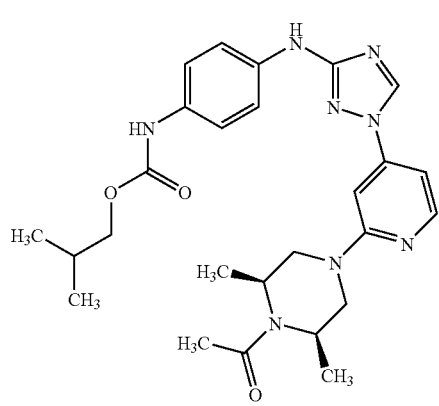
I-91
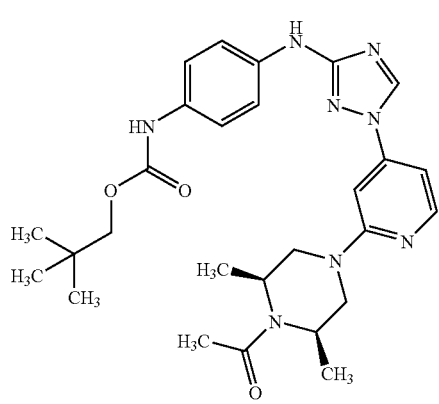
I-92
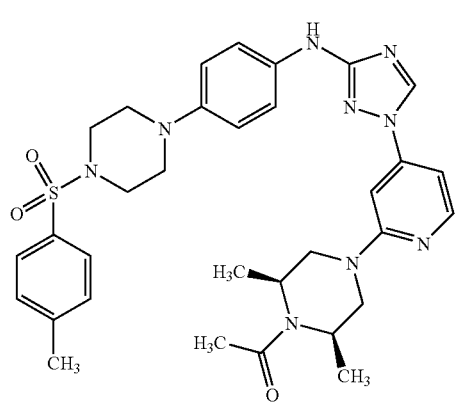
I-93
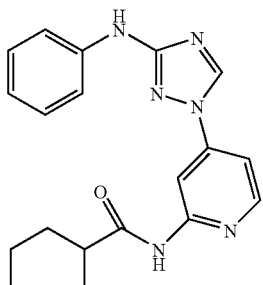
I-94
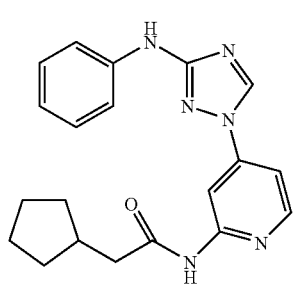
I-95
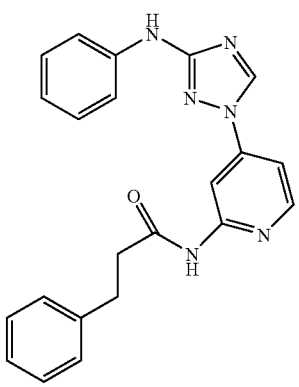
I-96
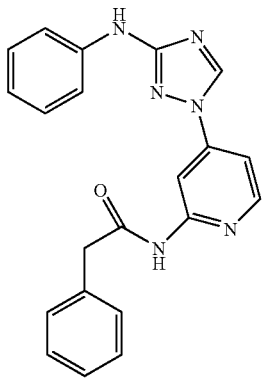

-continued
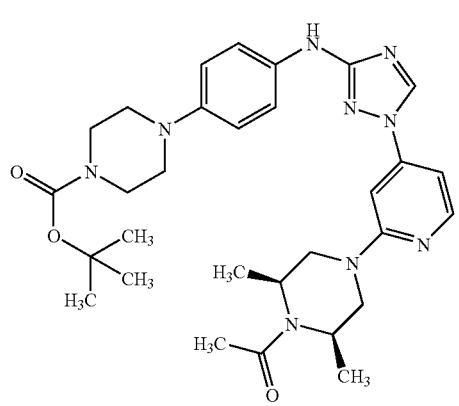
I-97
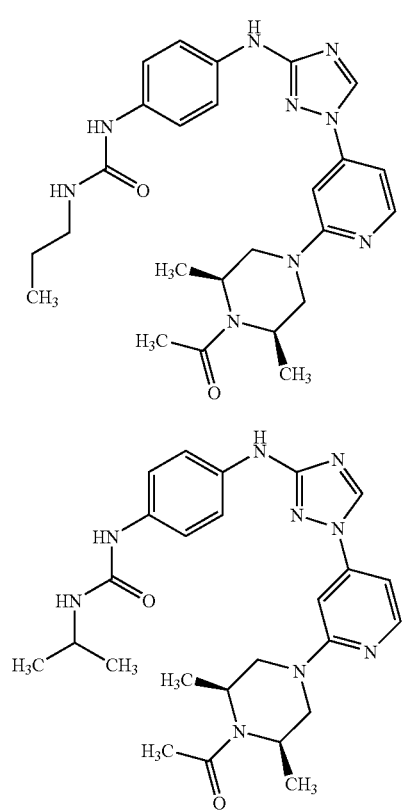
I-98
I-99
I-100
-continued
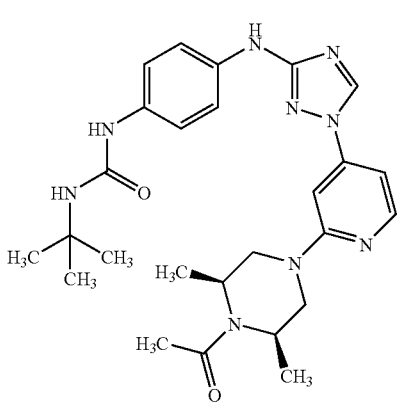
I-101
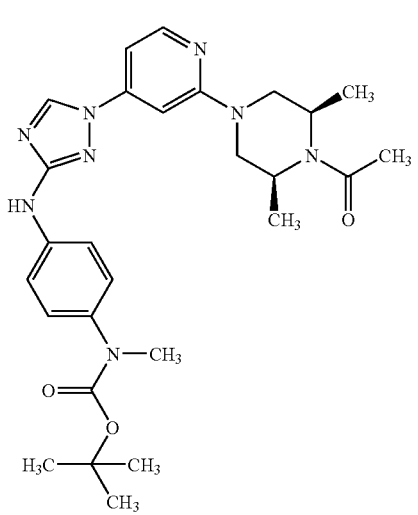
I-103
I-104
I-109

-continued
I-110
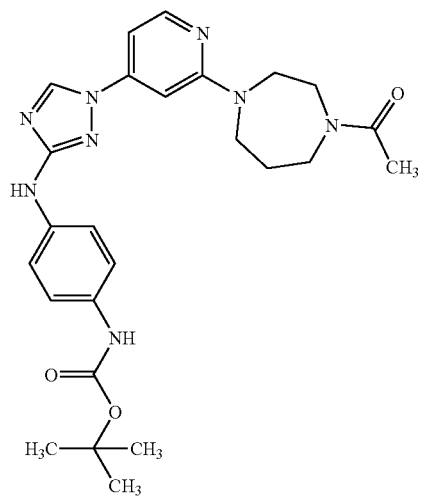
I-111
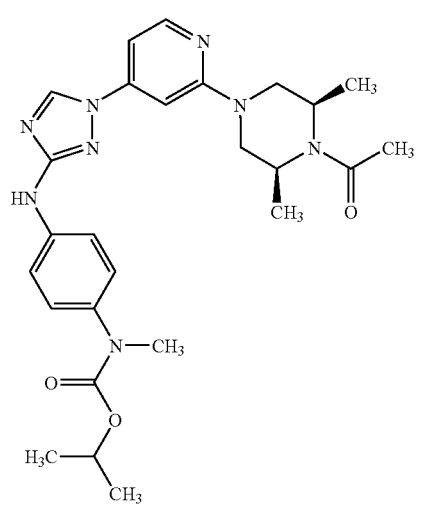
I-112
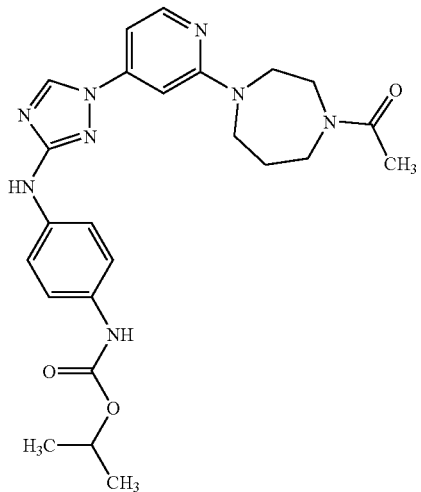
-continued
I-113
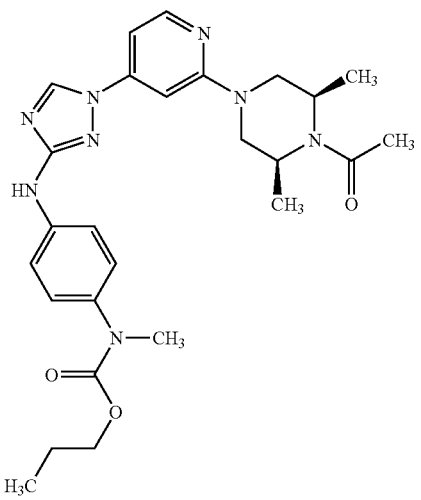
I-114
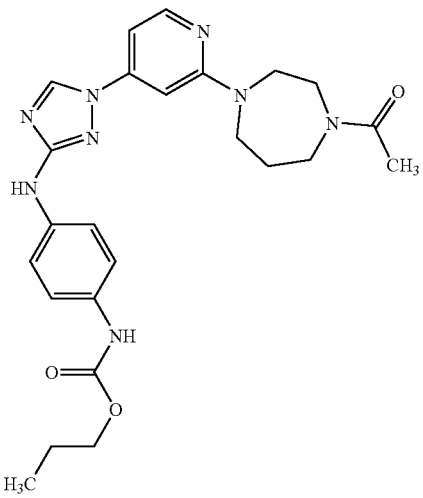
I-115
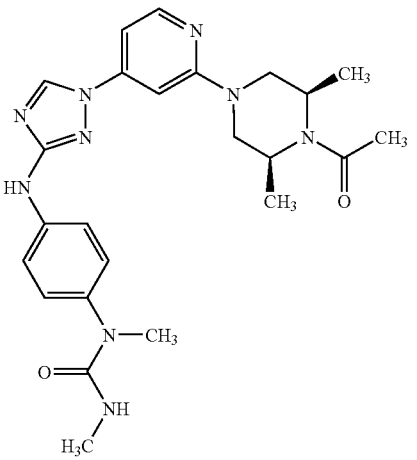

-continued
I-116
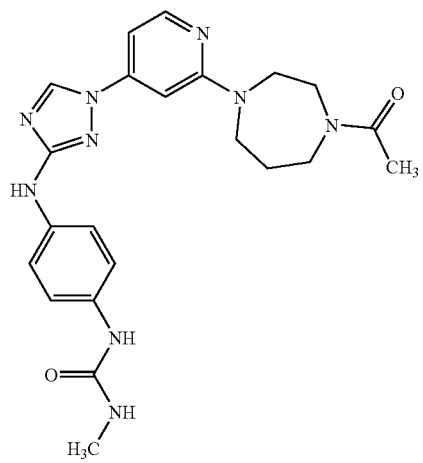
I-117
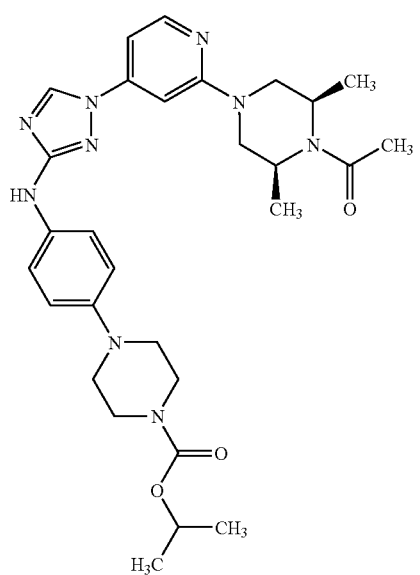
I-118
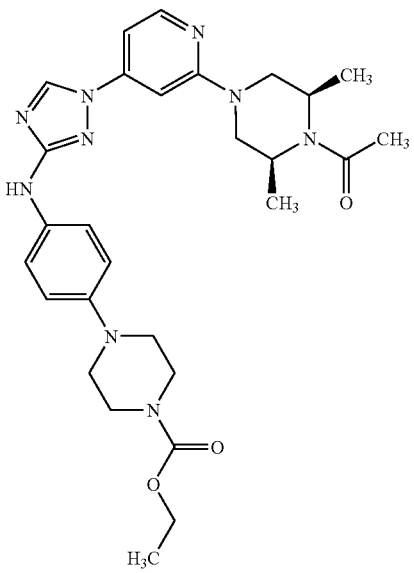
-continued
I-119
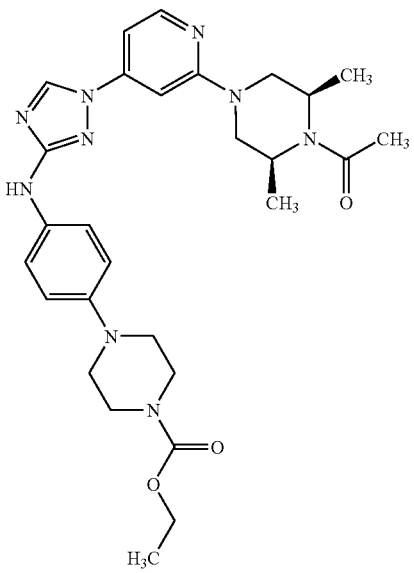
I-120
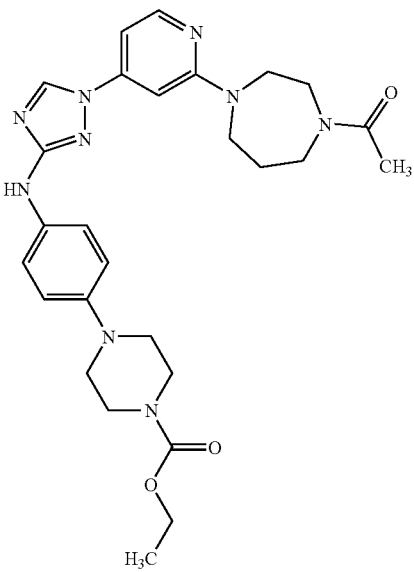

-continued
I-121
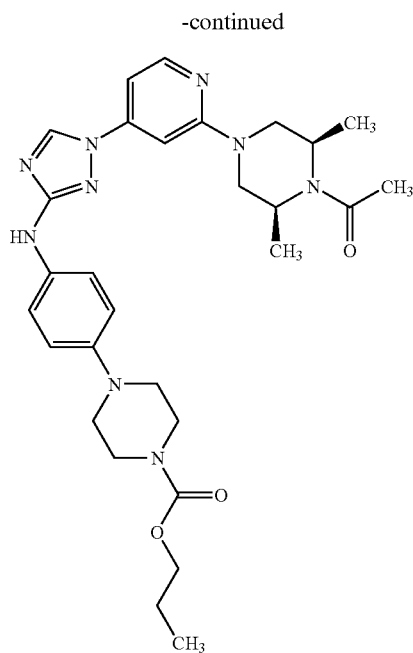
I-122
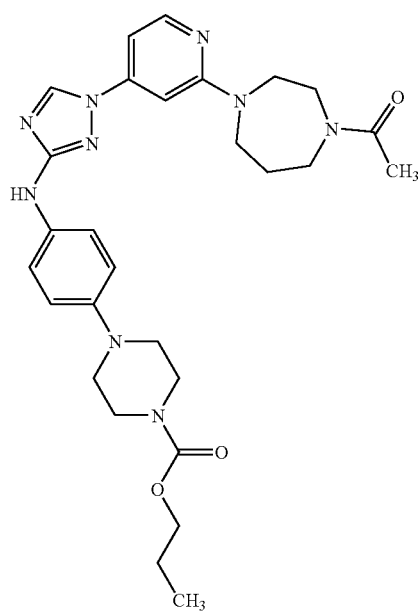
-continued
I-123
I-124
I-125
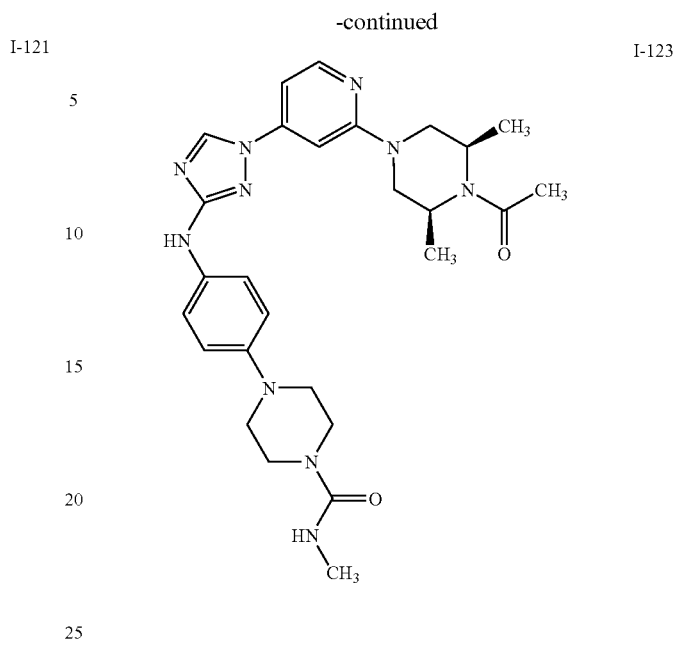
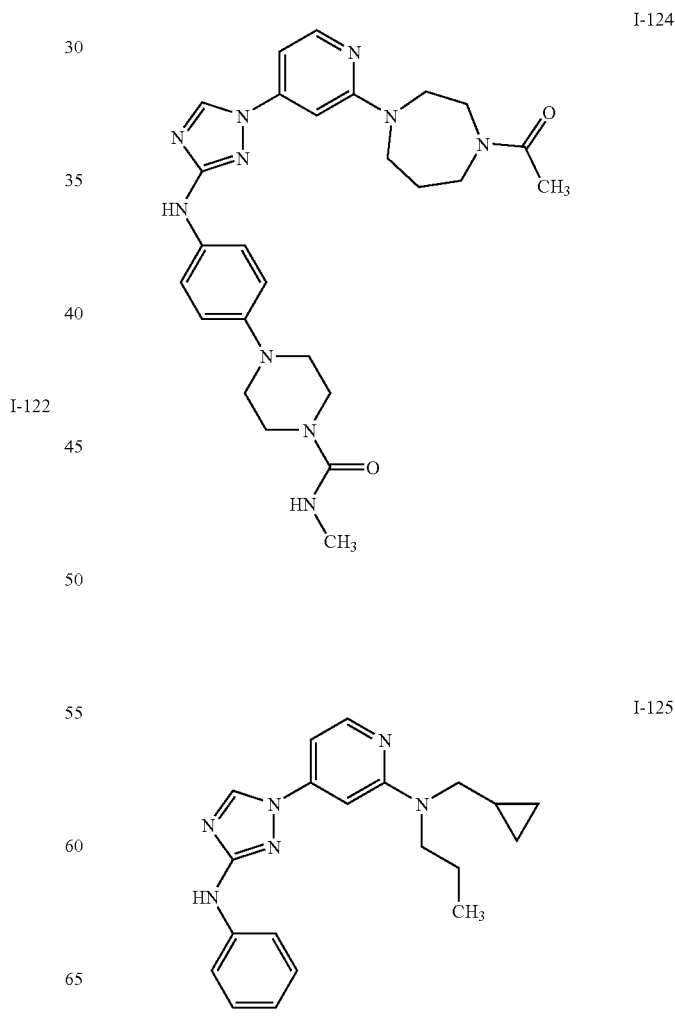

I-126 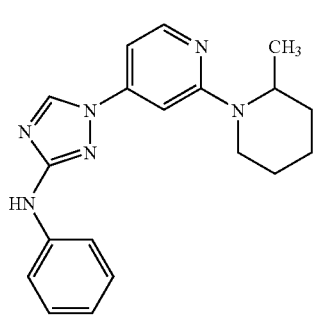
I-127 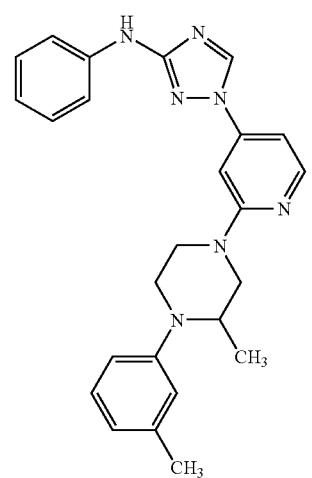
I-128 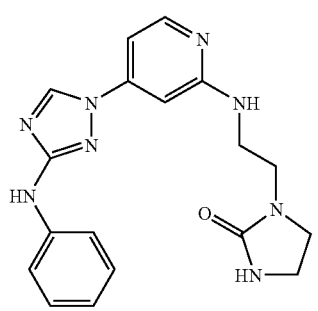
I-129 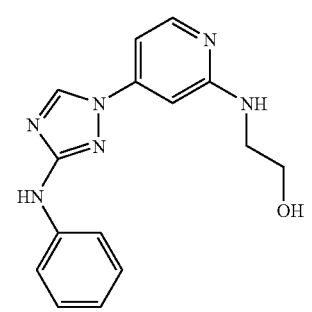
I-130 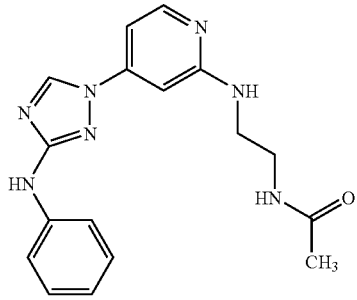
I-131 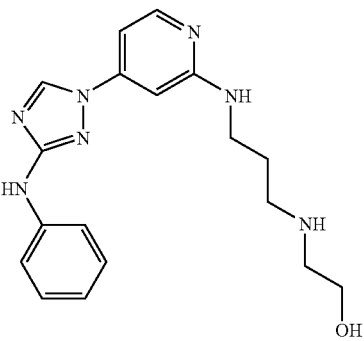
I-132 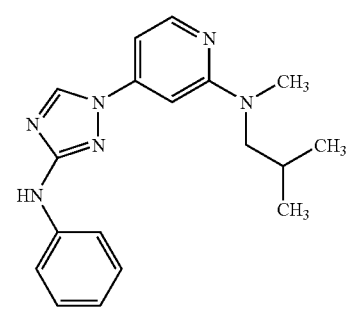
I-133 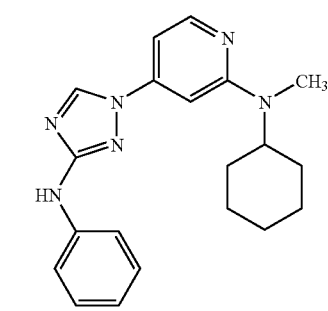
I-136 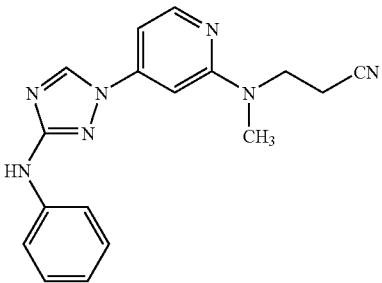

I-137 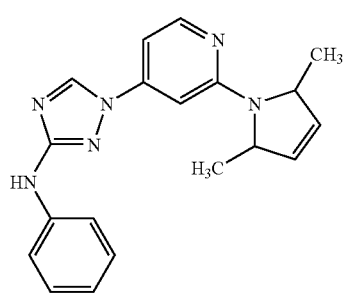
I-138 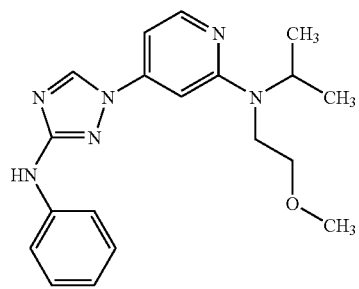
I-139 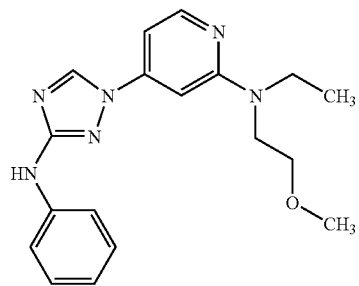
I-140 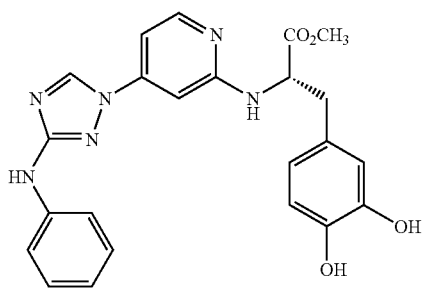
I-141 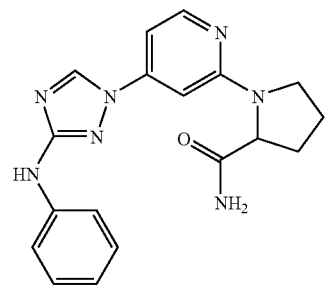
I-142 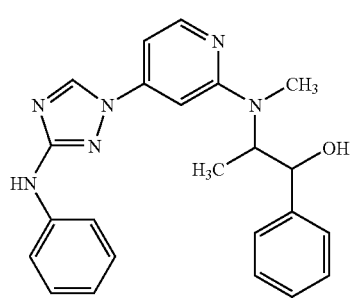
I-143 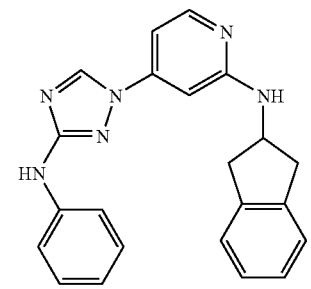
I-144 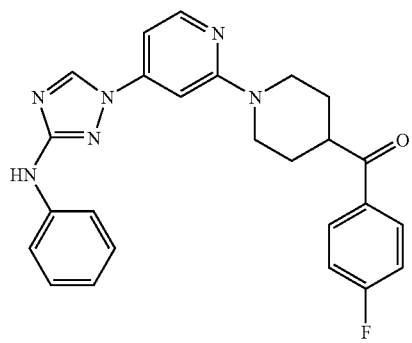
I-145 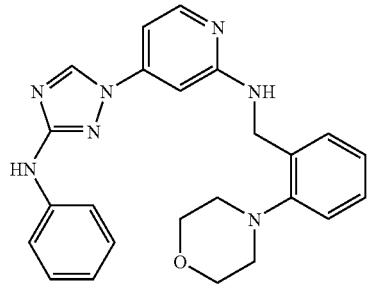
I-146 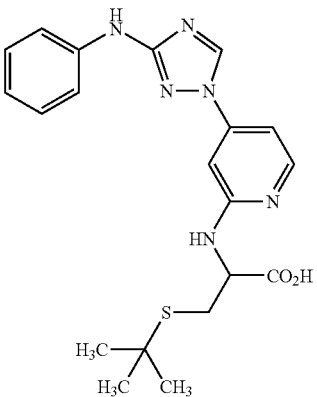

-continued
I-147
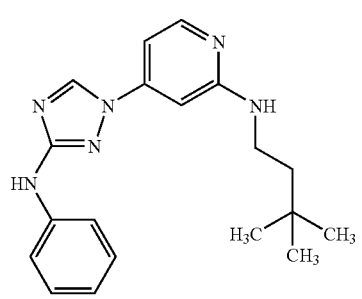
I-148
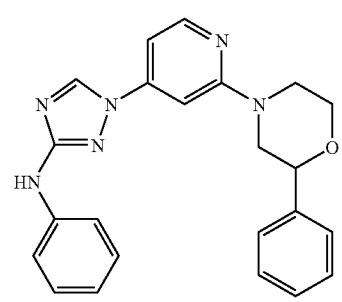
I-149
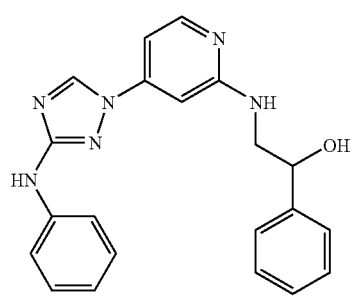
I-150
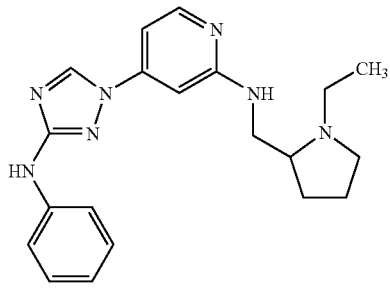
I-151
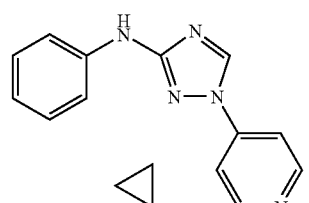
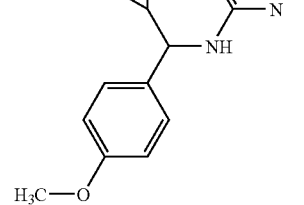
-continued
I-152
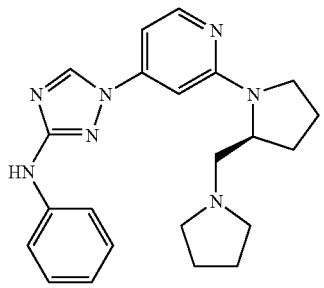
I-153
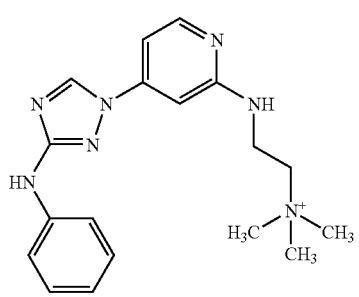
I-154
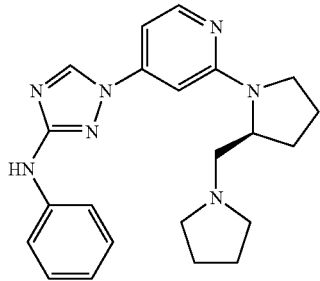
I-155
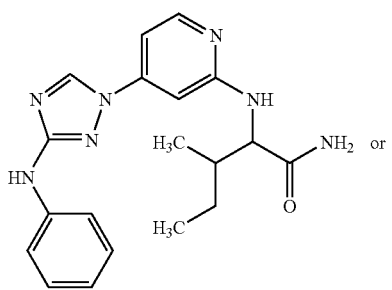
or
I-156
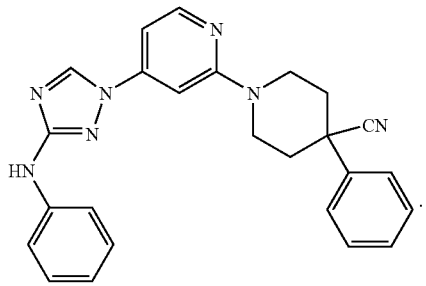

7. The compound of claim 1 having formula II-X-(i):

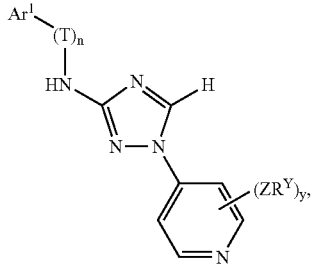

wherein n is 0.

8. The compound of claim 1 having formula II-J-(i):

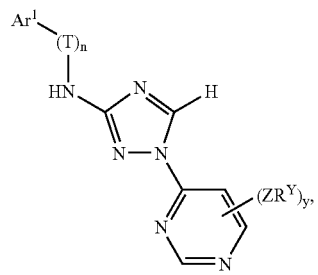

wherein n is 0.

9. The compound of claim 1, wherein each $QR^X$ is independently halogen, CN, $NO_2$, or an optionally substituted group selected from $C_{1-4}$ alkyl, aryl, aralkyl, —N(R')$_2$, —CH$_2$N(R')$_2$, —OR', —CH$_2$OR', —SR', —CH$_2$SR', —COOR', —COR', —NRCOR', —NRCONRR', —NRCOOR', —CON(R')$_2$, or —SO$_2$N(R')$_2$.

10. The compound of claim 1, wherein each $QR^X$ is independently Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —N(H)C(O)N(H)CH$_3$, —N(H)C(O)OCH$_3$, —N(H)C(O)N(H)Et, —N(H)C(O)OEt, —N(H)C(O)N(H)-iPr, —N(H)C(O)O-iPr, —N(H)C(O)N(H)-nPr, —N(H)C(O)O-nPr, —SO$_2$NH$_2$, methylenedioxy, ethylenedioxy, piperidinyl, piperizinyl, morpholino, or an optionally substituted group selected from $C_{1-4}$ alkoxy, phenyl, phenyloxy, benzyl, or benzyloxy.

11. The compound of claim 1, wherein each $QR^X$ is independently —N(R')$_2$, —NRR', —N(R)$_2$, —NRCOR', —NRCONRR', —NRCOOR', piperidinyl, piperizinyl, or morpholino, wherein the piperidinyl, piperizinyl, morpholino is optionally substituted with —COR', —COOR', —CON(R')$_2$, or —SO$_2$N(R')$_2$, wherein each occurrence of R in $QR^X$ is independently H or $C_{1-6}$ alkyl.

12. The compound of claim 11, wherein R in $QR^X$ is H and R' in $QR^X$ is $C_{1-6}$ alkyl.

13. The compound of claim 1, wherein $Ar^2$ has the following formula:

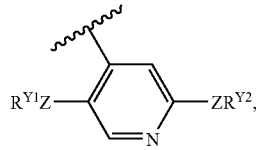

wherein
$ZR^{Y1}$ and $ZR^{Y1}$ are $ZR^Y$.

14. The compound of claim 13, wherein $ZR^{Y1}$ is hydrogen, halogen, $C_{1-6}$ alkyl, $C_{1-4}$ alkoxy, CN, or $NO_2$.

15. The compound of claim 14, wherein $ZR^{Y2}$ is halogen, $C_{1-6}$ alkyl, CN, $NO_2$, or an optionally substituted group selected from $C_{1-4}$ alkyl, aryl, aralkyl, —N(R')$_2$, —CH$_2$N(R')$_2$, —OR', —CH$_2$OR', —SR', —CH$_2$SR', —COOR', —COR', —NRCOR', —NRCONRR', —NRCOOR', —CON(R')$_2$, or —SO$_2$N(R')$_2$.

16. The compound of claim 1, wherein $Ar^2$ has the following formula:

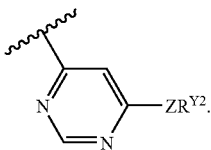

17. The compound of claim 16, wherein $ZR^{Y2}$ is halogen, $C_{1-6}$ alkyl, CN, $NO_2$, or an optionally substituted group selected from $C_{1-4}$ alkyl, aryl, aralkyl, —N(R')$_2$, —CH$_2$N(R')$_2$, —OR', —CH$_2$OR', —SR', —CH$_2$SR', —COOR', —COR', —NRCOR', —NRCONRR', —NRCOOR', —CON(R')$_2$, or —SO$_2$N(R')$_2$.

18. The compound of claim 17, wherein $ZR^{Y2}$ is —N(R)$_2$, —N(R')$_2$, or —NRR', wherein R is H or $C_{1-6}$ alkyl and R' is $C_{1-6}$ alkyl, wherein the $C_{1-6}$ alkyl is optionally substituted with halo, CN, OH, or —O$C_{1-6}$ alkyl.

19. The compound of claim 18, wherein $ZR^{Y2}$ is —N(R')$_2$, where each occurrences of R' taken together, forms a 5-10 membered heterocyclic ring having 1-3 heteroatoms independently selected from nitrogen, oxygen, or sulfur, wherein the heterocyclic ring is optionally substituted with halo, $C_{1-6}$ alkyl, —COR', —COOR', —CON(R')$_2$, —NRCOR', —NRCOOR', —NRCONRR', or —SO$_2$N(R')$_2$, where each occurrence of R is hydrogen or $C_{1-6}$ alkyl and each occurrence of R' is $C_{1-6}$ alkyl.

20. The compound of claim 19, wherein R is hydrogen.

21. A composition comprising a compound of claim 1 and a pharmaceutically acceptable carrier, adjuvant, or vehicle.

22. The composition of claim 21, further comprising an additional therapeutic agent selected from a chemotherapeutic or anti-proliferative agent, a treatment for Alzheimer's Disease, a treatment for Parkinson's Disease, an agent for treating Multiple Sclerosis (MS), a treatment for asthma, an agent for treating schizophrenia, an anti-inflammatory agent, an immunomodulatory or immunosuppressive agent, a neurotrophic factor, an agent for treating cardiovascular disease, an agent for treating liver disease, an agent for treating a blood disorder, or an agent for treating an immunodeficiency disorder.

* * * * *